US00RE43050E

(19) United States
(12) Reissued Patent
Lyster et al.

(10) Patent Number: US RE43,050 E
(45) Date of Reissued Patent: Dec. 27, 2011

(54) MEDICAL ELECTRODE AND RELEASE LINER CONFIGURATIONS FACILITATING PACKAGED ELECTRODE CHARACTERIZATION

(75) Inventors: Thomas D. Lyster, Bothell, WA (US); Thomas Solosko, Issaquah, WA (US); Carlton B. Morgan, Bainbridge Island, WA (US); Kim J. Hansen, Renton, WA (US); Daniel J. Powers, Issaquah, WA (US); Hans Patrick Griesser, Bainbridge Island, WA (US); Eric L. Jonsen, Seattle, WA (US); David E. Snyder, Bainbridge Island, WA (US)

(73) Assignee: Koninklijke Philips Electronics N.V., Eindhoven (NL)

(21) Appl. No.: 11/121,327

(22) Filed: May 2, 2005

Related U.S. Patent Documents

Reissue of:
(64) Patent No.: 6,694,193
Issued: Feb. 17, 2004
Appl. No.: 09/954,750
Filed: Sep. 14, 2001

(51) Int. Cl.
*A61N 1/04* (2006.01)
(52) U.S. Cl. ..... 607/142
(58) Field of Classification Search ..... 607/142–156; 600/372–392
See application file for complete search history.

(56) References Cited

U.S. PATENT DOCUMENTS 4,034,854 A 7/1977 Bevilacqua
5,352,315 A * 10/1994 Carrier et al. ..... 156/267
5,402,884 A 4/1995 Gilman et al.
5,579,919 A 12/1996 Gilman et al.
5,653,682 A 8/1997 Sibalis
5,792,090 A 8/1998 Ladin
5,817,151 A 10/1998 Olson et al.
5,984,102 A 11/1999 Tay
6,047,212 A 4/2000 Gliner et al.
6,096,942 A * 8/2000 Hack ..... 602/41
6,115,638 A 9/2000 Groenke

* cited by examiner

*Primary Examiner* — Scott M Getzow
(74) *Attorney, Agent, or Firm* — W. Brinton Yorks, Jr.

(57) ABSTRACT

An electrode includes a conductive adhesive layer and a conductive foil layer having a void therein. One such electrode may be mounted in conjunction with another electrode upon a release liner having one or more openings therein to facilitate electrical signal exchange between electrodes. A release liner may include a moisture permeable and/or moisture absorbent membrane. A release liner may alternatively include a conductive backing layer. A release liner may also include an insulating swatch covering an opening. A release liner may be implemented as a foldable sheet, such that multiple electrodes may be mounted upon the same side of the foldable sheet. A medical device to which the mounted electrodes are coupled may characterize the electrical path between the electrodes. The medical device may perform a variety of electrical measurements, including real and/or complex impedance measurements. Based upon one or more measurements, the medical device may provide an indication of electrode condition, fitness for use, and/or an estimated remaining lifetime. An electrode condition indicator, which may form a portion of the medical device, may generate, present, or display electrode condition and/or estimated remaining lifetime information via a visual metaphor, such as a fuel gauge.

15 Claims, 55 Drawing Sheets

MEDICAL ELECTRODE AND RELEASE LINER CONFIGURATIONS FACILITATING PACKAGED ELECTRODE CHARACTERIZATION

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates generally to the testing of medical electrodes that are mounted on a release liner. More particularly, the invention is directed to various electrode and/or release liner embodiments that facilitate testing and characterization of packaged electrodes.

2. Description of the Background Art

Sudden Cardiac Arrest (SCA) is one of the leading causes of death in the industrialized world. SCA typically results from an arrhythmia condition known as Ventricular Fibrillation (VF), during which a patient's heart muscle exhibits extremely rapid, uncoordinated contractions that render the heart incapable of circulating blood. Statistically, after four minutes have elapsed, the patient's chance of survival decreases by 10% during each subsequent minute they fail to receive treatment.

An effective treatment for VF is electrical defibrillation, in which a defibrillator delivers an electrical pulse, waveform, or shock to the patient's heart. Because the onset of VF is generally an unpredictable event, the likelihood that a victim will survive increases dramatically if 1) defibrillation equipment is nearby; 2) such equipment is in proper working order; and 3) such equipment may be easily, rapidly, and effectively deployed to treat the patient.

Medical equipment manufacturers have developed Automated External Defibrillators (AEDs) that minimally trained personnel may use to perform electrical defibrillation when emergency situations arise. AEDs may be found in a variety of non-medical settings, including residences, public buildings, businesses, private vehicles, public transportation vehicles, and airplanes.

An AED relies upon a set of electrodes to deliver a series of shocks to a patient. An electrode therefore serves as a physical and electrical interface between the AED and the patient's body. In general, an electrode may comprise a conductive foil layer that resides upon a conductive adhesive layer; a lead wire that couples the foil layer to the AED; and an insulating layer that covers the foil layer. The conductive adhesive layer physically and electrically interfaces the foil layer to a patient's skin. New or unused electrodes reside upon a release liner, from which an operator may peel off an electrode prior to placement upon a patient's body. During manufacture, electrodes upon their release liner are typically sealed in a package.

An AED is likely to be used infrequently; however, any given use may involve a time critical, life threatening situation. Thus, it is imperative that the AED be able to provide an indication of its operating condition at essentially any time. While in a quiescent state, an AED generally performs periodic diagnostic sequences to determine its current operating condition. Such sequences may be performed, for example, on a daily and/or weekly basis. The diagnostic sequences include tests for characterizing the current path between the AED and a set of electrodes. Hence, the electrodes must be connected to the AED while the AED is in its quiescent state, and the electrodes must be electrically testable while mounted on their release liner. As a result, release liners providing electrical contact between electrodes have been developed.

Such release liners generally include multiple openings that facilitate electrical contact between electrodes. The current path between the AED and the electrodes includes each electrode's lead wire, foil layer, and conductive adhesive layer. For a pair of new, properly functioning conventional electrodes mounted upon a release liner having multiple openings, this current path may be characterized by an impedance value ranging between 2 and 10 Ohms. If an impedance measurement indicates an electrical discontinuity or open circuit condition exists, a lead wire or connector coupling an electrode to the AED may be damaged, and/or an electrode may be improperly connected to the AED. Similarly, if an impedance measurement indicates a short or open circuit condition exists, one or more electrodes, a lead wire or other wire within the current path, and/or a connector that couples the electrodes to the AED may be damaged or defective.

A measurement indicating a higher than desired impedance may arise when an electrode is damaged, deteriorated, and/or degraded. An electrode's conductive adhesive layer typically comprises a hydrogel film, which itself comprises natural and/or synthetic polymers dispersed or distributed in an aqueous fluid. The electrical properties of the hydrogel film are dependent upon its moisture content. If the hydrogel possesses appropriate water content, it provides a low impedance electrical path between the electrode's foil layer and a patient's skin. The hydrogel film, however, dries out over time. As a result, its impedance increases over time, thereby undesirably decreasing its effectiveness for signal exchange and energy transfer between a patient and an AED. Once moisture loss has reached a certain level, the hydrogel film, and hence the electrode of which it forms a part, may be unsuitable for use.

A patient's transthoracic impedance typically falls within a range of 25 to 200 Ohms. As electrodes' hydrogel film deteriorate over time, the impedance associated with the electrical path provided by the electrodes may overlap with the typical transthoracic impedance range. Thus, if an AED in a normal operational or "on" state measures an electrode impedance corresponding to a patient's transthoracic impedance, the AED has no inherent way of determining whether partially deteriorated electrodes are currently mounted upon their release liner, or properly functioning electrodes are connected to the patient.

Prior release liners that facilitate electrical testing of electrodes mounted thereupon have typically been unnecessarily complex, expensive to manufacture, unacceptable relative to difficulty of electrode removal, and/or limited relative to the extent to which they permit accurate characterization of an electrode's hydrogel film. A need exists for electrodes and/or release liners that overcome the aforementioned deficiencies.

SUMMARY OF THE INVENTION

The present invention includes a number of release liner, electrode, and/or medical or measuring device embodiments that facilitate electrical characterization of one or more electrodes coupled to the medical or measuring device. In the context of the present invention, a medical device may be essentially any device capable of using electrodes to receive signals from and/or deliver signals and/or energy to a patient's body. A measuring device may be essentially any device capable of electrically characterizing packaged electrodes.

In one embodiment, a release liner comprises a release layer and a moisture-permeable and/or moisture-absorbent membrane or sheet. The release layer may include an opening therein, over which the membrane may reside. When electrodes are positioned or mounted upon the release liner, the electrodes' conductive adhesive or hydrogel layers may transfer moisture to the membrane, thereby forming a low impedance electrical path that facilitates electrical communication between electrodes. The membrane may be prewetted or premoistened prior to mounting electrodes upon the release layer to minimize electrode moisture loss.

The release layer may comprise a single, foldable sheet that surrounds or partially surrounds the membrane. A pair of electrodes residing upon the same side of the foldable sheet may exchange electrical signals. Alternatively, a first and a second release layer may encase or enclose one or more portions of the membrane, where each release layer includes an opening. In another release liner embodiment, a membrane may extend beyond a border of a single release layer that lacks openings. Electrodes mounted upon the release layer in such an embodiment also extend beyond the release layer border, and contact the membrane to facilitate electrical communication therebetween.

A release liner and electrode package according to an embodiment of the invention may comprise a rigid cartridge having an electrical interface incorporated therein; a release liner having a set of openings therein; and a set of electrodes mounted upon the release liner. The openings in the release liner facilitate electrical communication between electrodes. The rigid cartridge provides an environment characterized by well-defined internal conditions, where moisture transfer in or out of the rigid cartridge is minimal or essentially eliminated. Such a package may therefore prolong electrode lifetime.

A release liner according to another embodiment of the invention may comprise a release layer upon which a conductive strip resides. Electrodes may be mounted in a side-by-side manner upon the release layer, and may exchange electrical signals via the conductive strip. The release layer may comprise a foldable sheet. In an alternate embodiment, the conductive strip may wrap around or encircle the release layer, facilitating electrical communication between electrodes mounted on opposite sides of the release layer.

A release liner according to another embodiment of the invention may comprise a release layer having a set of openings therein, and a conductive backing layer. The release layer may comprise a foldable sheet. Electrodes may be mounted upon such a release liner in a side by side manner. An electrical signal may travel from one electrode, through an opening in the release layer, through or within the conductive backing layer, through another opening in the release layer, and into another electrode.

The conductive backing layer may comprise a metal, or a conductive adhesive layer such as a hydrogel layer. In the event that the conductive backing layer comprises a conductive adhesive layer, an electrical current traveling between mounted electrodes may follow a path that is much greater than the thickness of the electrodes' conductive adhesive layers. As a result, the measured impedance of the release liner may be greater than typical patient impedance ranges, and may exhibit a high degree of sensitivity to conductive adhesive layer degradation over time.

A release liner according to another embodiment of the invention may comprise a first release layer or sheet, a second release layer or sheet, and an intervening conductive adhesive layer. The first and second release layers each include an opening. The first and second release layers are oriented or positioned such that their openings are offset relative to each other by a separation distance. Electrodes mounted upon the release layers may exchange electrical signals with each other via the release layer openings and the conductive adhesive layer between the release layers. Such electrical signals may travel through a length of conductive adhesive layer that is much greater than the thickness of the electrodes' conductive adhesive layers, in a manner analogous to that described above. In an alternate embodiment, a release liner may comprise a foldable sheet that surrounds or encases one or more portions of a conductive adhesive or hydrogel layer. The foldable sheet may include openings, which are offset relative to each other in accordance with a given separation distance when the foldable sheet surrounds or encases portions of the conductive adhesive layer.

An electrode according to an embodiment of the invention may comprise a conductive adhesive layer coupled to a conductive foil layer that includes one or more voids therein. Each void affects electrical current flow through the electrode's conductive adhesive layer when the electrode is mounted upon a release liner that facilitates electrical communication between electrodes. In particular, the presence of a void may cause transverse electrical current flow through the electrode's conductive adhesive layer, rather than simply current flow through the conductive adhesive layer's thickness. This results in a longer electrical path, which in turn may provide the voided electrode with an impedance that is greater than typical patient impedance levels. Additionally, impedance measurements along this electrical path may exhibit a significant degree of sensitivity to changes in conductive adhesive layer properties over time.

An electrode may include or incorporate one or more insulating swatches between its conductive foil layer and conductive adhesive layers. When the electrode is mounted upon a release liner that facilitates electrical communication between electrodes, the presence of an insulating swatch may result in transverse current flow through the electrode's conductive adhesive layer in a manner analogous to that described above for the voided electrode.

An electrode according to another embodiment of the invention may comprise a conductive foil layer, a conductive adhesive layer, and a sonomicrometer or ultrasonic transducer. When electrodes that incorporate ultrasonic transducers are mounted upon a release liner, ultrasonic signals transmitted and/or received via the ultrasonic transducers may be used to indicate an electrode separation distance. The electrode separation distance may indicate whether electrodes are mounted upon a release liner or a patient's body.

In accordance with the present invention, various types of electrodes may be mounted upon release liners that facilitate exchange of electrical signals between electrodes. A medical device to which such electrodes are coupled may perform a variety of measurements to characterize electrode condition or fitness for use. The medical device may measure a short or open circuit condition, which may indicate an electrical path problem. As one or more electrodes' conductive adhesive layers degrade over time, the medical device may measure increasing impedance levels. If an impedance level exceeds a given threshold value or range, the medical device may provide an indication that the electrodes are non-optimal or until for use. The medical device may alternately or additionally provide an indication of electrode condition or fitness for use at particular times or time intervals. The medical device may further calculate or determine a time remaining before an electrode or electrode pair may no longer be fit for use. Such a calculation or determination may be based upon a current degradation curve.

In accordance with an embodiment of the invention, a release liner that lacks openings may serve as a capacitive medium between electrodes mounted thereupon. A medical device may perform a capacitance measurement to electrically characterize an electrical path corresponding to the electrodes and release liner.

In accordance with another embodiment of the invention, a release liner may comprise a release layer that includes an opening, and an insulating swatch or patch that covers or resides within the opening. Electrodes may be mounted upon the release layer such that the electrodes' conductive adhesive layers cover the opening, and at least one electrode's conductive adhesive layer covers the swatch.

A medical device may perform a complex impedance measurement upon electrodes mounted upon a release liner having such a swatch. When one or more such electrodes include a void or internal swatch as described above, the result of the complex impedance measurement may exhibit significant dependence upon the current condition of such electrodes' conductive adhesive layers. The medical device may therefore determine an extent to which one or more electrodes are fit for use. The medical device may further provide a visual and/or other indication of electrode condition and/or fitness for use.

A medical device such as an Automated External Defibrillator (AED) may include or incorporate elements for periodically determining electrode condition or status. The medical device may include a status measurement unit, which may operate in conjunction with an electrode condition indicator, a display device, a speaker, and/or other elements in a variety of manners to indicate electrode condition, fitness for use, and/or an estimated remaining electrode lifetime. In accordance with an embodiment of the invention, an electrode condition indicator may incorporate, generate, and/or present one or more types of visual metaphors that provide an indication of electrode status, condition, and/or estimated remaining lifetime. A visual metaphor may correspond to a fuel gauge, and may convey positional and/or color relationships between one or more indicating elements that change or vary over time in accordance with measured and/or estimated electrode properties. The visual metaphor may further convey textual and/or symbolic information.

DESCRIPTION OF THE PREFERRED EMBODIMENTS

Figure 1A:
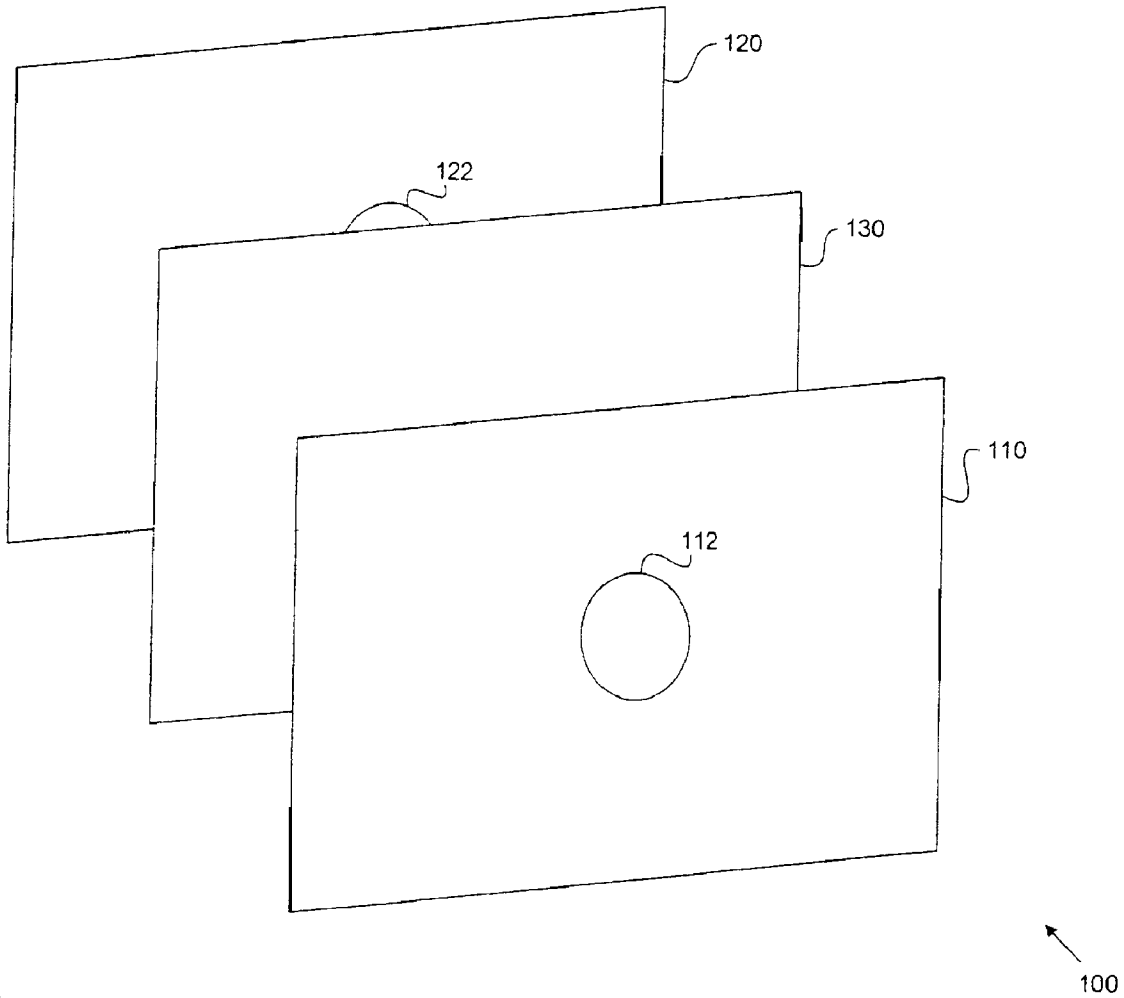
FIG. 1A is a layered perspective view of a release liner according to an embodiment of the invention.
Figure 1B:
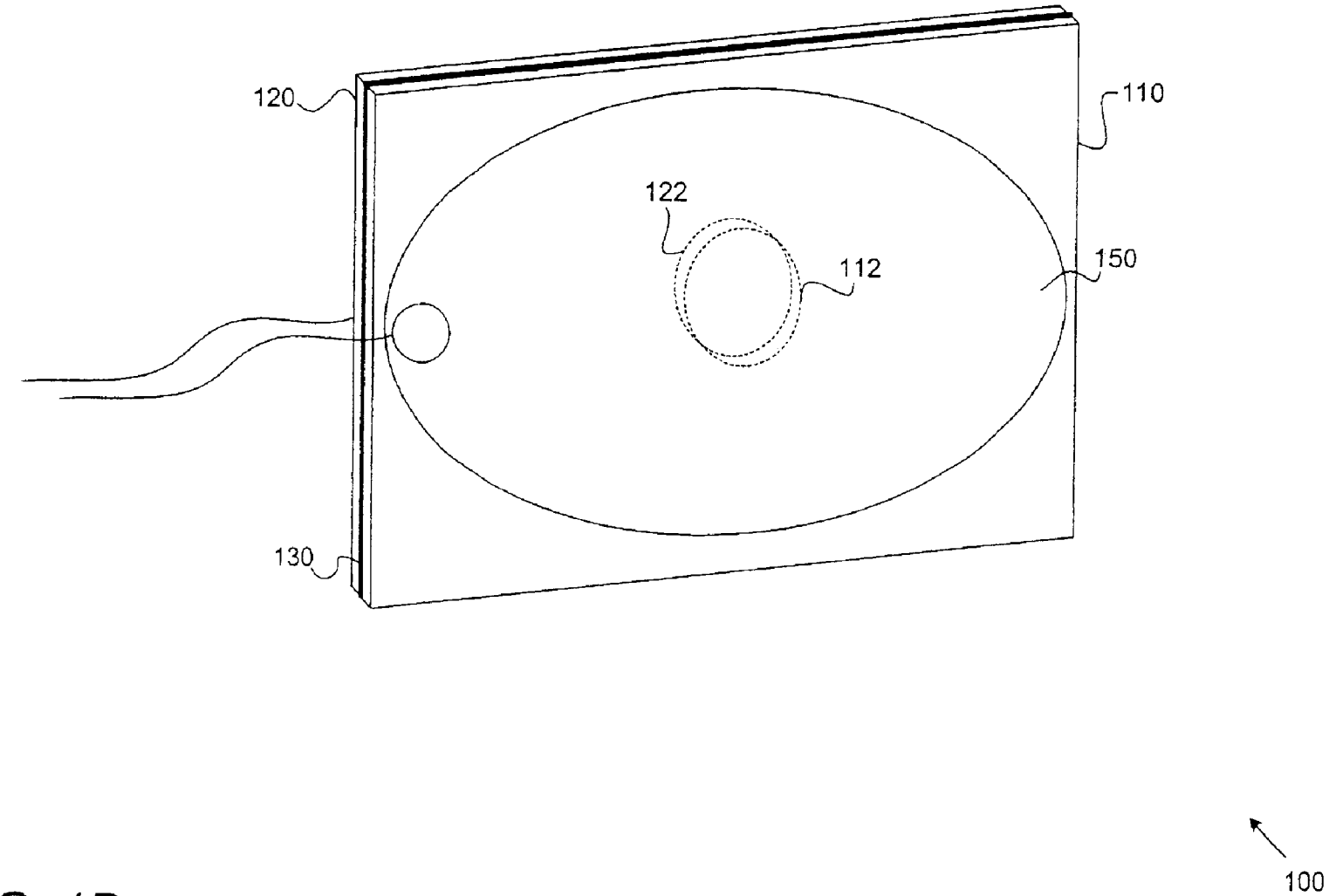
FIG. 1B is a perspective view of electrodes mounted upon the release liner of FIG. 1A.

The following discussion is presented to enable a person skilled in the art to make and use the invention. The general principles described herein may be applied to embodiments and applications other than those detailed below without departing from the spirit and scope of the present invention as defined by the appended claims. The present invention is not intended to be limited to the embodiments shown, but is to be accorded the widest scope consistent with the principles and features disclosed herein.

The present invention encompasses a wide variety of release liner and/or electrode embodiments that facilitate automatic electrical characterization of one or more packaged electrodes coupled to a medical or measuring device. In the context of the present invention, a medical device may be essentially any type of device capable of employing a set of electrodes to exchange signals with a patient. For example, the medical device may be a defibrillator; a cardiac pacing system; an electrocardiograph (ECG) or patient monitoring system; or an electrosurgery device. Since electrode fitness is of particular concern in relation to medical devices designed to provide emergency resuscitation capabilities, the description herein most commonly considers release liners and/or electrodes suitable for deployment with defibrillators, particularly Automated External Defibrillators (AEDs).

Relative to the present invention, a measuring device may be essentially any type of device capable of performing electrical measurements upon electrodes designed and/or packaged or mounted upon a release liner in accordance with the present invention. A measuring device need not include patient monitoring and/or treatment elements, but may comprise, for example, a power supply and a multimeter. Alternatively, a measuring device may comprise an LCR meter. Portions of the description herein that refer to packaged electrode characterization via a medical device may apply equally to packaged electrode characterization via a measuring device.

With respect to any or essentially any of the electrode and/or release liner embodiments described herein, a medical or measuring device may perform electrical characterization measurements and/or tests via conductive pathways, lead wires, and/or connectors associated with normal electrode configurations and/or normal electrode use. That is, the electrode and/or release liner embodiments detailed herein may require no additional couplings to a medical or measuring device beyond those that facilitate normal signal exchange between a patient and a medical device.

In accordance with the present invention, a medical or measuring device may include temperature measurement and/or compensation circuitry or elements to account and/or compensate for the effects of temperature variations upon the measured values of electrical parameters. A medical or measuring device may adjust electrical measurement and/or test parameters or criteria based upon one or more temperature measurements to facilitate temperature compensated characterization of electrodes mounted upon a release liner. Temperature compensation capabilities may be of particular value in medical or measuring devices that perform impedance measurements such as those described in detail below.

A medical device operating in accordance with the present invention may also include impedance compensation circuitry, such as that described in U.S. Pat. No. 6,047,212, entitled "External Defibrillator Capable of Delivering Patient Impedance Compensated Biphasic Waveforms," which is incorporated herein by reference.

As described in detail below, a medical or measuring device may perform one or more types of measurements upon electrodes mounted upon a release liner. The medical or measuring device may perform in-situ measurements at various intervals over time, and provide an indication of current electrode condition and/or estimated remaining lifetime based upon such measurements. As a result, in contrast to the prior art, packaged electrodes designed and/or deployed in accordance with the present invention may not require associated markings or other information to define or specify an expiration date or shelf life.

Packaged electrodes designed and/or deployed in accordance with the present invention may include a wrapper, covering, label or the like that includes an "install by" date that specifies a date by which electrodes should be installed upon or coupled to a medical or measuring device. The wrapper may be removed to facilitate installation, after which the medical or measuring device may determine when electrode replacement is required based upon electrical measurements.

FIG. 1A is a layered perspective view of a release liner 100 according to an embodiment of the invention. In one embodiment, the release liner 100 comprises a first release layer or sheet 110; a second release layer or sheet 120; and a moisture-permeable membrane 130. The first release layer 110 includes one or more openings 112 disposed therein. Similarly, the second release layer 120 includes one or more openings 122, which may positionally correspond to those in the first release layer 110.

Each release layer 110, 120 may comprise a nonconductive sheet having non-stick properties. A given release layer 110, 120 may comprise silicon-coated paper, polyester, polypropylene, polyethylene, and/or other non-stick materials, in a manner well understood by those skilled in the art. The openings 112, 122 in each release layer 110, 120 may be cut, stamped, or punched out using conventional techniques.

The moisture-permeable membrane 130 may comprise a nonconductive, moisture-permeable and/or moisture-absorbent material, such as litmus paper, that resides between the first and second release layers 110, 120. While the moisture-permeable membrane 130 is depicted in FIG. 1A as spanning an area approximately equal to that of the first and second release layers 110, 120, the moisture-permeable membrane 130 may be smaller, subject to the requirement that it cover openings 112, 122 in the first and second release layers 110, 120. Depending upon embodiment and/or implementation details, the moisture-permeable membrane 130 may be adhered, bonded, laminated, and/or otherwise attached to one, both, or neither release layer 110, 120, as further detailed hereafter.

In one embodiment, the release liner 100 may be manufactured such that the moisture-permeable membrane 130 is bonded, adhered, laminated, and/or otherwise attached to an inside surface of first release layer 110. The second release layer 120 may be oriented or positioned such that its openings 122 are essentially coincident with the set of openings 112 in the first release layer 110. Following any required positioning, the second release layer 120 may be bonded, adhered, laminated, and/or otherwise attached to the moisture-permeable membrane 130 in a manner similar to that for the first release layer 110.

FIG. 113 is a perspective view of electrodes 150 mounted upon the release liner 100 of FIG. 1A. In one embodiment, each electrode 150 may be conventional, and comprises a conductive foil layer that resides upon a conductive adhesive layer. The conductive adhesive layer may comprise a conductive gel layer, such as a hydrogel layer, in a manner well understood by those skilled in the art. In general, the electrical properties of the conductive adhesive layer may degrade over time, which may occur as a result of moisture loss, solvent loss, cross-linking, or other factors. In the description that follows, the conductive adhesive layer will be taken to be a hydrogel layer for ease of understanding. The principles herein may be applied to essentially any type of electrode that incorporates essentially any type of conductive adhesive or other layer having electrical properties that degrade over time.

Those skilled in the art will understand that electrical current may flow from an electrode's foil layer through the thickness of the electrode's hydrogel layer. In general, an electrode's hydrogel layer may exhibit a thickness of 25 to 50 mils. The electrode 150 may further comprise an insulating cover layer, as well as a lead wire that facilitates coupling to a connector or medical device.

One electrode 150 may be placed or positioned upon the first release layer 110 such that the electrode's hydrogel layer covers one or more of the openings 112 in the release layer 110. Another electrode 150 may be placed or positioned upon the second release layer 120 in an analogous manner. Placement of electrodes 150 upon the release liner 100 in the manner depicted allows the electrodes' hydrogel layers to contact the moisture-permeable membrane 130 via the openings 112, 122 in the release layers 110, 120.

Initially, the moisture-permeable membrane 130 may be dry or essentially moisture free throughout one or more bonding, adhesion, lamination, and/or attachment procedures performed during release liner manufacture. In the event that the moisture-permeable membrane 130 remains dry during release liner manufacture, the openings 112, 122 in each release layer 110, 120 may ensure that placement of electrodes 150 upon the release liner 100 results in moisture transfer from each electrode's hydrogel layer into the moisture-permeable membrane 130. After a period of time, this moisture transfer results in low impedance electrical pathways through the thickness of a given electrode's hydrogel layer, the moisture-permeable membrane 130, and the thickness of the other electrode's hydrogel layer in regions defined by the release layer openings 112, 122.

When the electrodes 150 are coupled to a medical or measuring device (not shown), the medical device may measure and/or characterize the electrical pathways between the electrodes' hydrogel layers and the moisture-permeable membrane 130. As each electrode's hydrogel layer loses moisture over time, measured impedance increases. Once the measured impedance has reached or surpassed a predetermined value, the electrodes may no longer be in optimal condition, or may be unfit for use. The medical device may provide an indication of electrode status and/or electrode life remaining, and/or indicate that electrode replacement is required, in manners described in detail below.

Placement of electrodes 150 on a release liner 100 having a dry or essentially dry moisture-permeable membrane 130 contributes to hydrogel moisture loss. To prevent or minimize such moisture loss, the moisture-permeable membrane 130 may be prewetted or premoistened in a variety of manners, such as via placement in a high-humidity environment (e.g., 50-100% relative humidity) until it has absorbed sufficient moisture to exhibit a low impedance value. When residing between the first and second release layers 110, 120 prior to electrode placement, the moisture-permeable membrane's impedance may be measured or tested via a set of probes that contact the moisture-permeable membrane 130 through first and second release layers' openings, in a manner well understood by those skilled in the art. The moisture-permeable membrane 130 may alternatively or additionally be moistened using a wet cloth or sponge, or placed in a liquid bath.

Depending upon embodiment and/or implementation details, the moisture-permeable membrane 130 may be bonded, adhered, laminated, and/or otherwise attached to the first release layer 110 but not the second release layer 120. In such a situation, the adhesion between the hydrogel of an electrode 150 placed upon the second release layer 120 and the moisture-permeable membrane 130 will generally be sufficient to maintain the second release layer 120 in an appropriate position upon the moisture-permeable membrane 130.

Alternatively, bonding, adhering, laminating, or other moisture-permeable membrane attachment procedures may be omitted for both the first and second release layers 110, 120. In such an embodiment, the moisture-permeable membrane 130 is simply placed or situated between the first and second release layers 110, 120, after which electrodes 150 are placed or positioned upon the first and second release layers 110, 120. In the areas defined by the first and second release layers' openings 112, 122, the adhesion between the electrodes' hydrogel layers and the moisture-permeable membrane 130 may be sufficient to appropriately maintain the position of each release layer 110, 120 relative to the moisture-permeable membrane 130. Such an embodiment can simplify manufacturing processes and reduce production costs.

Figure 1C:
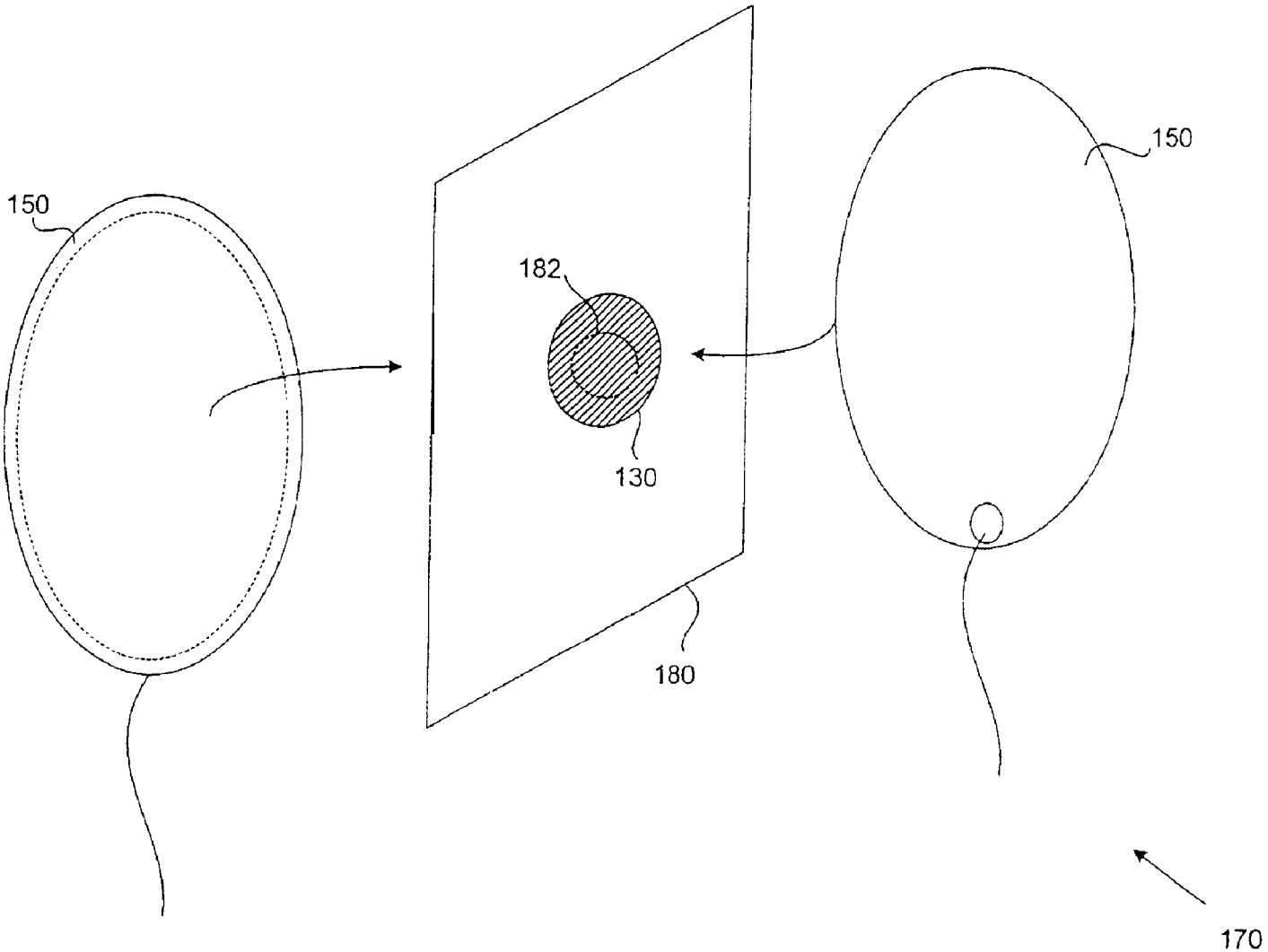
FIG. 1C is a perspective view of a release liner according to another embodiment of the invention, and a manner of mounting electrodes thereupon.

FIG. 1C is a perspective view of a release liner 170 according to another embodiment of the invention, and a manner of mounting electrodes 150 thereupon. Relative to FIG. 1A, like reference numbers indicate like elements to aid understanding. In one embodiment, the release liner 170 comprises a single release layer 180 having an opening 182 therein, and a moisture-permeable and/or moisture-absorbent membrane 130 covering the opening 182. The moisture permeable membrane 130 may be bonded, adhered, stitched, and/or otherwise attached to the release layer 180. In an exemplary embodiment, the moisture-permeable membrane may be heat bonded or ultrasonically bonded to the release liner 170.

One electrode 150 may be placed or positioned upon the release layer 180 such that the electrode's hydrogel layer covers the release layer's opening 182. Another electrode 150 may be placed or positioned upon the release layer 180 in an analogous manner. Placement of electrodes 150 upon the release layer 180 allows the electrodes' hydrogel layers to contact the moisture-permeable membrane 130 via the release layer's opening 182. In the event that the moisture-permeable membrane 130 is dry or essentially moisture free prior to placement of electrodes upon the release layer 180, moisture transfer from each electrode's hydrogel layer may occur. After a period of time, such moisture transfer results in a low impedance electrical pathway between each electrode's hydrogel layer and the moisture-permeable membrane 130. The moisture permeable membrane 130 may be premoistened or prewetted as described above to minimize moisture loss from electrodes' hydrogel layers.

When the electrodes 150 are coupled to a medical or measuring device (not shown), the medical device may measure and/or characterize the electrical pathways between the electrodes' hydrogel layers and the moisture-permeable membrane 130 in a manner analogous to that described above.

Figure 2A:
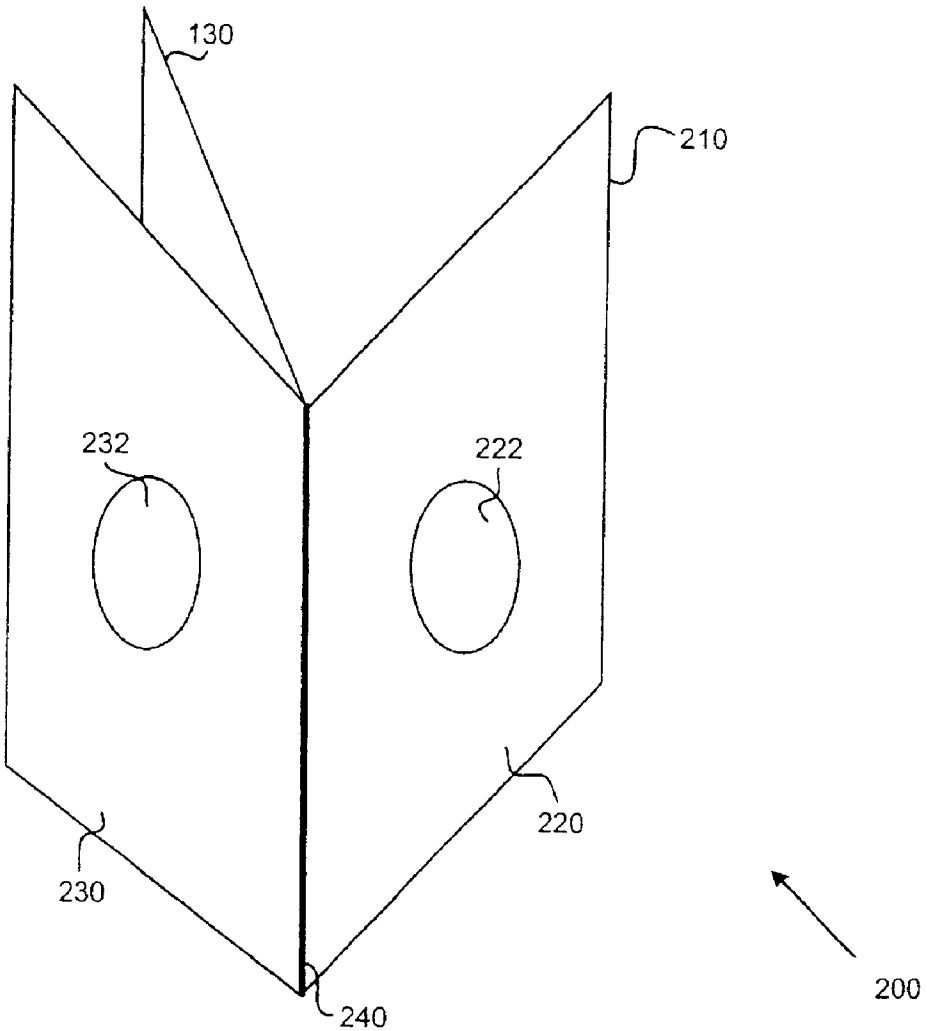
FIG. 2A is a perspective view of a release liner according to another embodiment of the invention.

FIG. 2A is a perspective view of a release liner 200 according to another embodiment of the invention. Relative to FIG. 1A, like reference numbers indicate like elements to aid understanding. In one embodiment, the release liner 200 comprises a foldable release layer or sheet 210 and a moisture-permeable membrane 130. The foldable release layer 210 comprises a first mounting or release portion, region, or segment 220 having at least one opening 222 therein; a second mounting or release portion, region, or segment 230 having at least one opening 232 therein; and a fold region 240. In one embodiment, the openings 222, 232 in the first and second mounting portions 220, 230 are formed in corresponding positions relative to the fold region 240, such that when the foldable release layer 210 is folded, bent, or doubled about the fold region 240, the openings 222, 232 are essentially coincident.

The foldable release layer 210 may comprise a nonconductive sheet having non-stick properties, and may be formed using silicon-coated paper, polyester, polypropylene, polyethylene, and/or other non-stick materials, in a manner well understood by those skilled in the art. The openings 222, 232 in the first and second mounting sections 220, 230 may be cut, stamped, or punched out using conventional techniques.

The moisture-permeable membrane 130 may comprise a nonconductive, moisture-permeable and/or moisture-absorbent material, in a manner analogous to that described above with reference to FIG. 1A. The moisture-permeable membrane 130 may cover an area less than that of the first and/or second mounting portions 220, 230, subject to the requirement that it cover or span openings 222, 232 in each mounting portion 220, 230 when the foldable release layer 210 is folded. Depending upon embodiment and/or implementation details, the moisture-permeable membrane 130 may be adhered, bonded, laminated, and/or otherwise attached to one, both, or neither of the first and second mounting sections 220, 230.

The foldable release layer 210 may be folded, bent, or doubled about the fold region 240 in either direction to surround or encase one or more portions of the moisture-permeable membrane 130. When folded in such a manner, the moisture-permeable membrane 130 is exposed in the regions defined by the openings 222, 232 in the first and second mounting portions 220, 230.

Figure 2B:
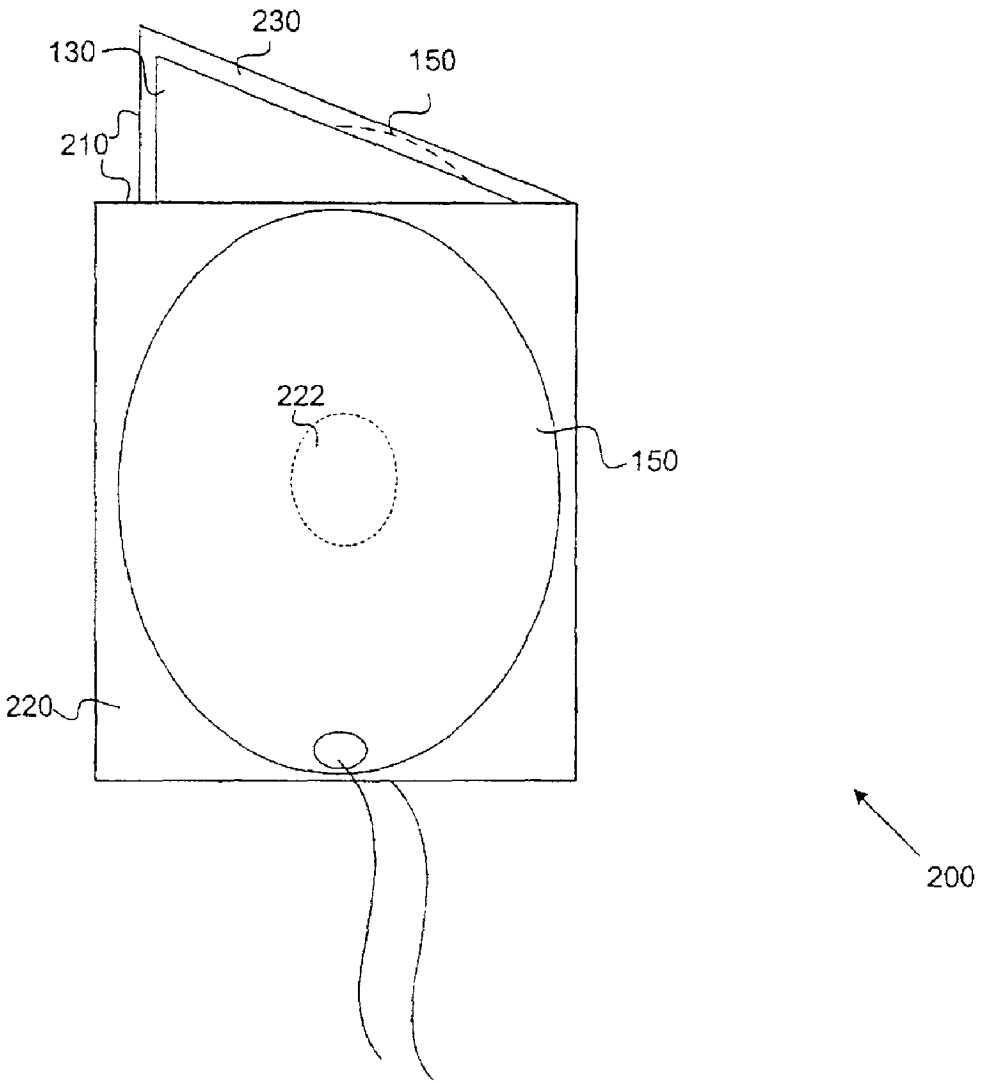
FIG. 2B is a perspective view of electrodes mounted upon the release liner of FIG. 2A.

FIG. 2B is a perspective view of electrodes 150 mounted upon the release liner 200 of FIG. 2A. One electrode 150 may be positioned or situated upon an outer surface of the first mounting portion 220, while another electrode 150 may be positioned upon an outer surface of the second mounting portion 230. The outer surfaces of the first and second mounting portions 220, 230 together form a single outer surface of the foldable release layer 210. Thus, both electrodes 150 are mounted upon the same side or surface of the foldable release liner 210.

In the description herein, release liner mounting portions 220, 230, such as those described in relation to the release liner 200 of FIGS. 2A and 2B, provide regions or areas upon which electrodes 150 may reside. Electrodes 150 may be readily removed or peeled off of the mounting portions 220, 230, as the mounting portions 220, 230 comprise non-stick or generally non-stick portions of the release liner 200.

As with the release liner 100 of FIG. 1A, the moisture-permeable membrane 139 may remain dry or essentially moisture free during release liner manufacture or assembly. In such a situation, a low impedance electrical path may form after electrodes 150 are placed upon the foldable release layer 210 and the electrodes' hydrogel layers transfer moisture into the moisture-permeable membrane 130 in the regions defined by the openings 222, 232 in the first and second mounting portions 220, 230. Alternatively, the moisture-permeable membrane 130 may be prewetted or premoistened in the manners described above to help minimize hydrogel moisture loss.

Once electrodes 150 are mounted or positioned upon the release liner 200 of FIG. 2A, a medical device to which the electrodes are coupled may test or characterize the electrical path through one electrode's hydrogel layer, the moisture-permeable membrane 130, and the other electrode's hydrogel layer. As a hydrogel layer loses moisture over time, the medical device may correspondingly measure increasing impedance levels. An impedance value exceeding a given threshold may indicate that the electrodes 150 are not optimally fit for use, or that the electrodes 150 are unsuitable for use and should be replaced. The medical device may provide an indication of electrode status and/or remaining electrode life, and/or recommend electrode replacement, in manners described in detail below.

Figure 3A:
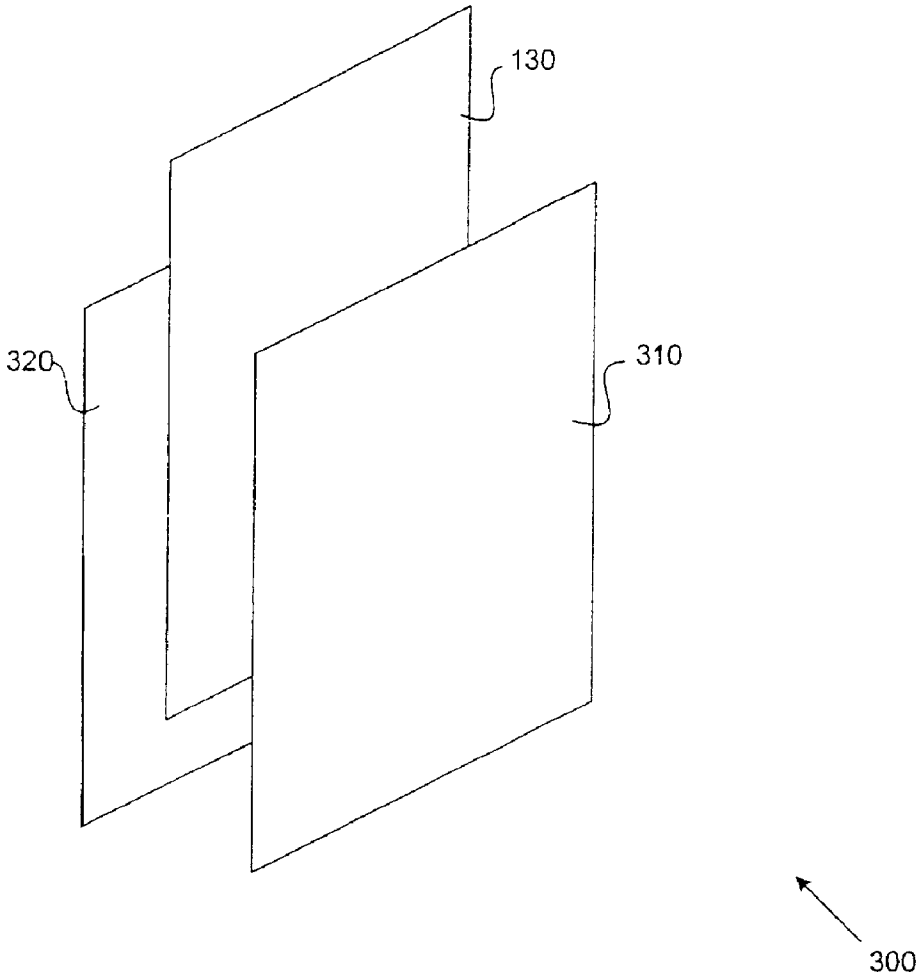
FIG. 3A is a layered perspective view of a release liner according to another embodiment of the invention.

FIG. 3A is a layered perspective view of a release liner 300 according to another embodiment of the invention. Relative to FIG. 1A, like reference elements indicate like elements to aid understanding. The release liner 300 may comprise a first release layer or sheet 310; a second release layer or sheet 320; and a moisture-permeable membrane 130. In contrast to the release liner 100 of FIG. 1A, openings 112, 122 may not be present in the release layers 310, 320 of the release liner 300 of FIG. 3A.

Each release layer 310, 320 may comprise a nonconductive sheet having non-stick properties, and may be implemented using silicon-coated paper, polyester, polypropylene, polyethylene, and/or other non-stick materials, in a manner well understood by those skilled in the art. The moisture-permeable membrane 130 may comprise a non-conductive, moisture-permeable material in the manner described above, which resides between the first and second release layers 310, 320.

Portions of the moisture-permeable membrane reside between the release layers 310, 320. In one embodiment, the moisture-permeable membrane 130 overlaps or extends beyond at least one release layer edge or border. Depending upon embodiment and/or implementation details, the moisture-permeable membrane 130 may be adhered, bonded, laminated, and/or otherwise attached to one, both, or neither release layer 310, 320, in a manner analogous to that described above with reference to FIG. 1A.

Figure 3B:
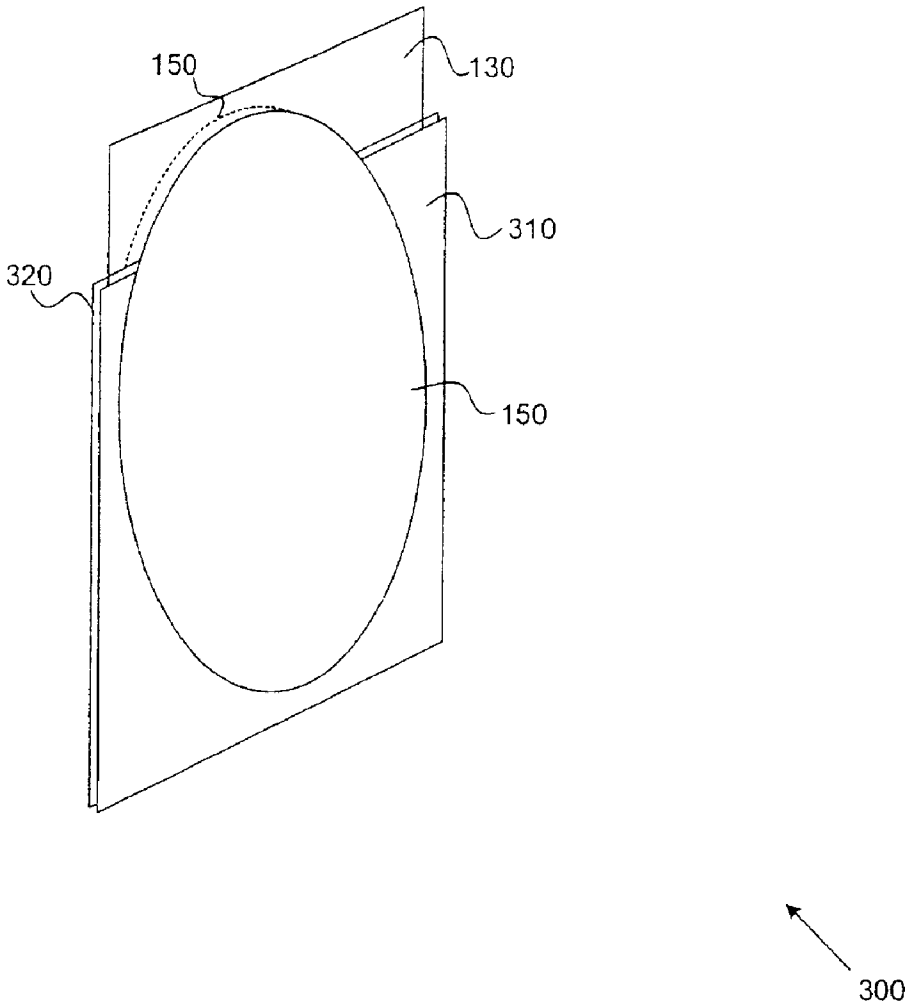
FIG. 3B is a perspective view of electrodes mounted upon the release liner of FIG. 3A.

FIG. 3B is a perspective view showing electrodes 150 mounted upon the release liner 300 of FIG. 3A. In the embodiment shown, the electrodes' hydrogel layers 150 contact one or more portions of the moisture-permeable membrane 130 in areas in which the moisture-permeable membrane 130 overlaps or extends beyond release layer boundaries. Thus, portions of the electrodes 150 extend beyond or overlap one or more release layer edges, boundaries, and/or borders. Therefore, the release layers 310, 320 in such an embodiment may be appropriately sized or scaled relative to the size of the electrodes 150 to facilitate such contact.

As shown in FIG. 3B, portions of the electrodes' hydrogel layers contact the moisture-permeable membrane 130. A low impedance electrical pathway through the thickness of each electrode's hydrogel layer and the moisture-permeable membrane 130 may arise following moisture transfer from hydrogel layers to the moisture-permeable membrane 130. Alternatively, the moisture-permeable membrane 130 may be prewetted or premoistened to facilitate a low impedance pathway while minimizing hydrogel moisture loss. As with the release liners 100, 200 described above, when electrodes 150 mounted upon the release liner 300 of FIG. 3A are coupled to a medical device, the medical device may measure increasing impedance levels over time as the electrodes' hydrogel layers lose moisture. Impedance levels greater than a given threshold or beyond a given range may indicate one or more electrodes 150 are non-optimal or unfit for use. A medical device may provide an indication of electrode condition in a variety of manners described in detail below.

In a manner analogous to that for the embodiments shown in FIG. 2A and FIG. 3A, a foldable release layer that lacks openings (not shown) may partially enclose or envelop a moisture-permeable membrane 130, such that the moisture-permeable membrane 130 extends beyond one or more edges of the foldable release layer when so enclosed. When an inner surface of such a foldable release layer surrounds or encases portions of a moisture-permeable membrane 130, electrodes 150 may be positioned on a common outer surface of the foldable release layer such that the electrodes' hydrogel layers contact exposed portions of the moisture-permeable membrane 130. This hydrogel to moisture-permeable membrane to hydrogel contact facilitates transfer of electrical signals between electrodes 150. As in embodiments described above, the moisture-permeable membrane 130 in such an embodiment may or may not be adhered, laminated, or otherwise attached to one or more segments or regions of the foldable release layer. Additionally, the moisture-permeable membrane 130 may be prewetted or premoistened to minimize moisture loss from each electrode's hydrogel layer.

Figure 4:
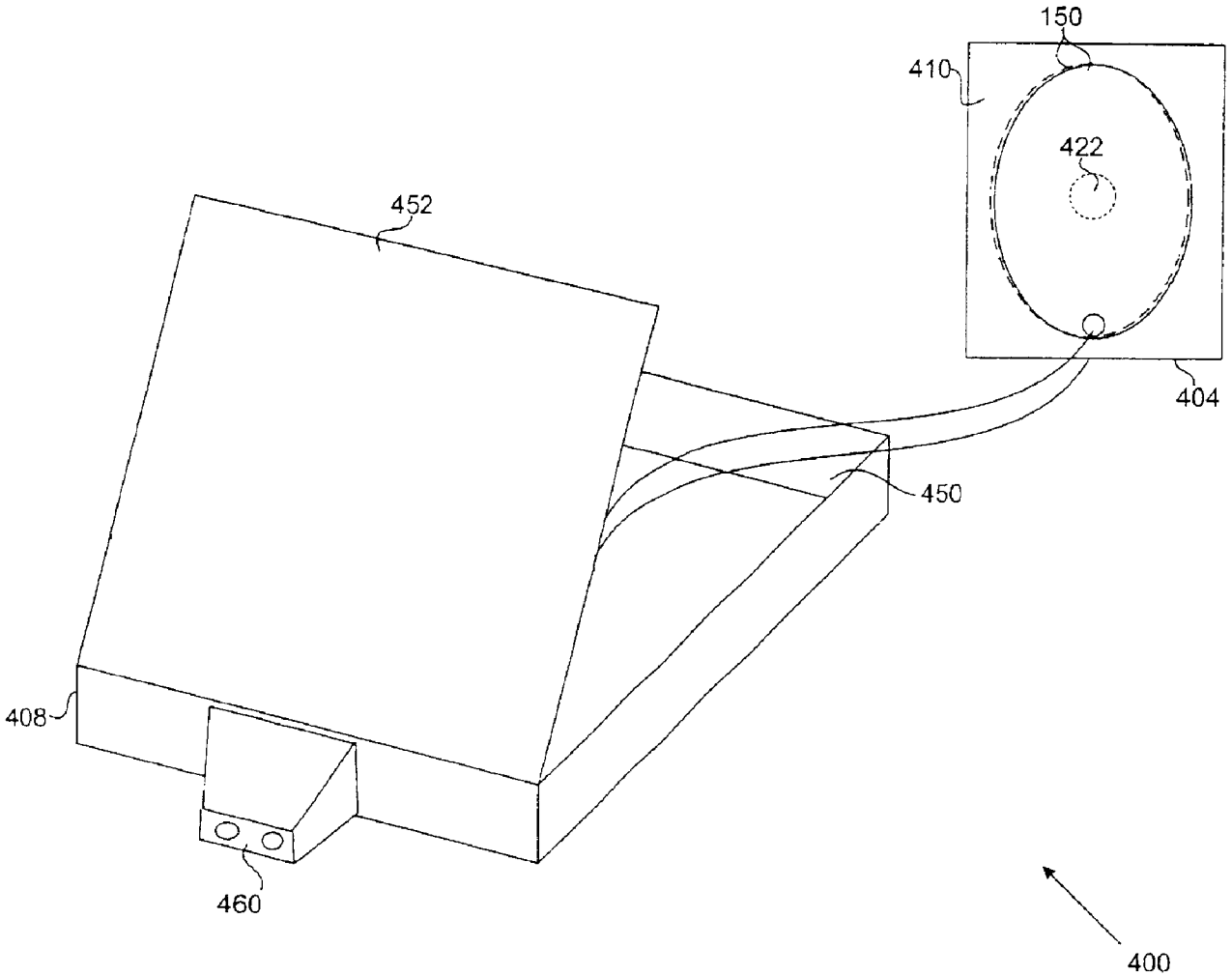
FIG. 4 is a perspective view of a release liner and an electrode package according to an embodiment of the invention.

FIG. 4 is a perspective view of a release liner and electrode package 400 according to an embodiment of the invention. The release liner and electrode package 400 may comprise a release liner 404, electrodes 150 mounted thereupon, and a rigid cartridge 408 in which a release liner 410 and mounted electrodes 150 may be stored prior to use. The release liner 404 may comprise a release layer 410 having an opening 422 therein. The release layer 410 may comprise a nonconductive, non-stick material such as those described above, and the opening 422 may be cut, stamped, or punched out of the release layer 410 via conventional techniques. One electrode 150 may be mounted or positioned upon one side of the release layer 410, while another electrode 150 may be mounted another side of the release layer 410, such that each electrode's hydrogel layer covers the release layer's opening 422. Such electrode mounting may result in hydrogel layer to hydrogel layer contact, thereby facilitating electrical communication between electrodes 150. In an alternate embodiment, the release layer 410 may include multiple openings 422, where mounted electrodes 150 may cover some or all of such openings 422.

The rigid cartridge 408 may comprise a housing or tray 450, a removable lid 452, and an electrical interface 460. The tray 450 and removable lid 452 may comprise plastic or another conventional material, and may store the mounted electrodes 150. The electrical interface 460 may comprise a connector that facilitates electrical coupling of the electrodes 150 to a medical device. In one embodiment, the rigid cartridge 408 may be implemented in a manner described in U.S. patent application Ser. No. 09/746,123, entitled CARTRIDGE FOR STORING AN ELECTRODE PAD AND METHODS FOR USING AND MAKING THE CARTRIDGE, filed on Dec. 22, 2000, which is incorporated by reference.

The rigid cartridge 408 facilitates high-reliability sealing of mounted electrodes 150 within an environment that may be characterized by well-defined conditions. In particular, via a conventional technique such as injection molding, the electrical interface 460 may be molded into the tray 450 such that when the lid 452 is sealed upon the tray 450, moisture transfer into or out of the rigid cartridge 408 is minimized, eliminated, or essentially eliminated. Storage of unused electrodes 150 within the rigid cartridge 408 may therefore extend electrode shelf life by slowing and/or minimizing moisture loss from the electrodes' hydrogel layers. The rigid cartridge 408 may additionally protect the electrodes 150 contained therein. Such protection may be necessary in the event that the medical device comprises an AED that is deployed or transported in real-world conditions, such as within law enforcement or rescue vehicles.

When electrodes 150 that have been mounted upon the release liner 404 and sealed within the rigid cartridge 408 are coupled to a medical device, the medical device may test and/or characterize the electrical path between the electrical interface 460, a given electrode's lead wire, the given electrode's conductive foil layer, the given electrode's hydrogel layer, through the release layer's opening 422, and through the other electrode's hydrogel layer, conductive foil layer, and lead wire back to the electrical interface 460. In the event that a short or open circuit condition exists, the electrical interface 460, a lead wire, and/or possibly one or both electrodes 150 may be damaged or defective. In the event that the medical device measures an impedance level or value that exceeds a predetermined threshold or range, the electrodes 150 may be non-optimal or unfit for use. The medical device may provide one or more indications of the condition of the aforementioned electrical path in a variety of manners, as described in detail below.

Figure 5A:
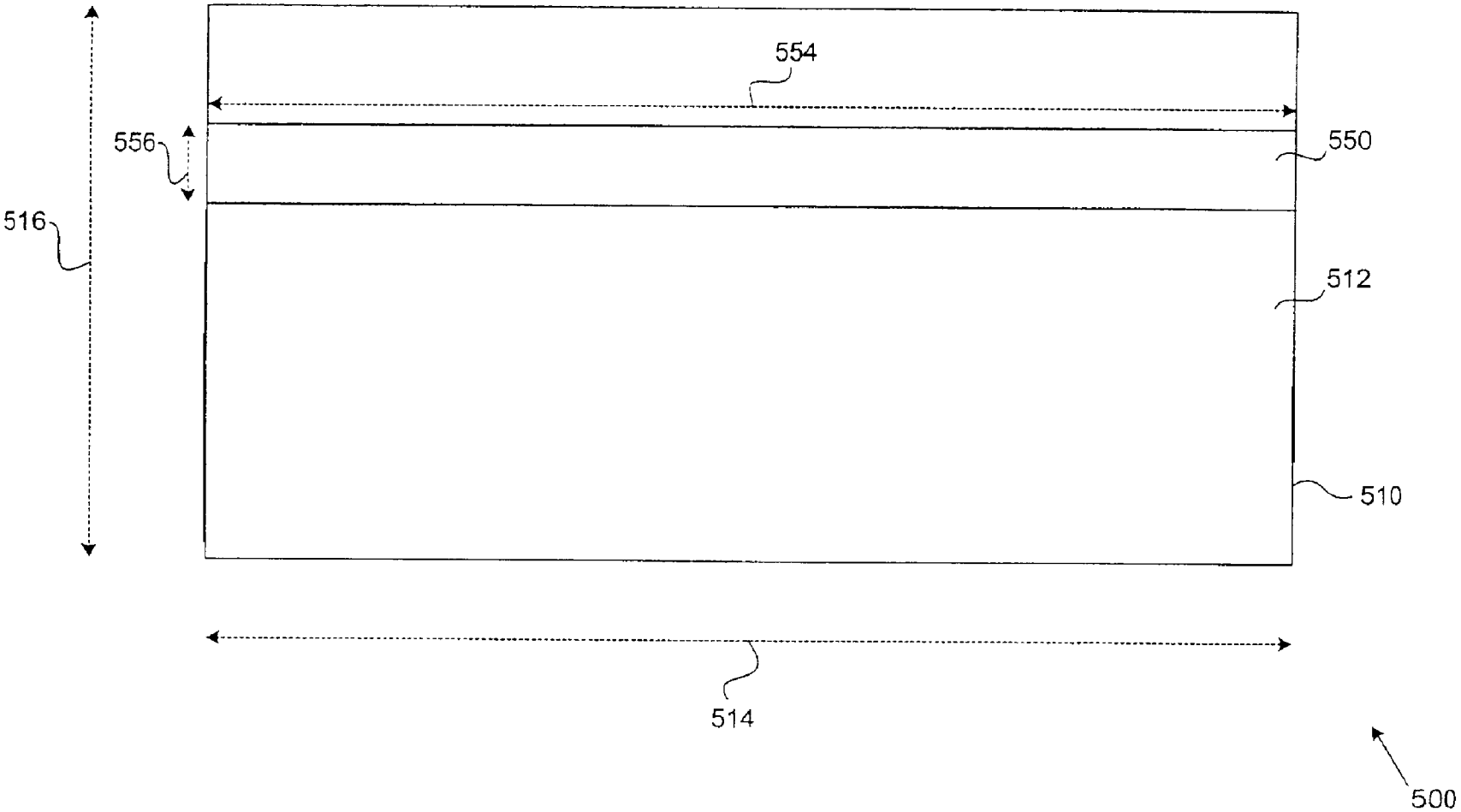
FIG. 5A is a plan view of a release liner according to another embodiment of the invention.

FIG. 5A is a perspective view of a release liner 500 according to another embodiment of the invention. The release liner 500 may comprise a single release layer or sheet 510; and a conductive strip 550 positioned, mounted, and/or affixed thereupon. In one embodiment, the release layer 510 may be characterized by a mounting surface 512, a length 514, and a width 516. The release layer 510 comprises a nonconductive sheet having non-stick properties, and may be implemented or fabricated using materials such as those described above with respect to other release liner embodiments. The conductive strip 550 may be characterized by a length 554 and a width 556, and comprises an electrically conductive material such as a metal foil (e.g., Aluminum or Tin), or an impregnated or sprayed-on metal layer.

In one embodiment, the conductive strip 550 resides upon the release layer's mounting surface 512. The conductive strip 550 may exhibit a wide range of lengths 554 and/or widths 556. In the embodiment shown, the conductive strip's length 554 is approximately equal to the length 514 of the release layer 510, while the conductive strip's width 556 spans a portion of the release layer's width 516. In general, the conductive strip 550 should be dimensioned to ensure 1) a reliable electrical pathway from one electrode 150 to another exists when the electrodes 150 are placed or mounted in a side-by-side manner upon the release layer 510; and 2) a sufficient portion of any given electrode's hydrogel layer resides upon the non-stick release layer 510, thereby facilitating easy removal of electrodes 150 from the release layer 510. Those skilled in the art will understand that the conductive strip's dimensions 554, 556 may be impacted by cost and/or manufacturability considerations. Those skilled in the art will further understand that the release layer 510 and/or the conductive strip 550 need not be strictly rectangular, and/or may include one or more non-rectangular portions.

Figure 5B:
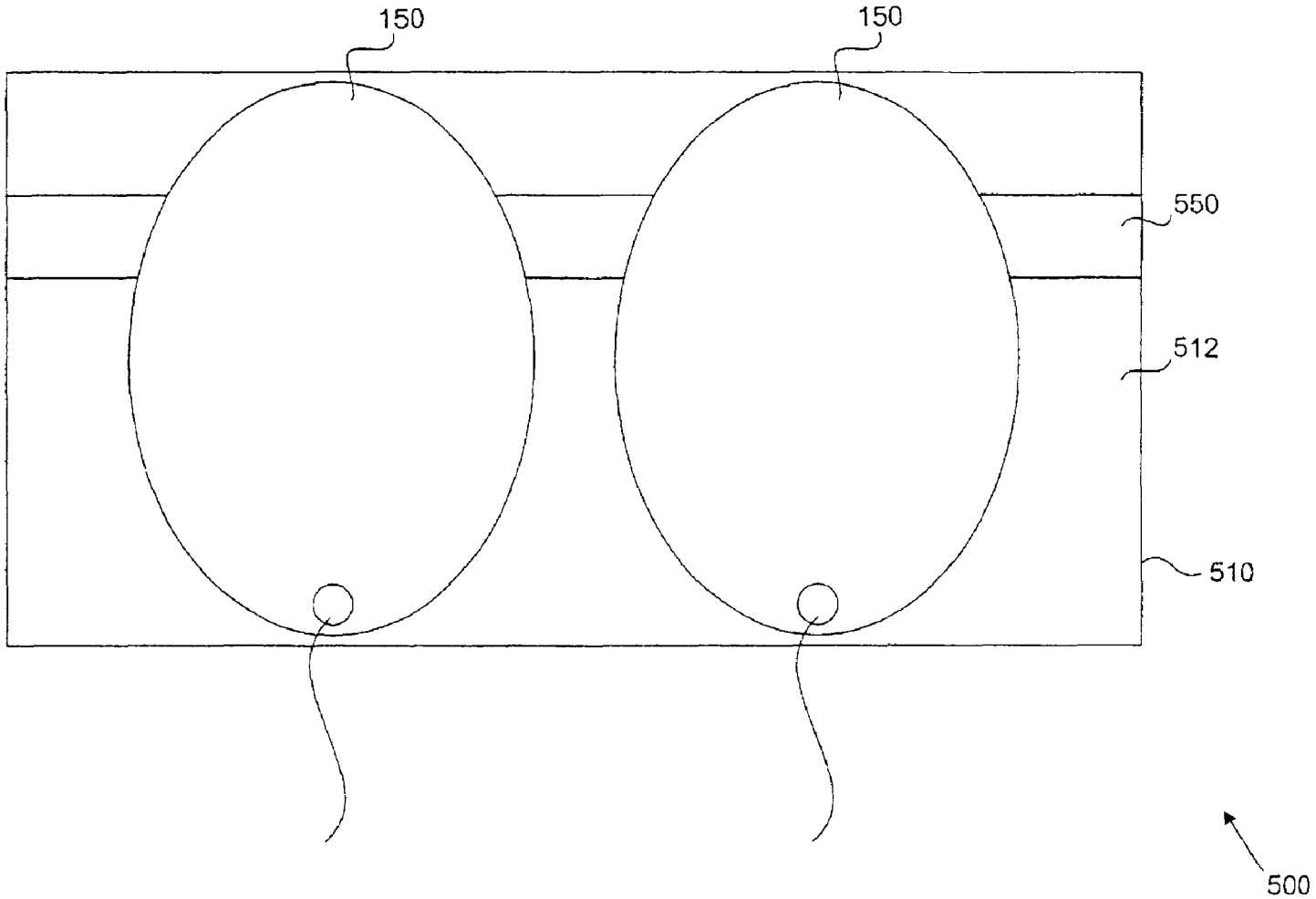
FIG. 5B is a plan view of electrodes mounted upon the release liner of FIG. 5A.

FIG. 5B is a perspective view of electrodes 150 mounted upon the release liner 500 of FIG. 5A. Electrodes 150 may be positioned or mounted upon the mounting surface 512 in a side-by-side manner, such that a portion of each electrode's hydrogel layer electrically contacts the conductive strip 550. Thus, the conductive strip 550 facilitates current flow between electrodes 150 mounted upon the release liner 500. When electrodes 150 mounted upon the release liner 500 are coupled to a medical device, the medical device may electrically test or characterize the electrical path from one electrode 150 to the conductive strip 550 to another electrode 150. A short or open circuit condition may imply a problem with a lead wire, a connector, one or more electrodes 150, and/or the conductive strip 550. As electrodes' hydrogel layers lose moisture, the impedance that a medical device may measure along the aforementioned electrical path may increase, indicating that one or more electrodes 150 are non-optimal or unfit for use. As described in detail below, the medical device may perform various operations and/or provide indications of electrode fitness following measurement of an impedance associated with electrodes 150 mounted upon a release liner 500.

Figure 6A:
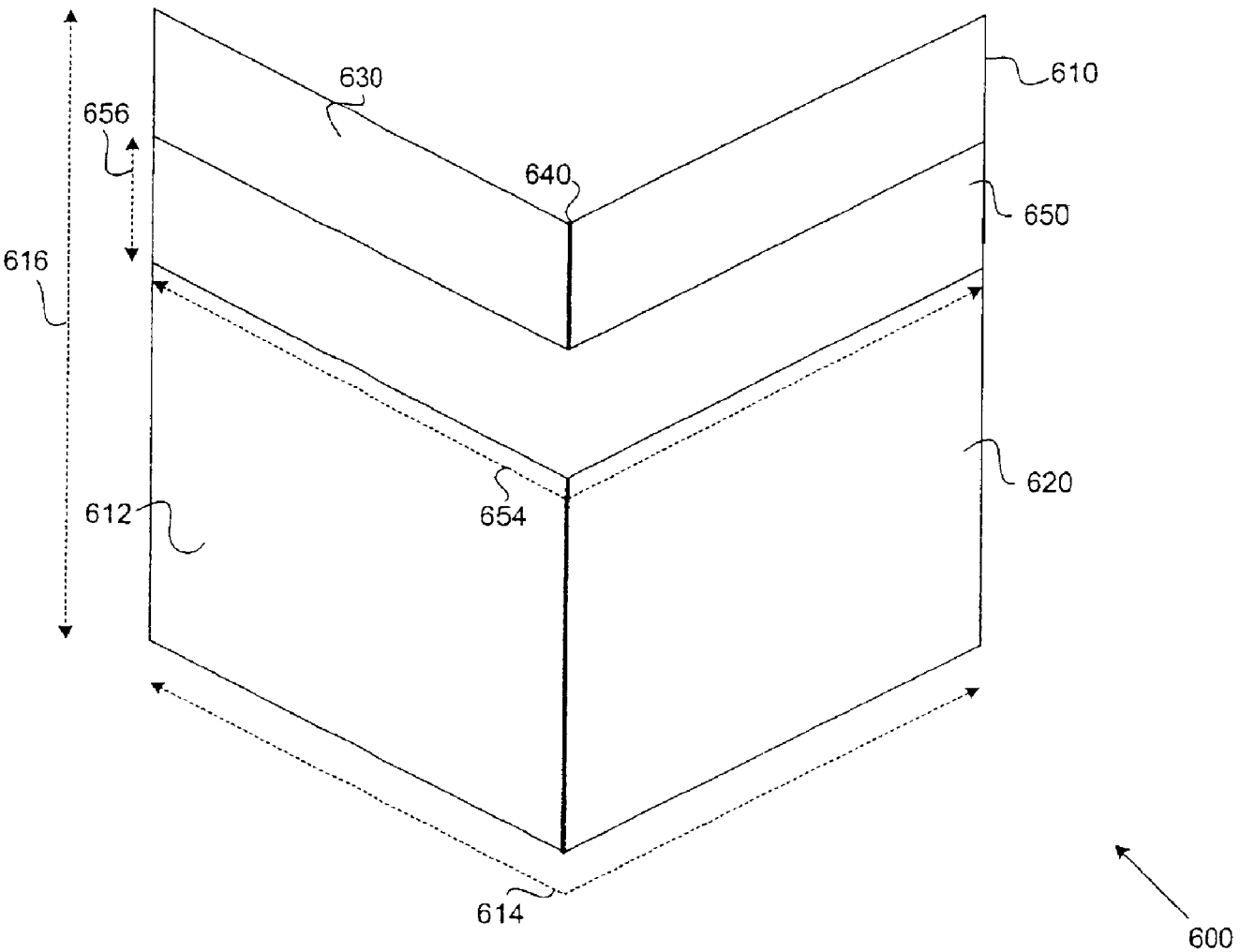
FIG. 6A is a perspective view of another embodiment of a release liner according to the invention.

FIG. 6A is a perspective view of another embodiment of a release liner 600 according to an embodiment of the invention. The release liner 600 comprises a foldable release layer or sheet 610 and a conductive strip 650. The foldable release layer 610 may be characterized by an outer or mounting surface 612; a length 614; a width 616; a first mounting or release portion, region, or segment 620; a second mounting or release portion, region, or segment 630; and a fold region 640. The foldable release layer 610 may be fabricated using a nonconductive, non-stick material in manners previously described. The conductive strip 650 be characterized by a length 654 and a width 656, and may comprise a material such as Aluminum or Tin. The conductive strip 650 may be positioned, mounted, and/or affixed upon the release layer's mounting surface 612.

Figure 6B:
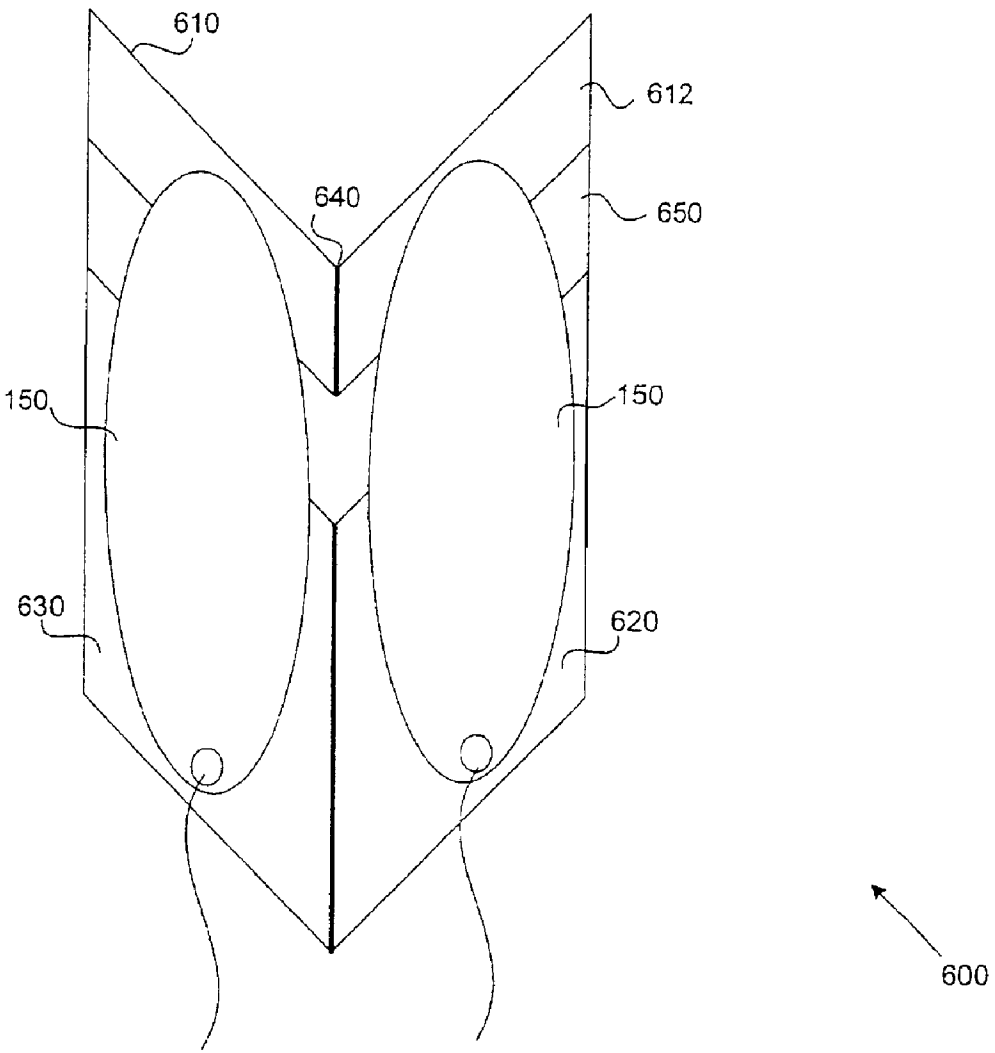
FIG. 6B is a perspective view of electrodes mounted upon the release liner of FIG. 6A.

FIG. 6B is a perspective view of electrodes 150 mounted upon the release liner 600 of FIG. 6A. The foldable release layer 610 may be bent, folded, or doubled about the fold region 640 in either direction (i.e., such that the conductive strip 650 is exposed, or such that the conductive strip 650 is enclosed by the release layer 610 and is therefore unexposed), thereby reducing or minimizing the amount of space the release liner 610 and mounted electrodes 150 occupy. Electrodes 150 may be mounted in a side-by-side manner upon the foldable release layer's mounting surface 612, such that one electrode 150 resides upon the first mounting portion 620 and another electrode resides upon the second mounting portion 630. When mounted in such a manner, a portion of each electrode's hydrogel layer electrically contacts the conductive strip 650. Thus, electrical current may flow from one electrode 150 to another via the conductive strip 650. As with the release liner of FIGS. 5A and 5B, a medical device to which the mounted electrodes 150 are coupled may test or characterize the electrical path between one electrode 150, the conductive strip 650, and another electrode 150. The medical device may provide an indication of electrode fitness based upon such electrical path characterization in manners described below. Those skilled in the art will recognize that the release layer 610 and/or the conductive strip 650 may exhibit a variety of dimensional characteristics, in a manner analogous to that described above with respect to FIG. 5A.

Figure 7:
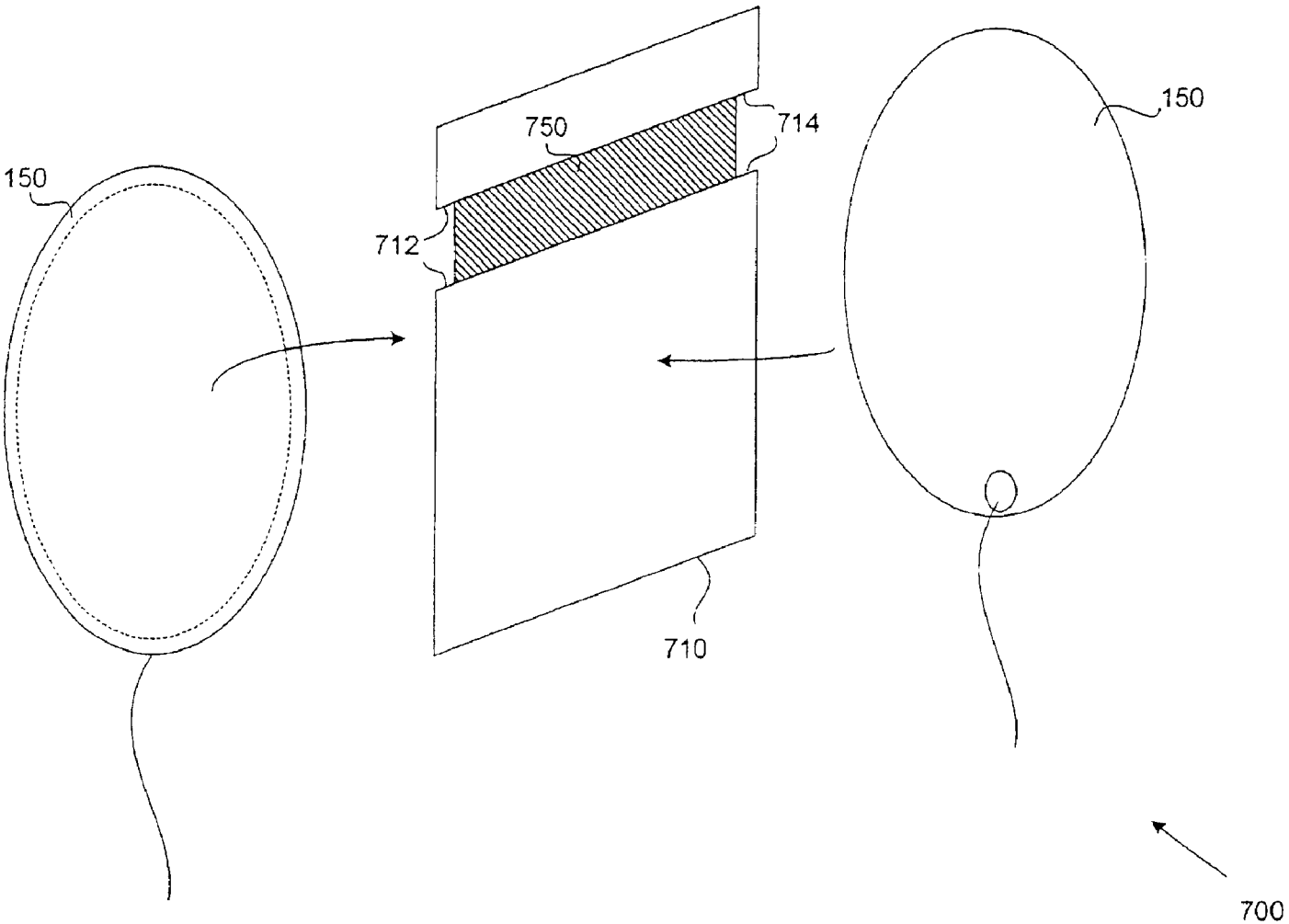
FIG. 7 is a perspective view of a release liner according to another embodiment of the invention, and a manner of mounting electrodes upon the same.

FIG. 7 is a perspective view of a release liner 700 according to another embodiment of the invention, and a manner of mounting electrodes 150 thereupon. In the embodiment shown, the release liner 700 comprises a conductive strip or band 750 mounted upon a single release layer or sheet 710 having a first and a second indented portion or region 712, 714. The release layer 710 comprises a nonconductive, non-stick material constructed in a manner analogous to release layers described above. The indented portions 712,714 may be cut, stamped, or punched out of the release layer 710 during manufacture. The conductive band 750 comprises an electrically conductive material such as a metal.

The conductive band 750 may be positioned, mounted, and/or affixed upon or around the release layer 710 within boundaries defined by the release layer's first and second indented portions 712, 714. Thus, the conductive band 750 may wrap around the release layer, held in position by borders or edges defined by the release liner's indented portions 712, 714. In an alternate embodiment, the conductive band 750 may comprise a first and a second conductive band, which may overlap.

One electrode 150 may be mounted or positioned upon a first side of the release layer 710, while another electrode 150 may be mounted or positioned upon a second side of the release layer 710. The conductive band 750 facilitates electrical contact between the electrodes' hydrogel layers. Thus, a medical device to which the mounted electrodes 150 are coupled may test or characterize the electrical path through one electrode 150, the conductive band 750, and the other electrode 150. Those skilled in the art will understand that in alternate embodiments, the release layer may have one or no indented portion 712, 714, and/or the conductive band 750 may only partially wrap around the release layer 710. In such an embodiment, the conductive band 750 may be affixed or adhered to the release layer 710 via conventional techniques. Those skilled in the art will further understand that in an alternate embodiment, the indented portions 712, 714 may be replaced with protruding portions.

Figure 8A:
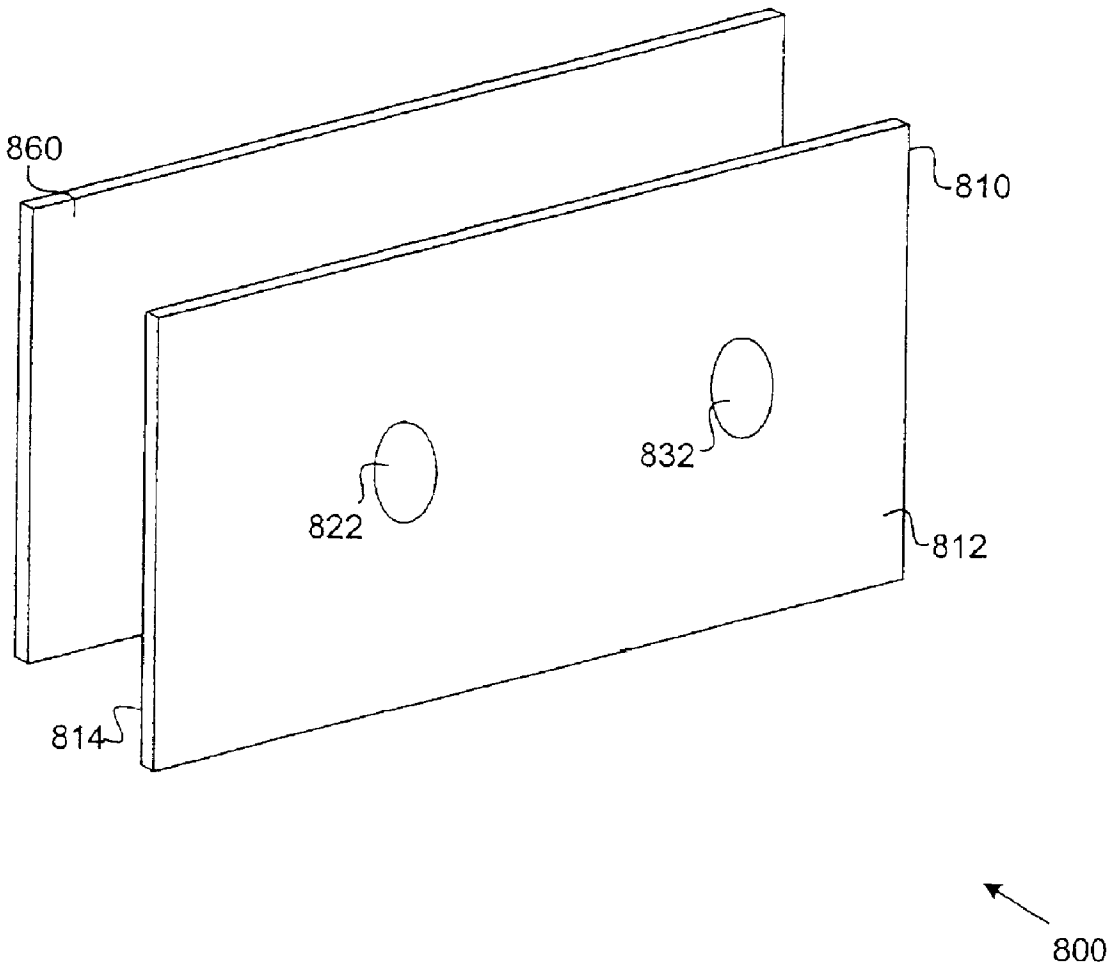
FIG. 8A is a layered perspective view of a release liner according to another embodiment of the invention.

FIG. 8A is a layered perspective view of a release liner 800 according to another embodiment of the invention. The release liner 800 comprises a release layer or sheet 810 and a backing layer 860. The release layer 810 may comprise a nonconductive, non-stick sheet having a front or electrode mounting surface 812; a rear or backing surface 814; a first opening 822; and a second opening 832. The release layer 810 may be manufactured using materials such as those described above, and the openings 822, 832 therein may be cut, punched, and/or stamped out of such materials via conventional techniques.

The backing layer 860 may comprise an electrically conductive layer positioned, mounted, or affixed upon the release layer's rear surface 814. When the backing layer 860 is mounted or positioned upon the release layer's rear surface 814, the nonconductive release layer 810 covers the backing layer 860 except in areas defined by the release layer's openings 822, 832. Those skilled in the art will understand that the backing layer 860 need not be the same size as the release layer 810, as long as the backing layer 860 covers the release layer's openings 822, 832. The backing layer 860 may comprise, for example, a metal or foil. The foil may itself be mounted upon or affixed to a substrate or carrier material, such as paper. Alternatively, the backing layer 860 may comprise a conductive adhesive layer, such as a layer of hydrogel, which may reside upon a substrate or carrier material such as paper or plastic.

Figure 8B:
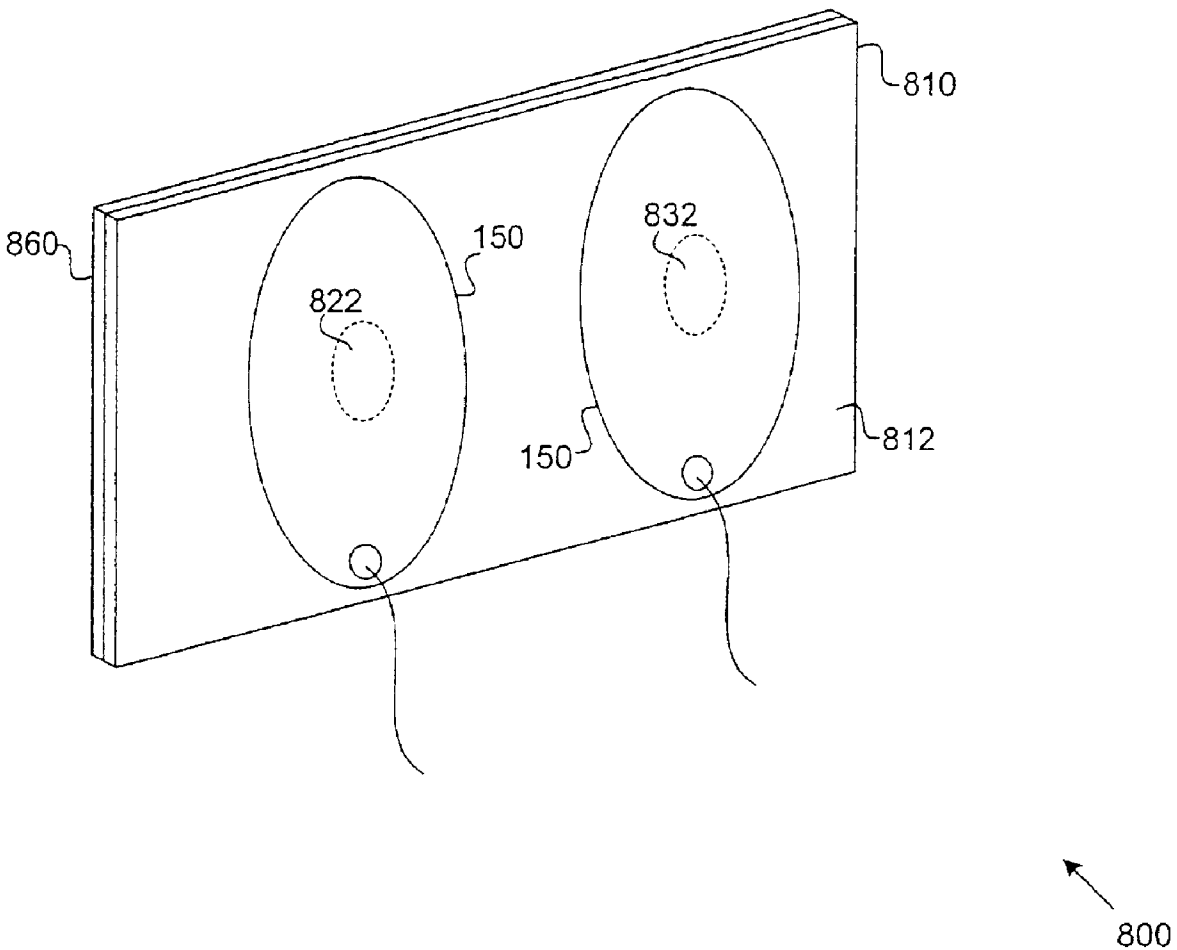
FIG. 8B is a perspective view of electrodes mounted upon the release liner of FIG. 8A.

FIG. 8B is a perspective view of electrodes 150 mounted upon the release liner 800 of FIG. 8A. Electrodes 150 may be mounted upon the release layer's mounting surface 812 in a side-by-side manner, such that one electrode 150 covers the release layer's first opening 822, and another electrode 150 covers the release layer's second opening 832. When an electrode 150 covers an opening in the release layer 810, the electrode's hydrogel layer contacts the conductive backing layer 860 through the opening 822, 832. Thus, the openings 822, 832 facilitate current flow between the electrode's hydrogel layer and the backing layer 860. Hence, when electrodes 150 reside upon the release liner 800, electrical current may flow from an electrode 150 covering the first opening 822 into the backing layer 860, and into an electrode 150 covering the second opening 832.

In an alternate embodiment, the release layer 810 may comprise two or more separate sheets or electrode mounting or release portions rather than a single sheet. Each mounting portion may include an opening. Mounting portions upon which electrodes 150 may reside may be positioned upon the conductive backing layer 860 in a variety of manners (electrodes 150 may be positioned upon mounting portions either before or after such mounting portions are situated upon the conductive backing layer 860). In conjunction with the conductive backing layer 860, the openings in the mounting portions facilitate electrical communication or signal exchange between electrodes 150.

In release liner embodiments previously described with reference to FIGS. 1 through 7, electrical pathways are defined relative to the thickness of hydrogel layers. Impedance values measured through the thickness of one or more hydrogel layers, however, may coincide with or fall within the same range as impedance values associated with a patient, for example, 50 to 250 Ohms. As a result, a medical device may be unable to determine whether electrodes 150 are attached to a patient's body or residing upon a release liner 100, 200, 300, 400. Although impedance values measured through hydrogel layer thickness increase as hydrogel layers dry out, even such increased impedance values are likely to overlap the patient impedance range.

Relative to the release liner of FIGS. 8A and 8B, when the backing layer's conductive medium comprises a layer of hydrogel, electrical current may flow through a length of hydrogel defined by a distance between the release layer's first and second openings 822, 832. The average impedance through the length of a hydrogel layer is much larger than that through the hydrogel layer's thickness. For example, at 70% relative humidity, the average impedance per square through a hydrogel layer's length may be approximately 2 kOhm. This impedance is greater than the patient impedance range by an amount sufficient to ensure that a measured impedance value indicates that electrodes 150 are mounted upon the release liner 800 rather than a patient's body. In addition to the release liner 800 embodiments shown in FIGS. 8A and 8B, other release liner structures that advantageously establish current paths through a length of an electrode's hydrogel layer are described in detail below with reference to FIGS. 10A, 10B, 11, and 12.

A medical device to which electrodes 150 mounted upon as the release liner 800 of FIG. BA are coupled may test or characterize the electrical pathway defined by one electrode 150, the backing layer's conductive medium exposed within and extending between the release layer's first and second openings 822, 832, and another electrode 150. A short or open circuit condition may imply a problem with one or more electrodes 150. As electrodes' hydrogel layers lose moisture, the impedance of the aforementioned electrical path will increase. The impedance of this electrical path will also increase as hydrogel used in the backing layer 860 loses moisture. Upon measuring an impedance level that exceeds a given threshold, the medical device may indicate that the electrodes 150 are non-optimal or no longer fit for use, as further detailed below.

Different hydrogel formulations, as well as identically formulated hydrogels originating from different manufacturing hatches, may exhibit different moisture absorption and loss characteristics. Referring again to FIGS. 8A and 8B, in the event that the backing layer 860 comprises a layer of hydrogel originating from a different formulation or manufacturing batch than that of the electrodes 150 mounted upon the release liner 800, the electrodes' hydrogel layers may donate moisture to or receive moisture from the backing layer's hydrogel. This, in turn, may cause the electrodes' hydrogel layers to undesirably swell or prematurely dry out.

If the backing layer's hydrogel arises from the same manufacturing batch as that of the electrodes 150, the backing layer's hydrogel will neither donate moisture to or receive moisture from the electrodes' hydrogel layers. Rather, the backing layer's hydrogel may lose moisture to the inside of a package at a rate that is identical or essentially identical to that at which the electrodes 150 lose moisture. The backing layer 860 may therefore provide a moisture reservoir to a package, advantageously enhancing the lifetime of electrodes 150 within the package.

Figure 9A:
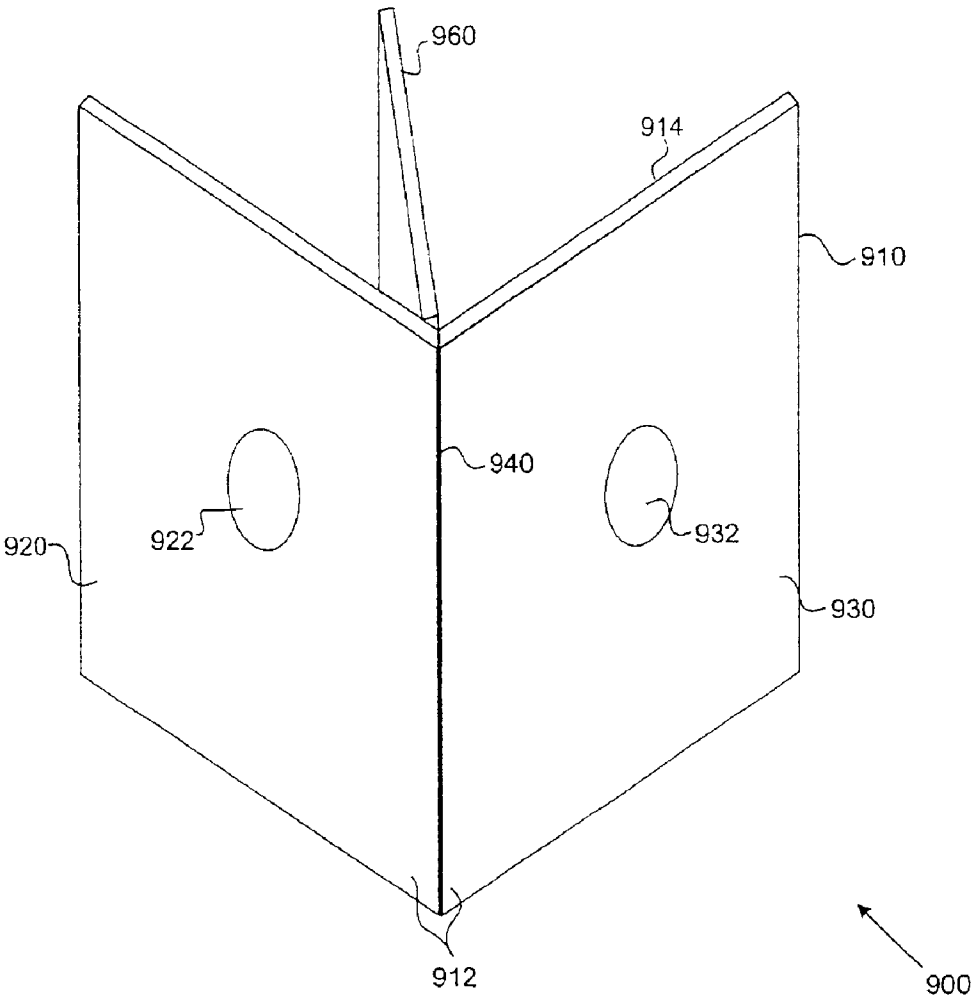
FIG. 9A is a perspective view of a release liner according to another embodiment of the invention.

FIG. 9A is a perspective view of a release liner 900 according to another embodiment of the invention. The release liner 900 comprises a foldable release layer or sheet 910 and a conductive backing layer 960. The foldable release layer 910 comprises a nonconductive, non-stick sheet that includes an electrode mounting surface 912; a backing surface 914; a first mounting or release portion 920 having a first opening 922; a second mounting or release portion 930 having a second opening 932; and a fold region 940. The foldable release layer 910 may be manufactured from conventional nonconductive, non-stick materials such as those previously described, where the first and second openings 922, 932 may be cut, punched, or stamped out of such materials in conventional manners.

The backing layer 960 may comprise a conductive material such as a layer of metal or hydrogel. The foldable release layer 910 may be folded, bent, or doubled in either direction about its fold region 940 such that its backing surface 914 surrounds or encases portions of the backing layer 960, thereby forming a release layer-backing layer-release layer assembly in which the backing layer 960 is exposed in regions defined by the release layer's first and second openings 922, 932.

Figure 9B:
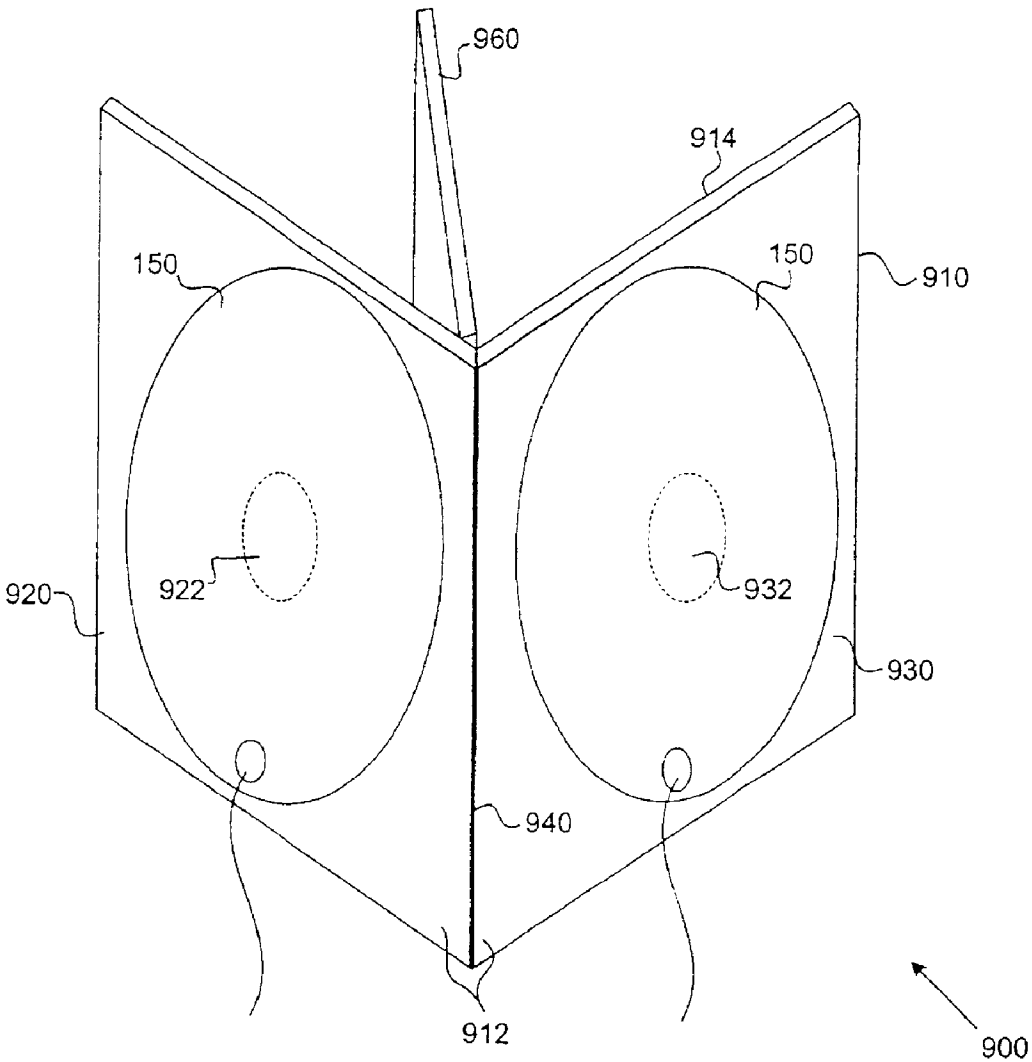
FIG. 9B is a perspective view showing electrodes mounted upon the release liner of FIG. 9A.

FIG. 9B is a perspective view showing electrodes 150 mounted upon the release liner 900 of FIG. 9A. One electrode 150 may be mounted upon the release layer's first mounting portion 920, while another electrode 150 may be mounted upon the release layer's second mounting portion 930. Thus, the electrodes 150 both reside upon the release layer's mounting surface 912.

A medical device to which the electrodes 150 are coupled may electrically test or characterize the electrical path through one electrode's hydrogel layer, the release layer's first opening 922, the conductive medium of the backing layer 960, the release layer's second opening 932, and the other electrode's hydrogel layer. A short or open circuit condition may imply a problem with one or more electrodes 150. As electrodes' hydrogel layers, as well as a hydrogel layer within the conductive backing layer 960 lose moisture, the impedance of the aforementioned electrical path will increase. Upon measuring an impedance level that exceeds a given threshold, the medical device may indicate that the electrodes 150 are non-optimal or no longer fit for use, as further described in detail below.

As described above, release liner structures facilitating electrode characterization via electrical current flow through a given length of hydrogel may enable a medical device to accurately and/or consistently determine whether electrodes 150 are mounted upon the release liner structure or a patient's body. Additional release liner structures that facilitate electrical characterization of electrodes 150 in this manner are described in detail hereafter.

Figure 10A:
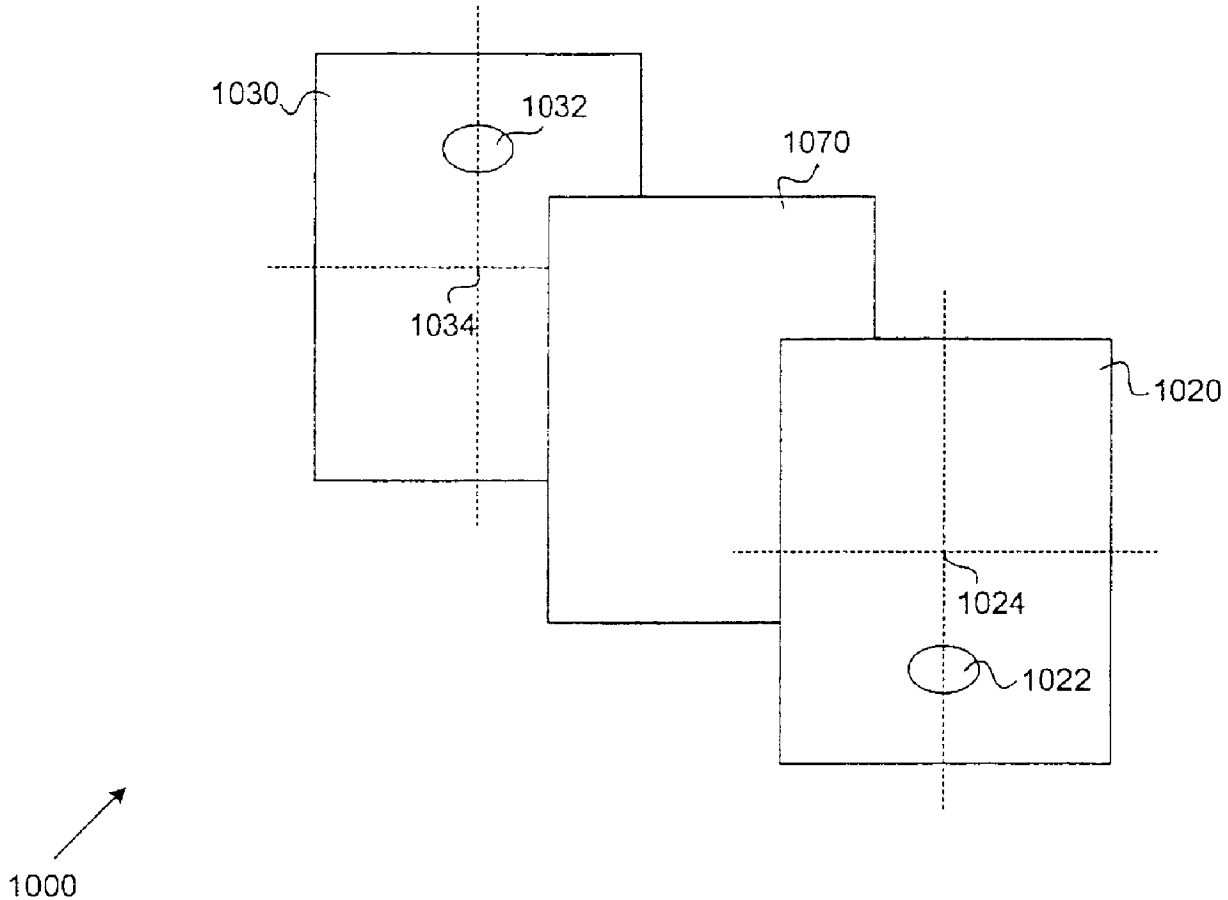
FIG. 10A is a layered plan view of a release liner according to another embodiment of the invention.

FIG. 10A is a layered plan view of a release liner 1000 according to another embodiment of the invention. In one embodiment, the release liner 1000 comprises a first release layer or sheet 1020, a second release layer or sheet 1030, and an intervening conductive adhesive layer or hydrogel layer 1070. Each release layer 1020, 1030 comprises a nonconductive, non-stick material that may be implemented or fabricated using a variety of conventional materials, such as those described above. The first release layer 1020 includes an opening 1022 that is offset or shifted relative to a center point 1024. Similarly, the second release layer 1030 includes an opening 1032 that is offset or shifted relative to a center point 1034.

The first and second release layers 1020, 1030 may be positioned to cover or encase portions of the hydrogel layer 1070, such that the first and second openings 1022, 1032 are non-coincident. In such an alignment, the first and second openings 1022, 1032 are offset with respect to each other relative to any given release layer's center point 1024, 1034. When covering or encasing the hydrogel layer 1070, the first and second release layers 1020, 1030 may be adhered, laminated, or attached together. Alternatively, adhesion between the release liner's hydrogel layer 1070 and electrodes' hydrogel layers may be sufficient to hold the release liner 1000 together.

Figure 10B:
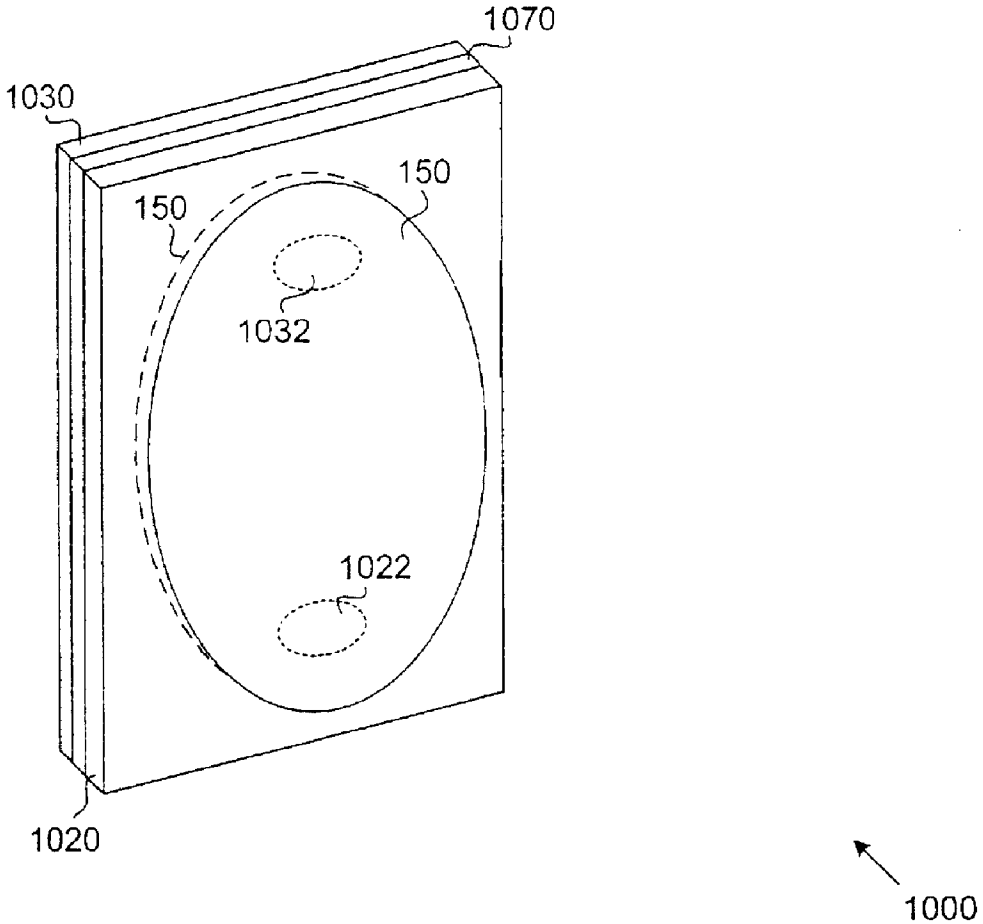
FIG. 10B is a perspective view of electrodes mounted upon the release liner of FIG. 10A.

FIG. 10B is a perspective view of electrodes 150 mounted upon the release liner of FIG. 10A. One electrode 150 resides upon the first release layer 1020, while another electrode 150 resides upon the second release layer 1030. A medical device to which the electrodes 150 are coupled may test or characterize an electrical path through the thickness of one electrode's hydrogel layer in the area spanned by the first opening 1022; the length of the release liner's hydrogel layer 1070 spanning a distance between the first and second openings 1022, 1032; and the thickness of another electrode's hydrogel layer in the area spanned by the second opening 1032. Since current flows through an electrical path that includes a length of hydrogel significantly larger than the thickness of the electrodes' hydrogel layers or the release liner's hydrogel layer 1070, the impedance associated with this electrical path will be significantly greater than typical patient impedance ranges.

The medical device may measure a short or open circuit condition, which may imply dysfunctional or nonoperational electrodes 150. As the electrodes' hydrogel layers lose moisture, or as the release liner's hydrogel layer 1070 loses moisture, the impedance associated with the electrical path in this embodiment will increase. The medical device may subsequently determine that the electrodes 150 are non-optimal or unfit for use, and provide an indication of such in manners detailed below.

Figure 11A:
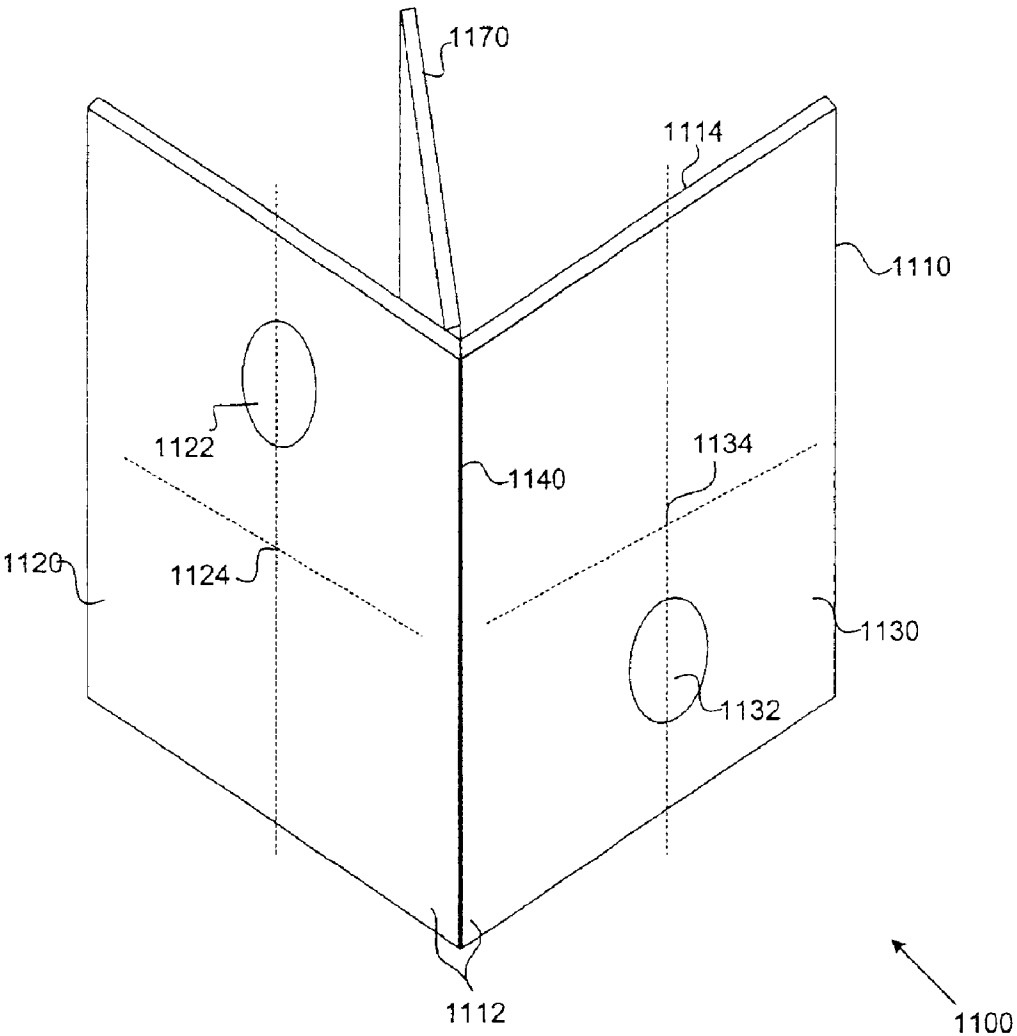
FIG. 11A is a perspective view of a release liner according to another embodiment of the invention.

FIG. 11A is a perspective view of a release liner 1100 according to another embodiment of the invention. In one embodiment, the release liner 1100 comprises a foldable release layer or sheet 1110 and a hydrogel layer 1170. The foldable release layer 1110 may comprise a nonconductive, non-stick sheet that includes an electrode mounting surface 1112; a rear surface 1114; a first mounting or release portion 1120 having a first opening 1122 offset relative to a midpoint 1124 within the first mounting portion 1120; a second mounting or release portion 1130 having a second opening 1132 offset relative to a midpoint within the second mounting portion 1130; and a fold region 1140. The foldable release layer 1110 may be fabricated from conventional materials such as those described above, where the first and second openings 1122, 1132 may be cut, punched, and/or stamped out in conventional manners. In an alternate embodiment, the first and/or second openings 1122, 1132 may respectively comprise a first and/or a second set of openings.

The foldable release layer 1110 may be folded, bent, or doubled about its fold region 1140 such that its rear surface 1114 surrounds or encases portions of the hydrogel layer 1170. The hydrogel layer 1170 may be exposed via the first and second openings 1122, 1132 within the first and second mounting portions 1120, 1130, respectively. When the release layer 1110 is folded and encases the hydrogel layer 1170, the first and second openings 1122, 1132 are non-coincident or offset relative to each other, such that they are separated by a predetermined or as-manufactured length or distance. This separation distance ensures that when electrodes 150 are mounted upon the release liner 1100 and coupled to a medical device, electrical current may travel through a given length of the hydrogel layer 1170, where this length is significantly greater than the hydrogel layer's thickness. As a result, the electrical path provided by the release liner of FIG. 11A may exhibit an impedance level significantly greater than typical patient transthoracic impedance levels.

Figure 11B:
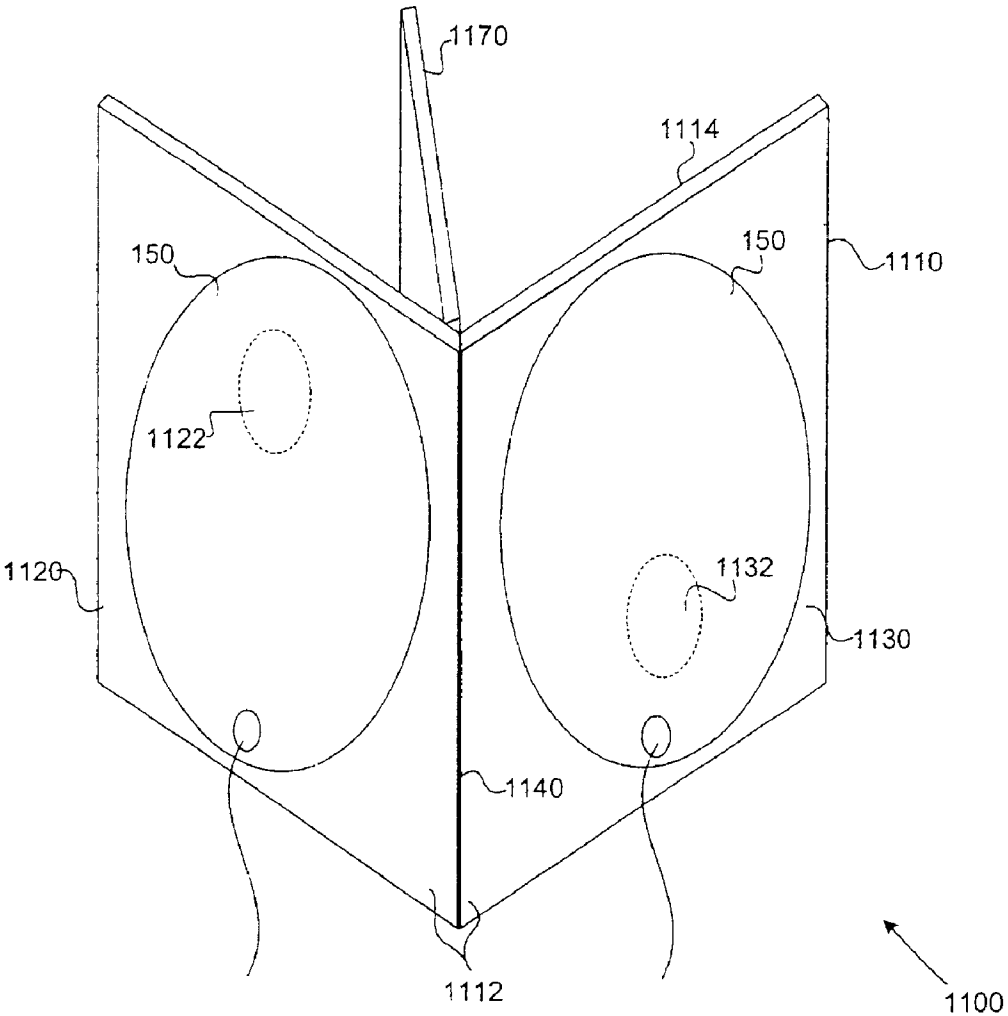
FIG. 11B is a perspective view of electrodes mounted upon the release liner of FIG. 1A.

FIG. 11B is a perspective view of electrodes 150 mounted upon the release liner 1100 of FIG. 11A. Electrodes 150 mounted upon this release liner 1100 may be tested and/or characterized in manners analogous to those described above for other release liner embodiments.

Electrodes themselves may be designed such that current flow within the electrode may occur through a given length of the electrode's hydrogel layer when the electrodes are mounted upon a release liner. Various electrode embodiments that may be characterized by current flow through portions of a hydrogel layer's length are described in detail hereafter.

Figure 12A:
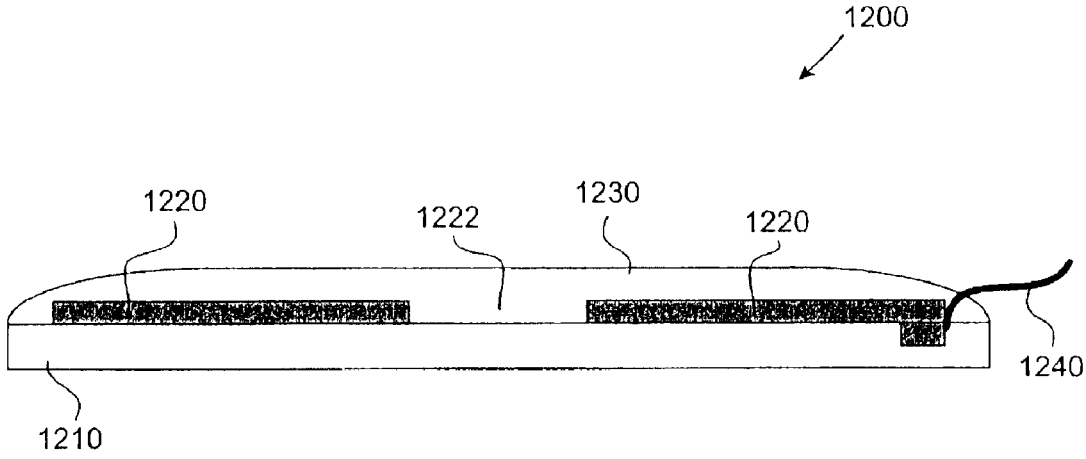
FIG. 12A is a cross sectional view of an electrode according to an embodiment of the invention.
Figure 12B:
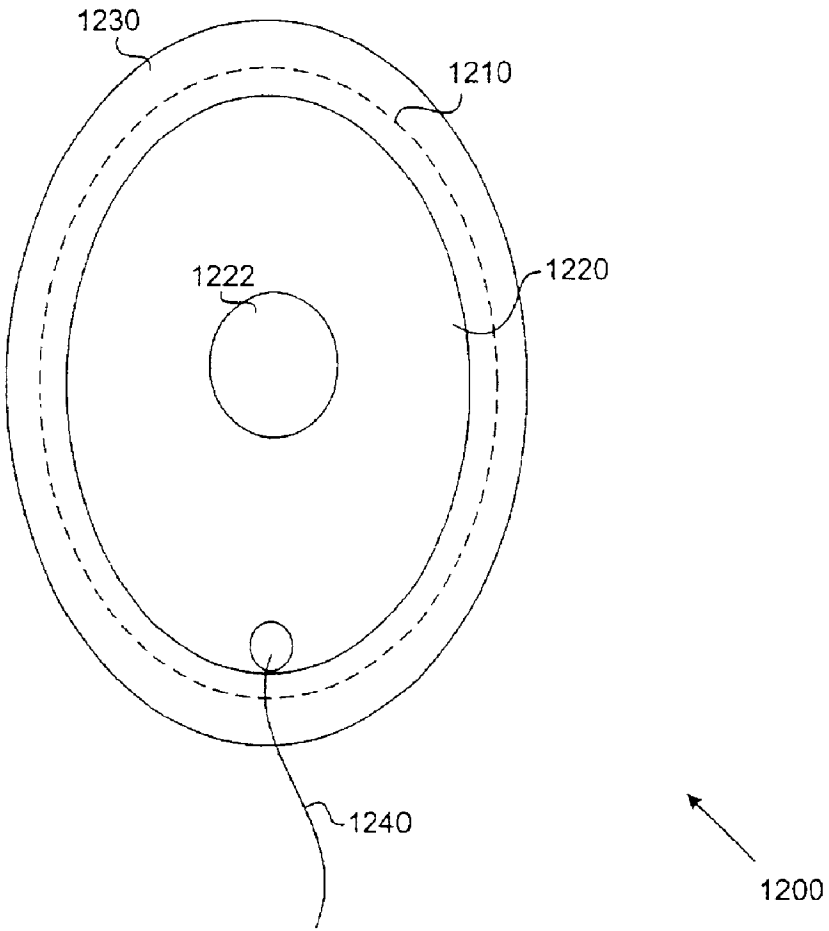
FIG. 12B is a plan view of the electrode of FIG. 12A.

FIG. 12A is a cross sectional view of an electrode 1200 according to an embodiment of the invention. FIG. 12B is a plan view of the electrode 1200 of FIG. 12A. In the embodiment shown, the electrode 1200 comprises a conductive adhesive material, gel layer, or hydrogel layer 1210; a conductive or foil layer 1220 having at least one opening or void 1222 therein; an insulating or dielectric layer 1230; and a lead wire 1240. Each element 1210, 1220, 1230, 1240 within the electrode 1200 may be implemented using conventional materials. The hydrogel layer 1210 interfaces the electrode 1200 to a patient's body or a release liner. The foil layer 1220 resides upon the hydrogel layer 1210, and the insulating layer 1230 resides upon the foil layer 1220. Finally, the lead wire 1240 is coupled to the foil layer 1220, and may be covered with an insulating material in a manner well understood by those skilled in the art.

Each void 1222 may be cut, stamped, or punched out of the conductive foil layer 1220 in a conventional manner. Furthermore, each void 1222 may be positioned at a given location that corresponds to an area in which electrical contact with a conductive region, area, section, and/or element of an appropriate type of release liner is desired. The presence of a void 1222 in the foil layer 1220 may affect the manner in which electrical current may flow through or within the electrode 1200 when the electrode 1200 is mounted upon a patient's body.

Figure 13A:
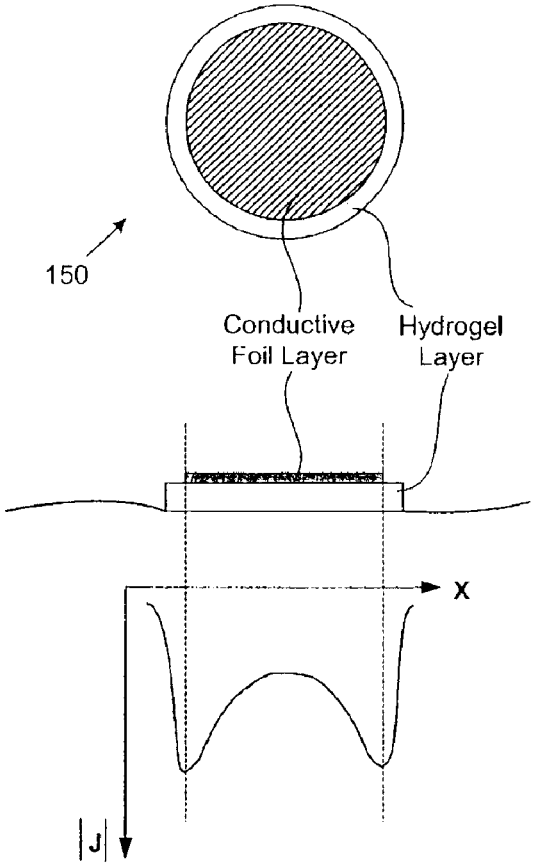
FIG. 13A is a graph of exemplary current density relative to lateral position for a conventional electrode mounted upon a patient's body.

FIG. 13A is a graph of exemplary current density relative to lateral position for a conventional electrode mounted upon a patient's body. Those skilled in the art will understand that current flows more easily between an electrode and a patient's body near the electrode's edges. As one moves from an interior region toward an outer edge or border of the electrode's foil layer, current density increases and peaks.

Figure 13B:
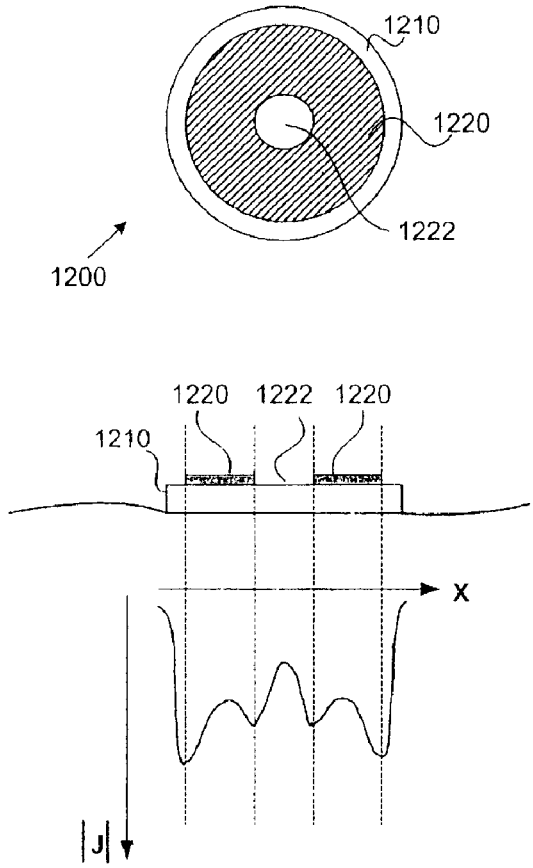
FIG. 13B is a graph of exemplary current density relative to lateral position beneath elements of the electrode of FIG. 12A when the electrode is mounted upon a patient's body.

FIG. 13B is a graph showing exemplary shock current density relative to lateral position beneath elements of an electrode 1200 of FIG. 12A when the electrode 1200 is mounted upon a patient's body. Within a region defined by a void 1222, current density drops to a minimum value relative to its value beneath the foil layer 1220. At a foil layer edge or boundary, current density exhibits a peak. The presence of a void 1222 provides an additional foil layer edge or boundary at which a current density peak may occur. Those skilled in the art will understand that as a result of such current density peaks, the presence of one or more properly positioned voids 1222 in the foil layer 1220 need not increase, and may decrease, the effective shock impedance of the electrode 1200. Those skilled in the art will thus understand that the areas under the curves shown in FIGS. 13A and 13B may be identical or essentially identical. Alternatively, the area under the curve shown in FIG. 13B may be greater than that under the curve shown in FIG. 13A.

Figure 14A:
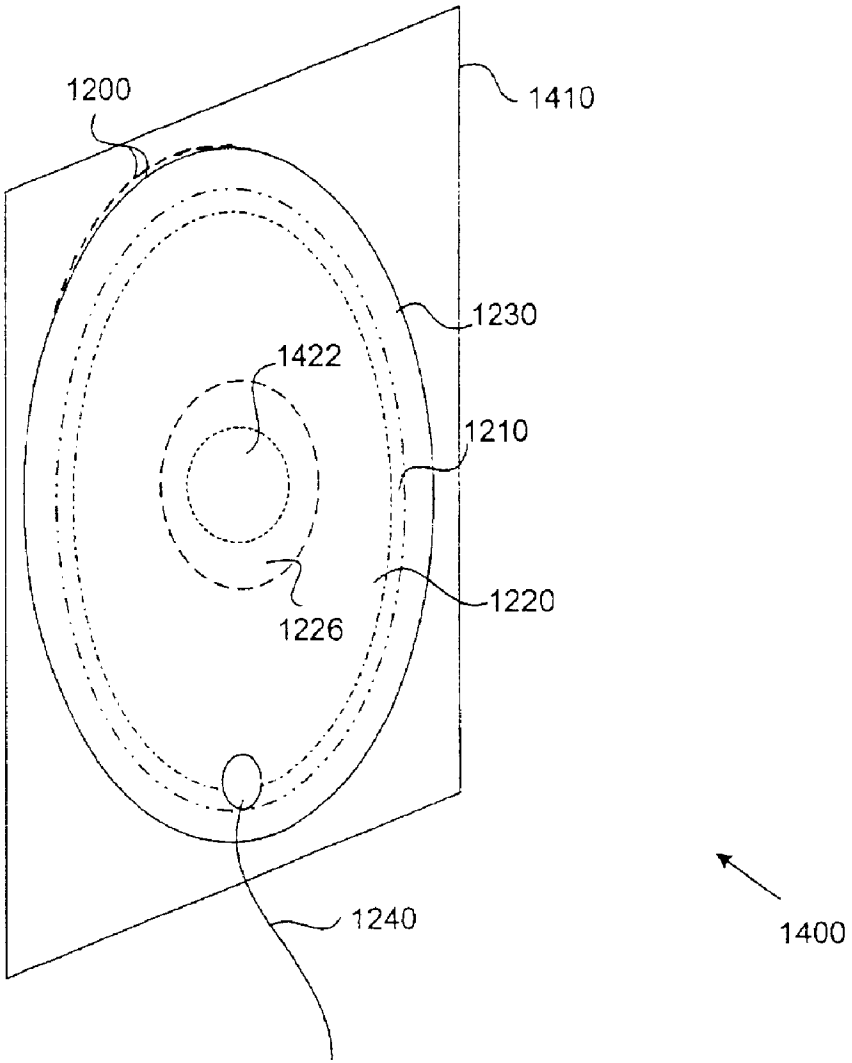
FIG. 14A is a perspective view of electrodes of FIG. 12A mounted upon a release liner according to another embodiment of the invention.
Figure 14B:
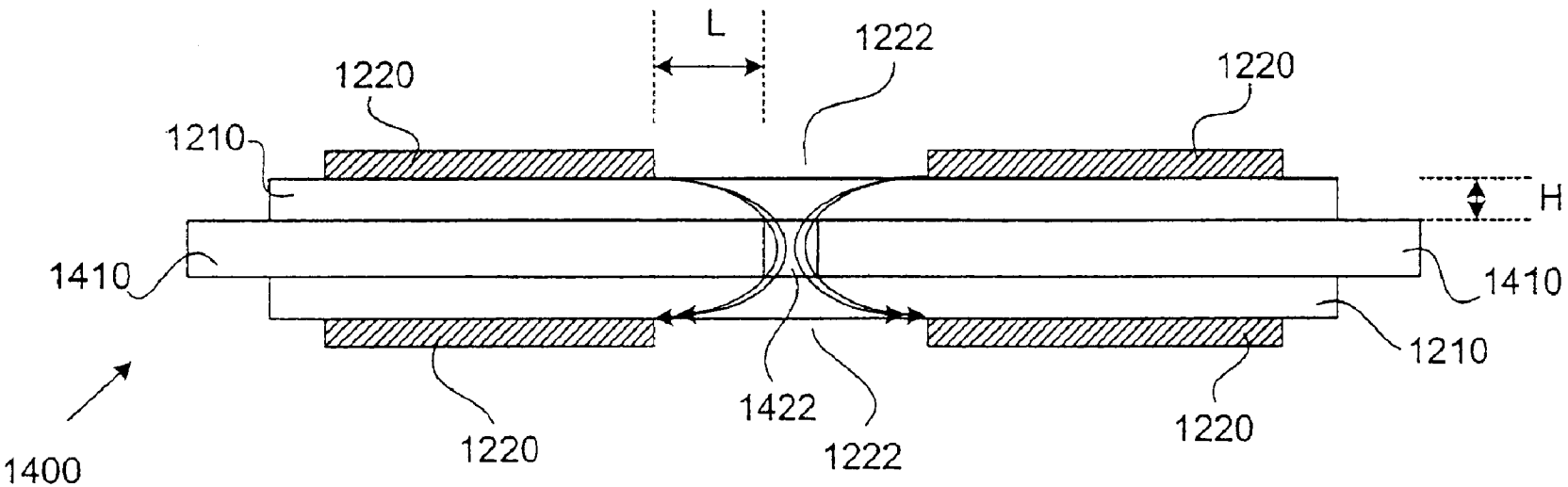
FIG. 14B is a cross sectional view of electrodes of FIG. 12A mounted upon the release liner of FIG. 14A.

The presence of a void 1222 in an electrode's foil layer 1220 may also affect the manner in which electrical current may flow through or within the electrode 1200 when the electrode 1200 is mounted upon a release liner. FIG. 14A is a perspective view of two voided electrodes 1200 of FIG. 12A mounted upon a release liner 1400 according to another embodiment of the invention. FIG. 14B is a cross sectional view of the voided electrodes 1200 mounted upon the release liner 1400 of FIG. 14A. The release liner 1400 may comprise a nonconductive, nonstick release layer 1410 having an opening 1422 therein. The release layer 1410 may be implemented using conventional materials such as those previously described, and the opening 1422 may be cut, stamped, or punched out of the release layer 1410 via conventional techniques.

The release layer's opening 1422 may be smaller than the voids 1222 in the electrodes' conductive foil layers 1220. One voided electrode 1200 may be mounted upon one side of the release layer 1410, while another electrode 1200 may be mounted upon the release layer's opposite side, such that the void 1222 in each electrode's conductive foil layer 1220 surrounds the release layer's opening 1422. The release layer's opening 1422 facilitates hydrogel layer 1210 to hydrogel layer 1210 contact within areas defined by each electrode's void 1222.

The presence of a void 1222 may ensure that electrical current flow involves a hydrogel layer's length and/or width in addition to the hydrogel layer's thickness. That is, current flow may include or be decomposed into lateral or transverse components that are parallel or essentially parallel to a plane defined by the interface between the electrode's hydrogel layer 1210 and the conductive foil layer 1220. When voided electrodes 1200 mounted upon a release liner 1400 are coupled to a medical or measuring device, electrical current may flow from an edge of a given electrode's conductive foil layer 1220 that defines a void's boundary or border, through the given electrode's hydrogel layer 1210 and to the release liner opening 1422 along a path that includes transverse or lateral components, and into and through the other electrode 1200 in a corresponding manner. In other words, electrical current may flow from one electrode 1200 to another along a current path that includes transverse or lateral components through each electrode's hydrogel layer 1210. Exemplary current paths that include transverse or lateral components are indicated in FIG. 14B via curved arrows.

Electrical current may travel a greater distance along a current path that involves transverse components than along a current path defined solely by a hydrogel layer's thickness. Also, bulk impedance values may be larger and/or more readily measured over a longer current path than a shorter current path. As a result, an electrical path that includes or involves transverse components or a length of an electrode's hydrogel layer 1210 between a foil layer/void boundary and a release liner opening 1422 may be characterized by a higher impedance than an electrical path defined by a hydrogel layer's thickness. This, in turn, may ensure that the impedance level corresponding to electrodes 1200 appropriately mounted or positioned upon a release liner 1400 is greater than typical patient impedance levels. Additionally, electrodes 1200 that may be characterized via measurements involving transverse current components (e.g., electrodes 1200 that incorporate one or more voids 1222) may exhibit enhanced response to impedance changes resulting from hydrogel layer moisture loss.

As a result of the foregoing, electrodes 1200 having one or more voids 1222 incorporated therein and which are mounted upon a release liner 1400 may exhibit a packaged or mounted impedance level that is greater or significantly greater than typical patient impedance levels, even for electrodes 1200 that are new, essentially new, and/or in excellent, good, and/or acceptable operating condition. As the condition of one or more such electrodes 1200 deteriorates over time, a packaged impedance measurement may provide a particularly sensitive indication of deterioration, as a corresponding measured impedance may exhibit a large increase over time in response to such deterioration.

The size or area associated with an electrode's void 1222 relative to 1) the size, area, and/or position of a release liner's opening 1422; and/or 2) the thickness of the electrode's hydrogel layer 1210 may affect or determine an extent to which transverse components contribute to electrical current flow. Larger transverse contributions to electrical current flow result in larger measured impedance values. A hydrogel layer 1210 may be characterized by a thickness H. A boundary or edge separation distance between a void 1222 and a release liner opening 1422 may be characterized by a distance L, as shown in FIG. 14B. In one embodiment, to ensure sufficient transverse or lateral contributions to electrical current flow between electrodes 1200 mounted upon a release liner 1400, the ratio L/H should be significantly greater than 1.

The area associated with a given void 1222 may be larger than that associated with a release liner opening 1422 over which the void 1222 is positioned. In an exemplary embodiment, a void 1222 may have an area approximately 300% greater than a release liner opening 1422. Such an area relationship may aid manufacturability by providing a positional tolerance during electrode mounting procedures. Those skilled in the art will understand that the voided electrodes 1200 may have differently sized and/or differently shaped voids, which may further influence the manner in which electrical current may laterally flow through portions of a hydrogel layer. In addition, one or more voids may be present in one electrode 1200, while another electrode lacks voids.

A medical device to which voided electrodes 1200 mounted to a release liner 1400 are coupled may reliably determine whether the voided electrodes 1200 are mounted upon the release liner 1400 or a patient's body. A medical or measuring device may determine that a short or open circuit condition exists along or within the aforementioned electrical path, in which case the electrical path and/or one or more electrodes 1200 may be damaged or defective. The medical or measuring device may also determine an electrode condition or fitness level based upon an impedance measurement. As indicated above, impedance measurements involving transverse or lateral current paths may be particularly sensitive to changes in hydrogel layer moisture content. In the event that an impedance measurement result exceeds a given threshold or range, the medical or measuring device may provide an indication that the electrodes 1200 may be non-optimal or unfit for use, in manners described in detail below.

Figure 15:
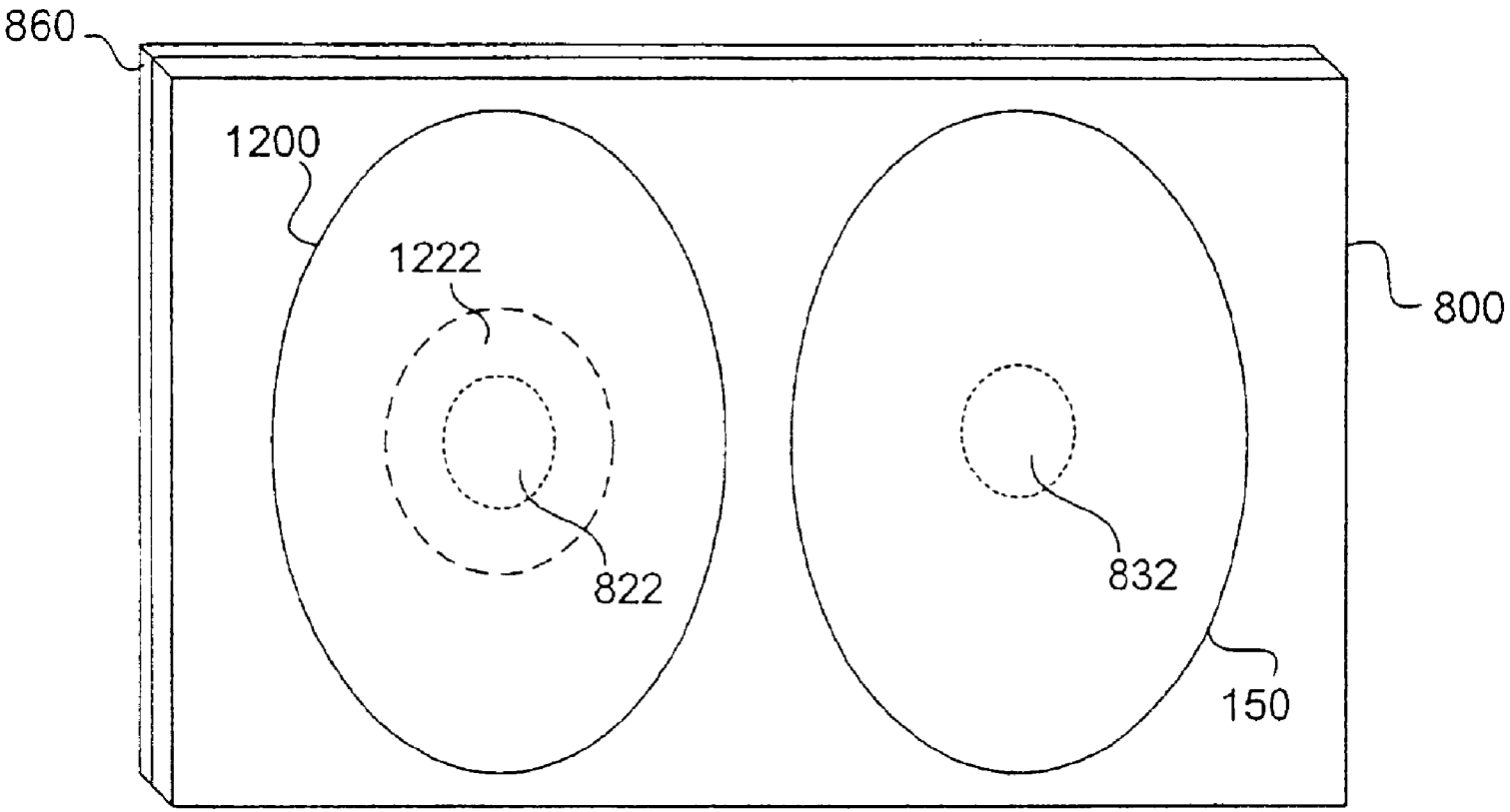
FIG. 15 is a plan view of the electrode of FIG. 12A and a conventional electrode mounted upon the release liner of FIG. 8A.

FIG. 15 is a plan view of the electrode 1200 of FIG. 12A and a conventional electrode 150 mounted upon the release liner of FIG. 8A. The voided electrode 1200 is mounted or oriented such that a void 1222 therein surrounds the release liner's first opening 822, while the conventional electrode 150 is positioned such that it covers or overlaps the release liner's second opening 832. Those skilled in the art will understand that the conventional electrode 150 may be replaced with a voided electrode 1200, 1250 in an alternate embodiment. In an embodiment having an electrode 1250 with multiple voids 1222, 1224, the release liner 800 may include an appropriate set of openings corresponding to each such void 1222, 1224.

A medical device to which the electrodes 1200, 150 are coupled may test or characterize the electrical path laterally through a length of the voided electrode's hydrogel layer 1210, through the release liner's conductive backing layer 860, and through the hydrogel thickness within the conventional electrode 150. A measured impedance level that exceeds a given threshold and/or falls outside a particular range may indicate that one or more electrodes 1200, 150 mounted upon the release liner 800 are non-optimal or unfit for use. The medical device may provide one or more indications of electrode condition or fitness in manners described in detail below.

As described above, any given void 1222, 1224 may affect the manner in which current flow occurs through and/or within an electrode 1200, 1250. The presence of a void 1222, 1224 may result in transverse or lateral current flow through a portion of an electrode's hydrogel layer 1210. For example, when an electrode 1200 is mounted upon a nonconductive release layer such that a void 1222, 1224 surrounds a release layer opening that facilitates access to a conductive medium, a direct electrical path from a foil layer 1220 through the thickness of the hydrogel layer 1210 to the conductive medium may not exist. As a result, transverse current flow may occur. As previously indicated, an electrode 1200 may include multiple voids 1222, which may be shaped and/or positioned in a variety of manners relative to each other.

Figure 12C:
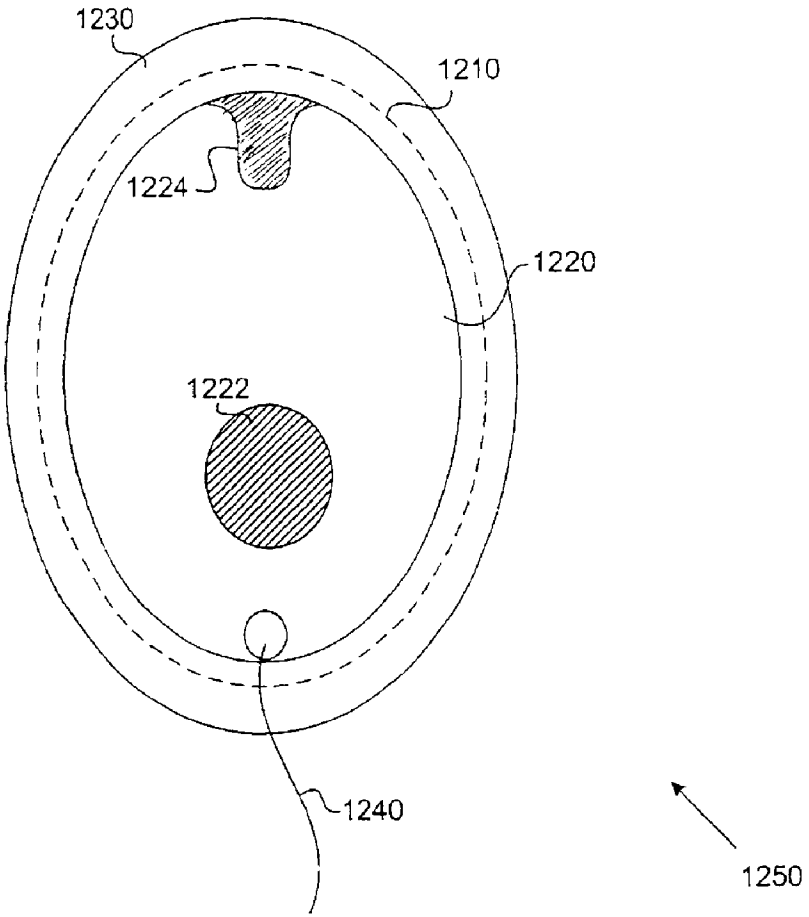
FIG. 12C is a plan view of an electrode according to another embodiment of the invention.

FIG. 12C is a plan view of an electrode 1250 according to another embodiment of the invention. Relative to FIGS. 12A and 12B, like reference numbers indicate like elements for ease of understanding. In the embodiment shown, the electrode 1250 comprises a hydrogel layer 1210; a conductive or foil layer 1220 having a void 1222 and a recess 1224; a dielectric layer 1230; and a lead wire 1240. Each of the hydrogel layer 1210, the foil layer 1220, the dielectric layer 1230, and the lead wire 1240 may be implemented using conventional materials.

The void 1222 may comprise a generally circular, elliptical, or otherwise shaped opening that is generally disposed or positioned within a central region or area of the foil layer 1220. The recess 1224 may comprise an opening and/or open region that extends to an outer edge or boundary of the foil layer 1220. Each void and/or recess 1222, 1224 may be positioned over a corresponding opening in a release liner. In accordance with various embodiments, the voids 1222 and/or recesses 1224 detailed above may be shaped and/or positioned differently. Additionally, any given electrode embodiment may have additional or fewer voids 1222 and/or recesses 1224.

The presence of an insulating material may affect electrical current flow between electrodes mounted upon a release liner in a manner that is identical or essentially identical to that described above relative to voids 1222, as described in detail hereafter.

Figure 12D:
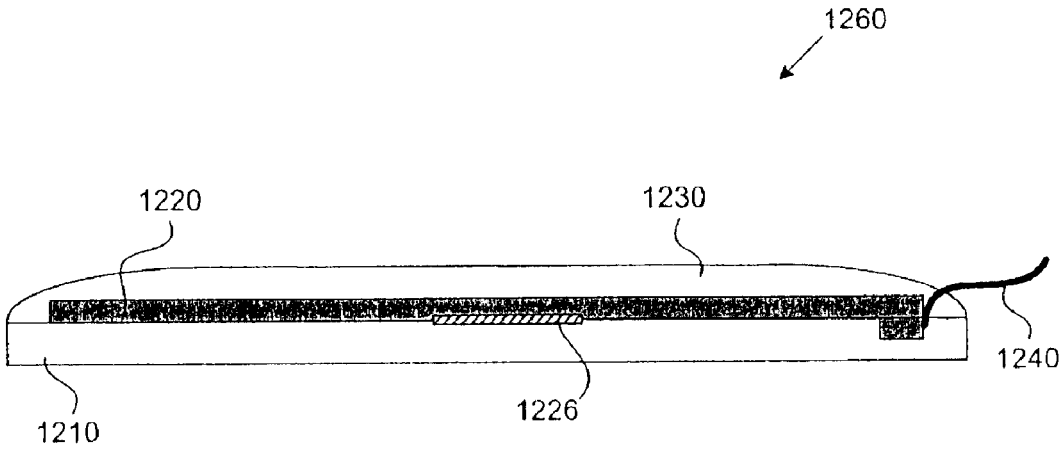
FIG. 12D is a cross sectional view of an electrode according to another embodiment of the invention.
Figure 12E:
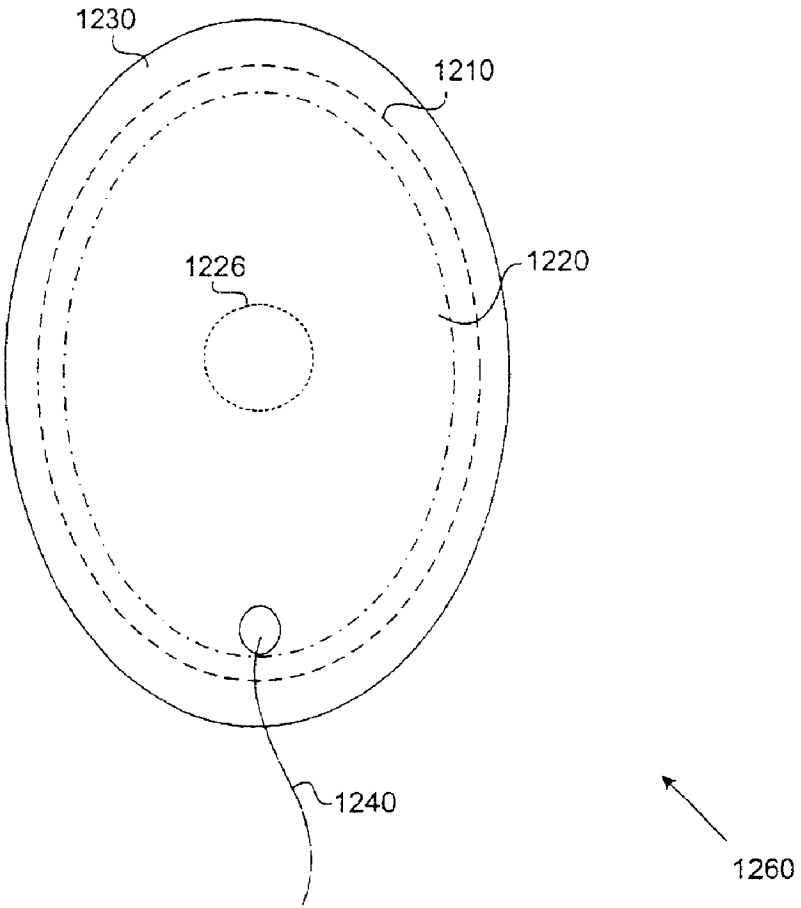
FIG. 12E is a plan view of the electrode of FIG. 12D.

FIG. 12D is a cross sectional view of an electrode 1260 according to another embodiment of the invention. FIG. 12E is a plan view of the electrode 1260 of FIG. 12D. Relative to FIGS. 12A, 12B, and 12C, like reference numbers indicate like elements. The electrode 1260 may comprise a hydrogel layer 1210; a conductive or foil layer 1220; an insulating or dielectric layer 1230; and a lead wire 1240, each of which may be implemented using conventional materials. The electrode 1260 further comprises a set of insulating or nonconductive internal patches or swatches 1226. While FIGS. 12D and 12E show an embodiment that includes a single internal swatch 1226, additional internal swatches 1226 may be present in alternate embodiments. Those skilled in the art will also understand that in alternate embodiments, an electrode may include one or more voids 1222, 1224 instead of or in addition to one or more internal swatches 1226.

Any given internal swatch 1226 may comprise an insulating material such as polyethylene. Each internal swatch 1226 may reside between the hydrogel layer 1210 and the conductive foil layer 1220. An internal swatch 1226 may be positioned at a given location that corresponds to an area in which electrical contact with a conductive region, area, section, and/or element of a release liner or another electrode is desired. Because the internal swatch 1226 is nonconductive, its presence affects the manner in which current may flow through and/or within the electrode 1260, in a manner analogous to that described above for voids 1222.

Figure 16:
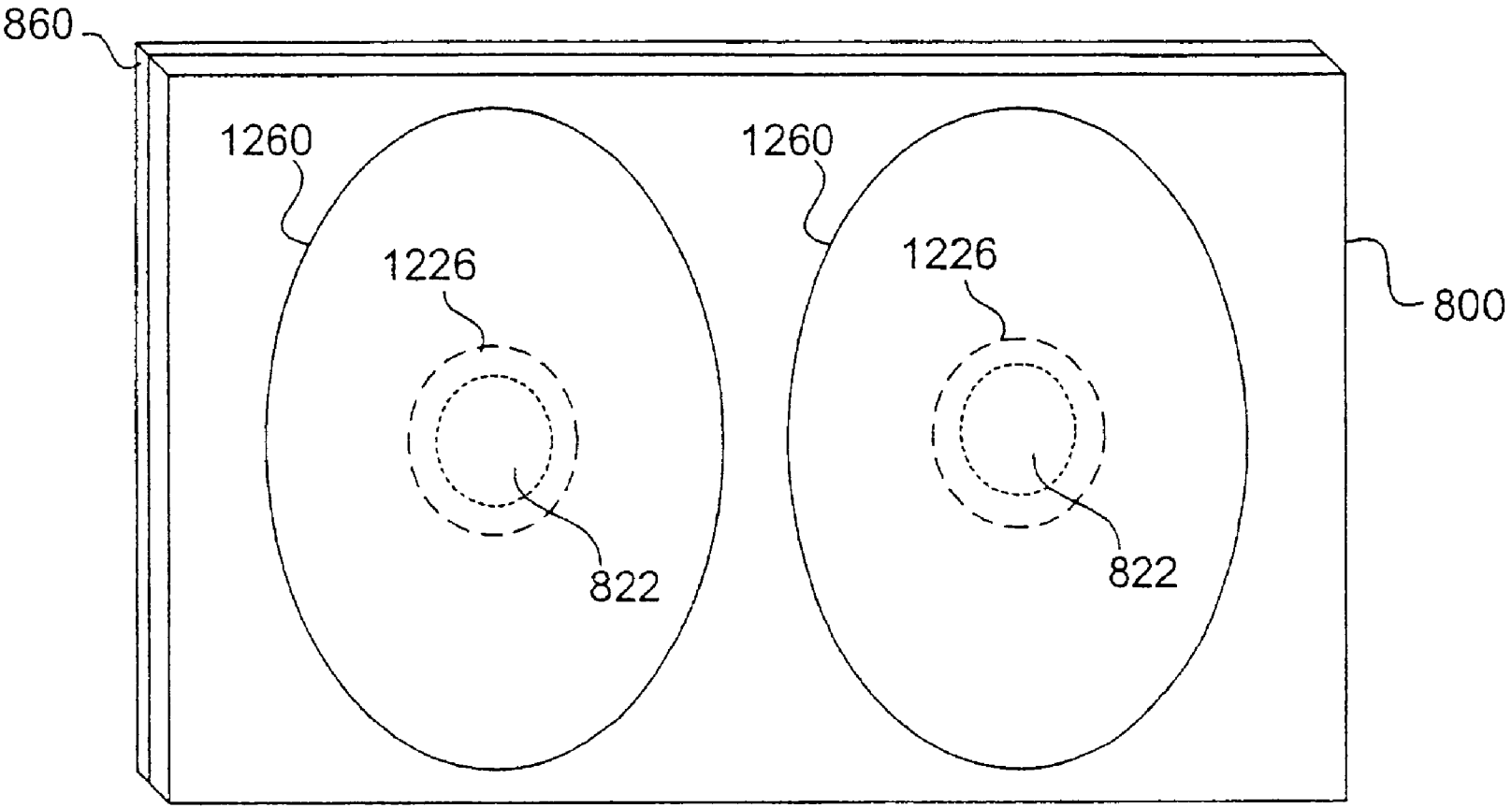
FIG. 16 is a plan view of electrodes of FIG. 12D mounted upon the release liner of FIG. 8A.

FIG. 16 is a plan view showing electrodes 1260 of FIG. 12D mounted upon the release liner 800 of FIG. 8A. One electrode 1260 may be positioned or oriented such that its internal swatch 1226 overlaps or surrounds the release liner's first opening 822, while another electrode 1260 may be positioned or mounted such that its internal swatch 1226 overlaps the release liner's second opening 832. A direct electrical path from any given electrode's foil layer 1220 through the thickness of the electrode's hydrogel layer 1210 and into the release liner's conductive backing layer 860 via the first or second opening 822, 832 may not exist due to the presence of the internal swatches 1226. Thus, the presence of an internal swatch 1226 may result in lateral or transverse current flow through a length of an electrode's hydrogel layer 1210. Such current flow originates from a foil layer 1220 along a boundary or interface defined by an intersection of the foil layer's area and the area of the internal swatch 1226, and laterally extends to or past a boundary or interface defined by the area of an appropriate release liner opening 822, 832. Those skilled in the art will understand that electrodes 1260 incorporating one or more internal swatches 1226 therein may be mounted upon other release liner types, such as the release liner 1400 of FIG. 14A.

A medical device to which the electrodes 1260 are coupled may test or characterize the electrical path through a length of each electrode's hydrogel layer 1210 and through the release liner's conductive backing layer 860 via the first and second release liner openings 822, 832. A measured impedance level that exceeds a given threshold and/or falls outside a particular range may indicate that one or more electrodes 1260 mounted upon the release liner 800 are non-optimal or unfit for use. The medical device may provide one or more indications of electrode condition or fitness in manners described in detail below.

Those skilled in the art will understand that in alternate embodiments, essentially any of the electrodes 1200, 1250, 1260 of FIGS. 12A, 12B, 12C, 12D, and 12E may be mounted upon various types of release liners in conjunction with identical, similar, and/or conventional electrodes 150. Use of voided electrodes 1200, 1250 and/or electrodes 1260 that include an internal swatch 1226 may require release liner embodiments that ensure no overlap between portions of such electrodes' foil layers and a conductive region or medium associated with the release liner exists (i.e., release liner embodiments that ensure a significant amount of transverse current flow through a length of an electrode's hydrogel layer 1210).

Figure 17:
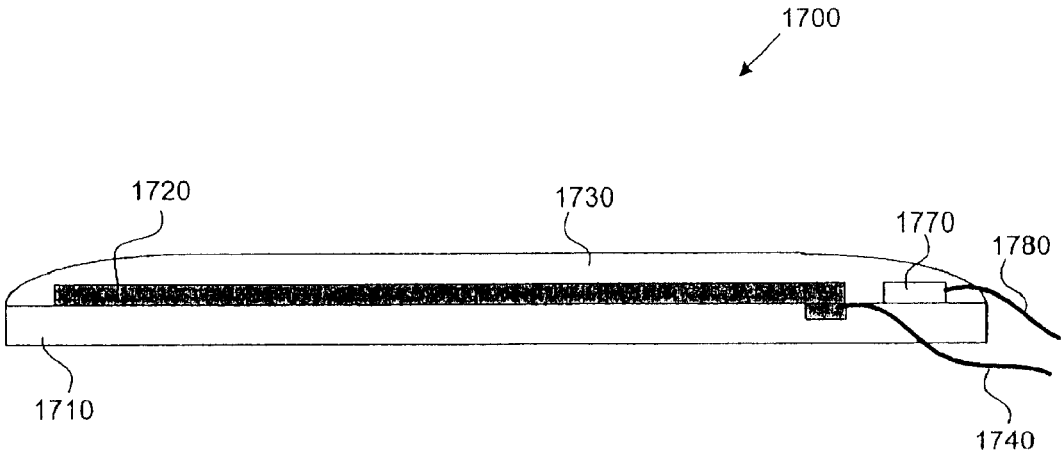
FIG. 17 is a cross sectional view of an electrode according to another embodiment of the invention.

Other electrode designs may facilitate electrical path characterization while mounted upon a release liner, in conjunction with determination of whether electrodes are mounted upon the release liner or a patient's body. FIG. 17 is a cross sectional view of an electrode 1700 according to another embodiment of the invention. The electrode 1700 may comprise a conductive adhesive material, conductive gel layer or hydrogel layer 1710, a foil layer 1720, an insulating layer 1730, and a first lead wire 1740, each of which may be implemented using conventional materials. The electrode 1700 further comprises a sonomicrometer 1770 coupled to a second lead wire 1780.

The sonomicrometer 1770 comprises a piezoelectric transducer capable of transmitting and/or receiving ultrasonic signals (i.e., sound signals having frequencies greater than or equal to 1 MHz). The sonomicrometer 1770 is positioned upon or partially embedded within the hydrogel layer 1710. A sonomicrometer 1770 may serve as an ultrasonic transmitter and/or an ultrasonic receiver. A sonomicrometer 1770 suitable for incorporation into an electrode 1700 may comprise a piezoelectric transducer available from Sonometrics Corporation (www.sonometrics.com). As described in detail hereafter, sonomicrometers 1770 incorporated into a group of electrodes 1700 may facilitate measurement of a separation distance between electrodes 1700, thereby determining or indicating whether electrodes 1700 are mounted upon a release liner or a patient's body.

Figure 18:
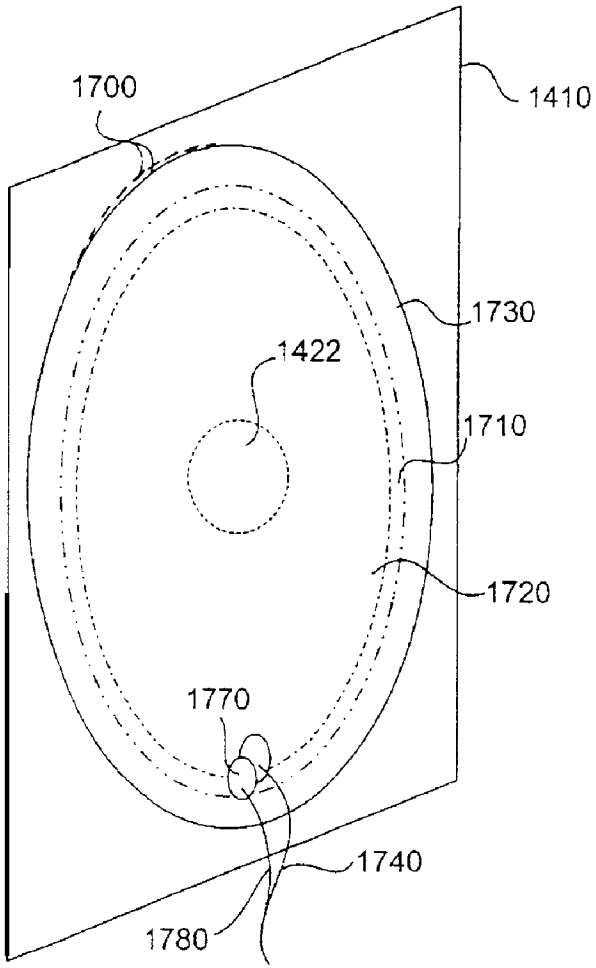
FIG. 18 is a perspective view of electrodes of FIG. 17 mounted upon the release liner of FIG. 14A.

FIG. 18 is a perspective view of electrodes 1700 of FIG. 17 mounted upon the release liner 1400 of FIG. 14A in accordance with an embodiment of the invention. Relative to FIGS. 14A and 17, like reference numbers indicate like elements. One electrode 1700 may be mounted upon one side of the release layer 1410, while another electrode 1700 may be mounted upon the release layer's opposite side. The release layer's opening 1422 facilitates hydrogel layer 1710 to hydrogel layer 1710 contact, thereby providing for direct electrical communication between electrodes 1700.

The first and second lead wires 1740, 1780 of each electrode 1700 may be coupled to a medical device. The medical device may electrically test or characterize the electrical path through one electrode's hydrogel layer 1710, through the release layer's opening 1422, and into the other electrode's hydrogel layer 1710. In the event that the medical device measures a short or open circuit condition, one or more electrodes 1700, lead wires 1740, and/or connectors that couple the electrodes 1700 to the medical device may be defective.

As the electrodes' hydrogel layers 1710 lose moisture over time, an impedance level or value associated therewith may increase. If the medical device measures an impedance value that exceeds a particular threshold or range, one or both electrodes 1700 may be non-optimal or unfit for use. The medical device may perform one or more operations and/or provide one or more indications of electrode condition in manners described in detail below.

The medical device may issue a separation measurement signal to one electrode's sonomicrometer 1770 via a second lead wire 1780. In response, the sonomicrometer 1770 may issue or generate an ultrasonic pulse, which may travel 1) through the signal generating electrode's hydrogel layer 1710; 2) through the release layer 1410 and/or the release layer's opening 1422; 3) and into the other electrode's hydrogel layer 1710, whereupon it may be detected and/or received by a receiving sonomicrometer 1770. The receiving sonomicrometer 1770 may issue a reception signal to the medical device in response to detection of the ultrasonic pulse.

The medical device may calculate or determine a separation distance between sonomicrometers 1770 based upon the time delay between issuance of the separation measurement signal and receipt of the reception signal, in a manner readily understood by those skilled in the art. Based upon the separation distance, the medical device may determine whether the electrodes 1700 are mounted upon the release liner 1400. A separation distance smaller than a given threshold distance, for example, one inch, provides an indication that the electrodes 1700 are mounted upon the release liner 1400 rather than a patient's body. In an alternate embodiment, a release liner 1400 itself may include a sonomicrometer 1770.

In the event that the medical device determines, calculates, or measures a separation distance significantly greater than that associated with electrodes 1700 mounted or packaged upon a release liner 1400, the medical device may determine that the electrodes 1700 are mounted upon a patient's body.

Based upon a measured or determined separation distance, the medical device may further determine whether the electrodes 1700 are properly positioned upon the patient's body. For example, the medical device may determine that the electrodes 1700 are positioned too close together, and provide a message to a medical device operator indicating such and/or requesting electrode repositioning. The medical device may further adjust, modify, or tailor a signal exchange sequence with the patient based upon a measured or determined electrode separation distance. For example, a medical device such as an AED may determine that a measured electrode separation distance indicates that the electrodes 1700 are mounted upon a large patient, and increase one or more shock energies accordingly.

In an alternate electrode embodiment, an electrode's foil layer 1720 may include an opening therein (not shown), in a manner analogous to that described above with reference to FIGS. 12A through 12C. The sonomicrometer 1770 may be situated or positioned within such an opening, in which case an ultrasonic signal may travel directly through one electrode's hydrogel layer 1710 into another electrode's hydrogel layer 1710 via the opening without experiencing significant signal attenuation due to the release layer 1410.

Figure 19:
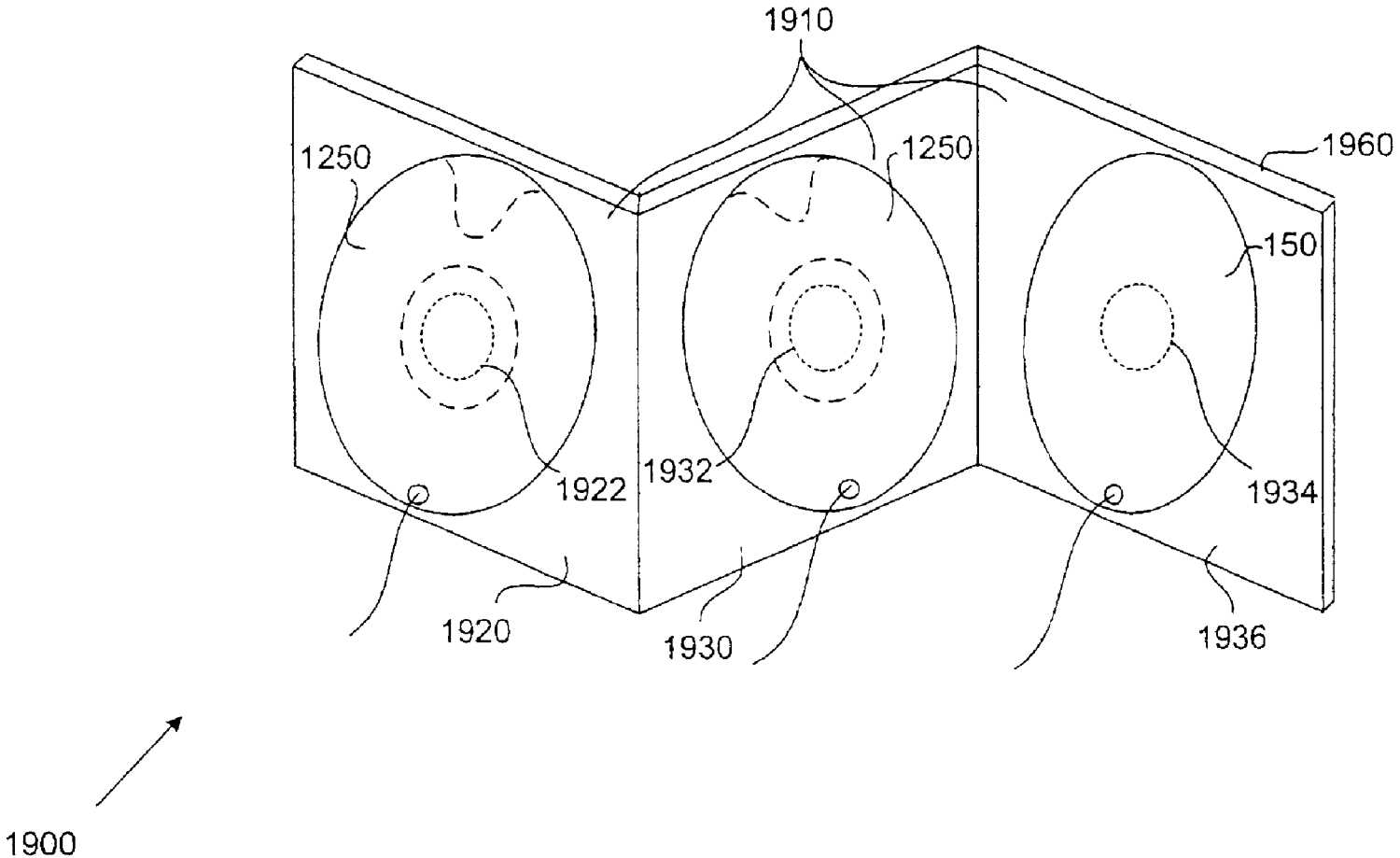
FIG. 19 is a perspective view of electrodes of FIG. 12C and a conventional electrode mounted upon a release liner according to another embodiment of the invention.

A wide variety of electrode/release liner configurations in addition those disclosed above may exist. FIG. 19 is a perspective view of voided electrodes 1250 of FIG. 12C and a conventional electrode 150 mounted upon a release liner 1900 in accordance with another embodiment of the invention. The release liner 1900 may comprise a foldable release layer 1910 and a conductive backing layer 1960. The foldable release layer 1910 may comprise a nonconductive, non-stick material having a first mounting or release portion 1920, a second mounting or release portion 1930, and a third mounting or release portion 1936. The first, second, and third mounting portions 1920, 1930, 1936 may respectively include first a set of openings 1922, a second set of openings 1932, and a third set of openings 1938 therein. The first and second mounting portions 1920, 1930 may be separated by a first fold region 1940, while the second and third mounting portions 1930, 1936 may be separated by a second fold region 1942. The foldable release layer 1910 may be implemented using conventional materials, such as those described above, and the first, second, and/or third sets of openings 1922, 1932, 1938 may be cut, stamped, and/or punched out of such materials in conventional manners.

The conductive backing layer 1960 may comprise a foldable or bendable sheet or layer of conductive material, such as an Aluminum or Tin foil layer. Depending upon embodiment and/or implementation details, the conductive backing layer 1960 may be adhered, laminated, and/or otherwise attached to the release layer 1910. Additionally or alternatively, the conductive backing layer 1960 may be held in position via adhesion to hydrogel in regions in which the first, second and/or third sets of release layer openings 1922, 1932, 1938 expose the backing layer 1960 to electrodes 1250, 150 mounted upon the release layer 1910.

Electrodes 1250, 150 may be mounted upon each of the foldable release layer's mounting portions 1920, 1930, 1936, for example, in the manner shown in FIG. 19. Electrodes 1250, 150 mounted in such a manner reside upon a single side of the foldable release layer 1910; that is, electrodes 1250, 150 so mounted reside upon the same surface of the foldable release layer 1910. The foldable release layer 1910 may be folded, bent, or doubled about one or more fold regions 1940, 1942.

A medical device to which the electrodes 1250 are coupled may test and/or characterize the electrical path between any pair of electrodes 1250, 150 and/or all electrodes 1250, 150 in a manner analogous to that described above. The medical device may provide one or more indications of electrical path and/or electrode condition in manners described in detail below.

Those skilled in the art will understand that other electrode/release liner configurations may include conventional electrodes 150; voided electrodes 1200, 1250 in accordance with FIGS. 12A, 12B, and 12C; electrodes 1260 having one or more swatches 1226 incorporated therein in a manner analogous to that described above with reference to FIGS. 12D and 12E; sonomicrometer electrodes 1700; and/or other electrodes. Release liners upon which such electrodes may be mounted may include can appropriate set of openings to facilitate electrical communication between electrodes in manners analogous to those described above.

The release liner and/or electrode embodiments described above facilitate electrical characterization of packaged electrodes via electrical contact between electrodes. Release liner and/or electrode embodiments that facilitate such characterization via measurements that may not rely upon electrode to electrode contact are considered in detail hereafter.

Figure 20:
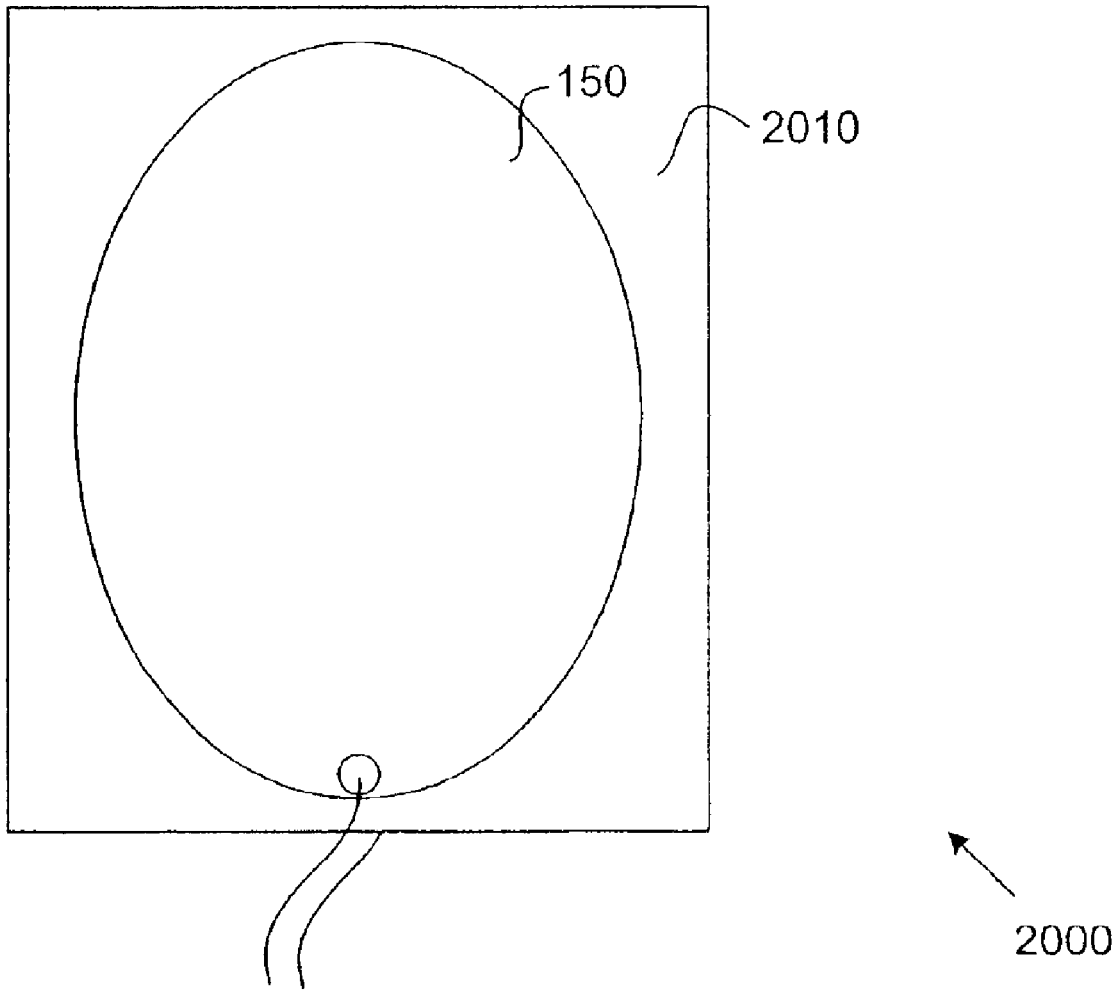
FIG. 20 is a perspective view of electrodes mounted upon a release liner in accordance with another embodiment of the invention.

FIG. 20 is a perspective view of electrodes 150 mounted upon a release liner 2000 in accordance with an embodiment of the invention. The release liner 2000 may comprise a release layer 2010 having two sides and characterized by nonconductive and non-stick properties. The release layer 2010 may be characterized by a known thickness and dielectric constant, may be implemented using a variety of conventional materials including those described above.

One electrode 150 may be positioned or mounted upon one side of the release layer 2010, while another electrode may be analogously positioned upon the release layer's other side. For a given electrode 150, the effective electrical contact area to the release layer 2010 may correspond to the area spanned by the electrode's hydrogel layer. Alternatively, the effective electrical contact area to the release layer 2010 may be a function of the area of the electrode's hydrogel layer relative to that of the electrode's foil layer.

The electrical contact area associated with each electrode 150, as separated by a release layer having a known thickness and dielectric constant, forms a type of parallel plate capacitor. A medical device coupled to electrodes 150 mounted upon a release liner 2000 in the manner shown in FIG. 20 may therefore measure, determine, or calculate a corresponding capacitance value. In one embodiment, the thickness and capacitance associated with the release liner are approximately 5 mils and 1 nF, respectively. The effective electrical contact area may be approximately 100 square centimeters.

If the capacitance value is above or below a predetermined or expected range, a short or open circuit condition may exist, possibly indicating a damaged or defective electrical path, possibly arising from a problem with an electrode 150, wiring, and/or a connector. In such a situation, the medical device may provide an indication that the packaged electrodes 150 are unfit for use, possibly in manners described in detail below.

A medical or measuring device may alternatively or additionally perform a complex impedance measurement upon electrodes 150 mounted upon a release liner 2000 as shown in FIG. 20. A complex impedance may be characterized by a real impedance R (i.e., a resistance); and an imaginary impedance X (i.e., a reactance in the context of the present invention). When electrodes 150 are mounted upon a release liner 2000, a real impedance may correspond to hydrogel layer moisture content, and an imaginary impedance may correspond to a capacitance within the electrode/release liner configuration.

As the electrodes' hydrogel layers lose moisture over time, the medical or measuring device may measure a corresponding increase in a real impedance R. The medical or measuring device may include temperature measurement and/or compensation circuitry or elements to account for manners in which measured impedance levels may vary as a function of temperature. If the medical or measuring device determines that a temperature compensated real impedance value exceeds a given threshold value and/or falls outside an acceptable range, one or more electrode's hydrogel layers may have dried out to an extent that such electrodes 150 are no longer optimal or fit for use. The medical or measuring device may provide an indication of such, possibly in manners described in detail below.

The magnitude of a real impedance R relative to that of an imaginary impedance X may determine an extent to which a medical device can detect or determine a hydrogel layer's condition. In the embodiment shown in FIG. 20, an imaginary impedance X may dominate complex impedance measurements. Thus, small changes in a real impedance R may be difficult to detect, making accurate and/or detailed characterization of electrode hydrogel layer condition correspondingly difficult.

Electrode and/or release liner structure may have a significant impact upon the magnitude of a real impedance R relative to that of an associated imaginary impedance X. In particular, release liner and/or electrode structures that minimize an imaginary impedance X and/or maximize a real impedance R may facilitate determination of more detailed information about hydrogel layer condition. Release liner and/or electrode embodiments directed toward maximizing detectability of changing hydrogel layer conditions are described in detail hereafter.

Figure 21A:
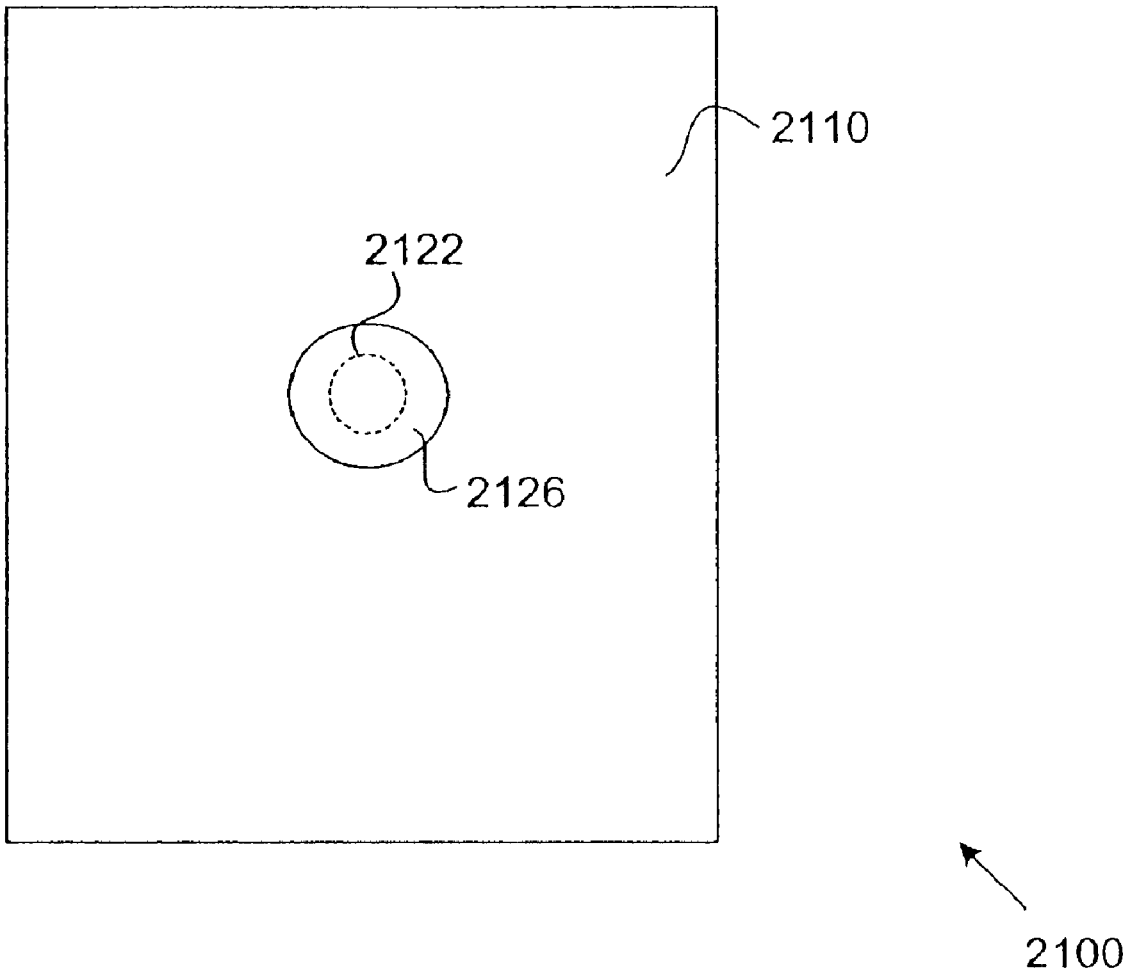
FIG. 21A is a plan view of a release liner according to another embodiment of the invention.

FIG. 21A is a plan view of a release liner 2100 according to an embodiment of the invention. In the embodiment shown, the release liner 2100 comprises a two-sided release layer 2110 having an opening 2122 therein; and an insulating swatch or patch 2126 that covers or fills the opening 2122. The release layer 2110 may comprise a conventional nonconductive, non-stick material, in a manner described above. The insulating swatch 2126 may comprise a thin layer of nonconductive material characterized by a high dielectric constant. The swatch 2126 may be implemented, for example, using Polyvinyl Chloride (PVC), which typically exhibits a dielectric constant ranging between 4.8 and 8; Polyvinlidene fluoride (PVDF), which may exhibit a dielectric constant ranging between 8 and 10; a ceramic material such as $BaTiO_3$, which may exhibit a dielectric constant ranging between 350 and 6500; and/or other materials. The thickness of the swatch 2126 in any given implemented may depend upon manufacturing and/or material handling considerations. Polymeric swatches 2126 may comprise one or more film-based layers, and may have a thickness of 1 mil or less. Ceramic-based swatches 2126 may exhibit a thickness range, for example, between 2 and 10 mils.

Figure 21B:
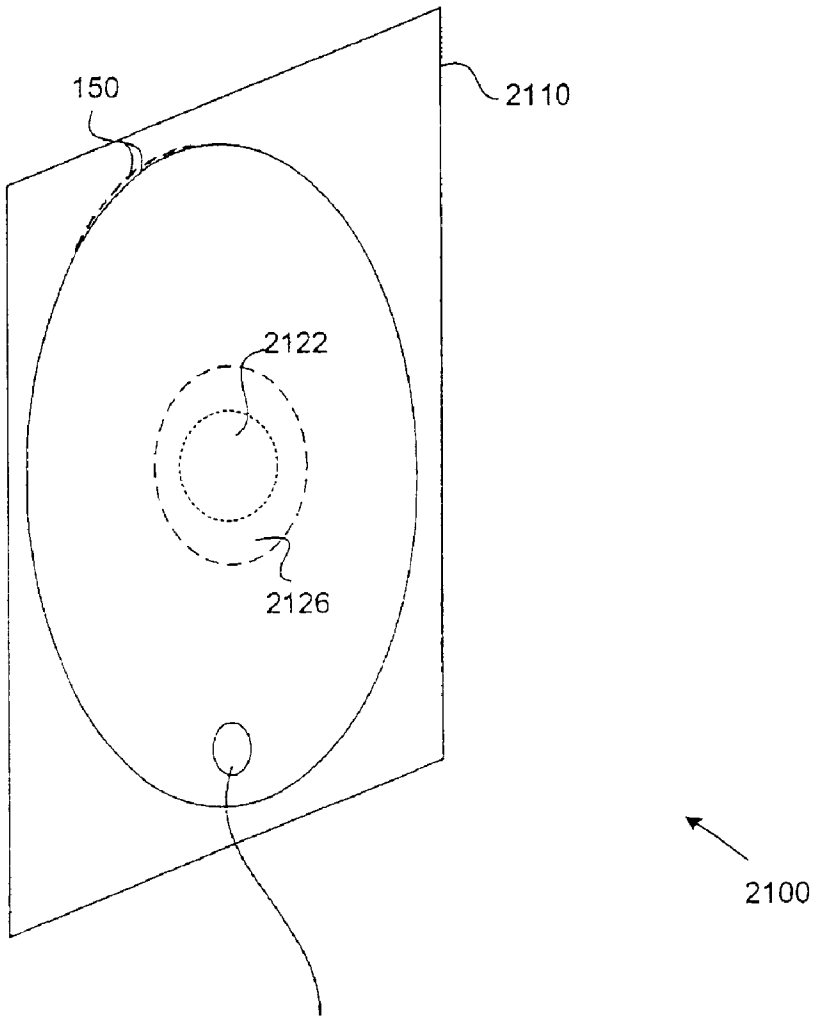
FIG. 21B is a perspective view of electrodes mounted upon the release liner of FIG. 21A.

FIG. 21B is a perspective view of electrodes 150 mounted upon the release liner 2100 of FIG. 21A. One electrode 150 may be positioned upon one side of the release layer 2110, while the other electrode 150 may be positioned upon the release layer's other side, forming an electrode 150 to release liner 2100 to electrode 150 assembly 2102. A medical or measurement device to which the electrodes 150 are coupled may perform a complex impedance measurement upon the assembly 2102.

Figure 21C:
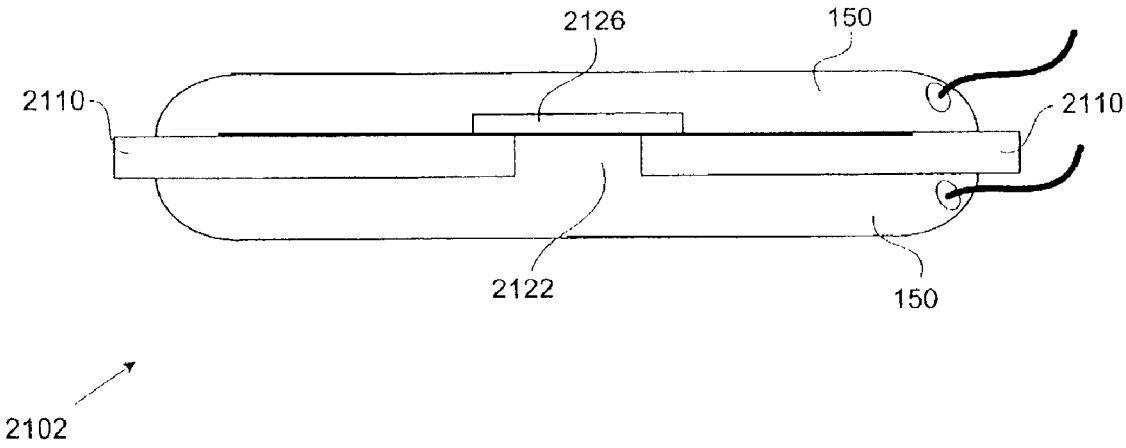
FIG. 21C is a cross sectional view of an electrode to release liner assembly of FIG. 21B.
Figure 21D:
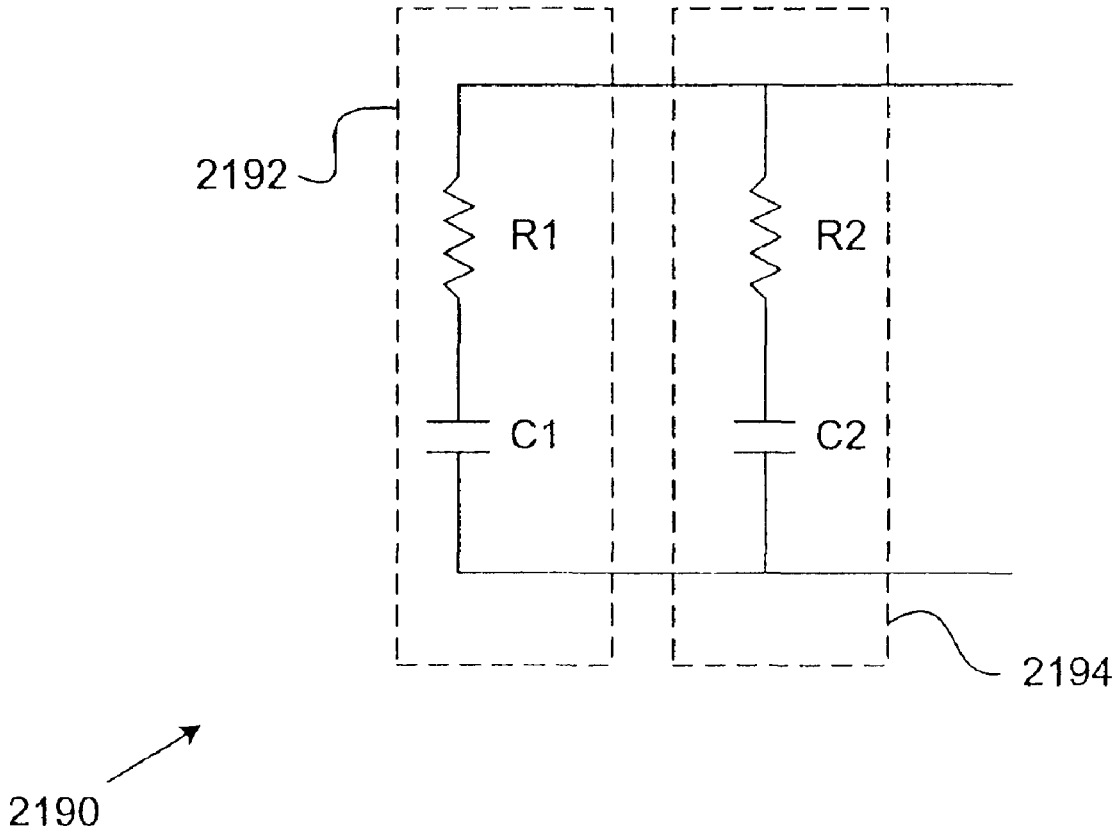
FIG. 21D is an equivalent circuit corresponding to the electrode to release liner assembly of FIG. 21B.

FIG. 21C is a cross sectional view of the electrode to release liner to electrode assembly 2102 of FIG. 21B. FIG. 21D is an equivalent circuit 2190 corresponding to or modeling the assembly 2102 of FIG. 21B. The equivalent circuit 2190 may be characterized by a first circuit branch 2192 in parallel with a second circuit branch 2194. The first circuit branch 2192 includes a first resistance R1 and a first capacitance C1, and may be characterized by a first impedance Z1. Impedance Z1 may be decomposed or represented as R1+X1, where X1 is a reactance associated with capacitance C1, equal to $1/(j\omega C1)$. The second circuit branch 2194 includes a second resistance R2 and a second capacitance C2, and may be characterized by a second impedance Z2. Impedance Z2 may be represented as R2+X2, where X2 is a reactance associated with capacitance C2, equal to $1/(j\omega C2)$.

The first circuit branch 2192 may correspond to a displacement current path that excludes an area in which the swatch 2126 covers, fills, overlaps, and/or blocks the release layer's opening 2122. That is, the first circuit branch 2192 may correspond to a displacement current path outside a boundary defined by an area in which the swatch 2126 covers the opening 2122. This displacement current path may exist through one electrode's conductive foil and hydrogel layers, the release layer 2110 (and possibly portions of the swatch 2126 that extend beyond a boundary defined by the opening 2122), and the other electrode's conductive foil and hydrogel layers. Thus, within the first circuit branch 2192, resistance R1 may correspond to an effective conductive and hydrogel layer resistance within the electrodes 150 in areas excluding those in which the swatch 2126 covers the opening 2122. Similarly, capacitance C1 may correspond to an effective capacitance of the release layer 2110 in areas excluding those in which the swatch 2126 covers the opening 2122.

The second circuit branch 2194 may correspond to a displacement current path through areas or portions of the swatch 2126 that cover or fill the opening 2122. That is, the second circuit branch 2194 may correspond to the displacement current path from one electrode's conductive foil and hydrogel layers in an area in which the swatch 2126 covers the opening 2122; through the swatch 2126 where it covers or fills the opening 2122; and into the other electrode's conductive and hydrogel layers in this area. Thus, within the second circuit branch 2194, resistance R2 may correspond to an effective conductive and hydrogel layer resistance associated with the electrodes 150 in an area of the swatch 2126 where it covers the opening 2122, while capacitance C2 may correspond to an effective capacitance associated with the swatch 2126 in or over an area defined by the opening 2122.

An effective impedance $Z_{eff}$ may be defined as $((1/Z1)+(1/Z2)^{-1}$, in a manner readily understood by those skilled in the art. Those skilled in the art will also understand that an effective current $I_{eff}$ may thus vary in accordance with $((1/Z1)+(1/Z2))$, or $(1/(R1+X1)+1/(R2+X2))$. For electrodes 150 in good condition, the values of resistances R1 and R2 may generally be small. Capacitance C2 may be significantly larger than capacitance C1, and hence reactance X2 is correspondingly smaller than reactance X1. Additionally, reactance X2 may be sufficiently small that it does not overwhelm or dominate the term $1/(R2+X2)$. Neither X1 nor X2 generally experience significant changes over time. Hence, changes in resistance R2 over time, which may correspond to changes in hydrogel layer moisture content, may noticeably affect the complex impedance of the assembly 2102. Other electrode/release liner configurations or embodiments in which changes in hydrogel layer properties may significantly affect complex impedance measurements are described in detail hereafter.

Figure 22A:
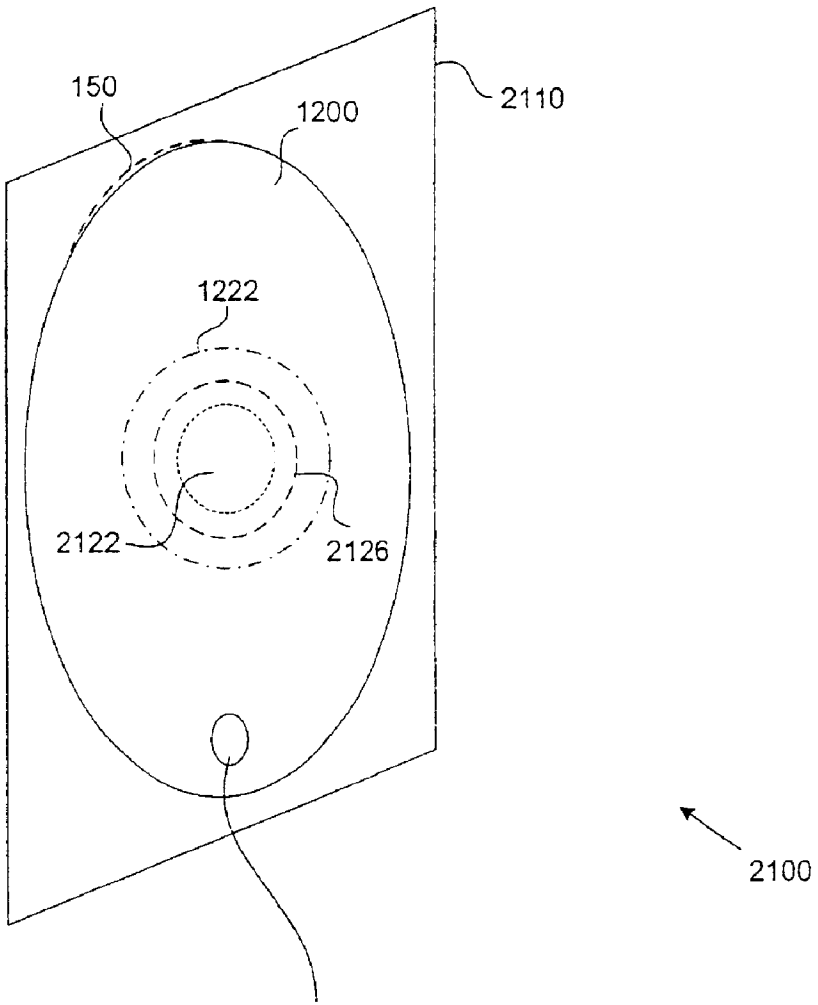
FIG. 22A is a perspective view of an electrode of FIG. 12A and a conventional electrode mounted upon the release liner of FIG. 21A.

FIG. 22A is a perspective view of a voided electrode 1200 of FIG. 12A and a conventional electrode 150 mounted upon the release liner 2100 of FIG. 21A. Relative to FIGS. 12A and 21A, like reference numbers indicate like elements. The voided electrode 1200 may be mounted upon one side of the release layer 2110, while the conventional electrode 150 may be mounted upon the release layer's other side, forming a voided electrode 1200 to release liner 2100 to conventional electrode 150 assembly 2102. The voided electrode 1200 may be mounted or positioned such that its void 1222 surrounds or encompasses at least a portion of the release liner's swatch 2126, namely, that portion of the swatch 2126 that covers, fills, and/or overlaps the release layer's opening 2122. Those skilled in the art will understand that the area occupied by the void 1222 may be larger or smaller than that occupied by the swatch 1226. The conventional electrode 150 may be positioned such that its hydrogel layer covers the release layer's opening 2122. Those skilled in the art will also understand that either of the voided or conventional electrodes 1200, 150 may be mounted upon the side of the release liner 2100 upon which the swatch 2126 resides.

Figure 22B:
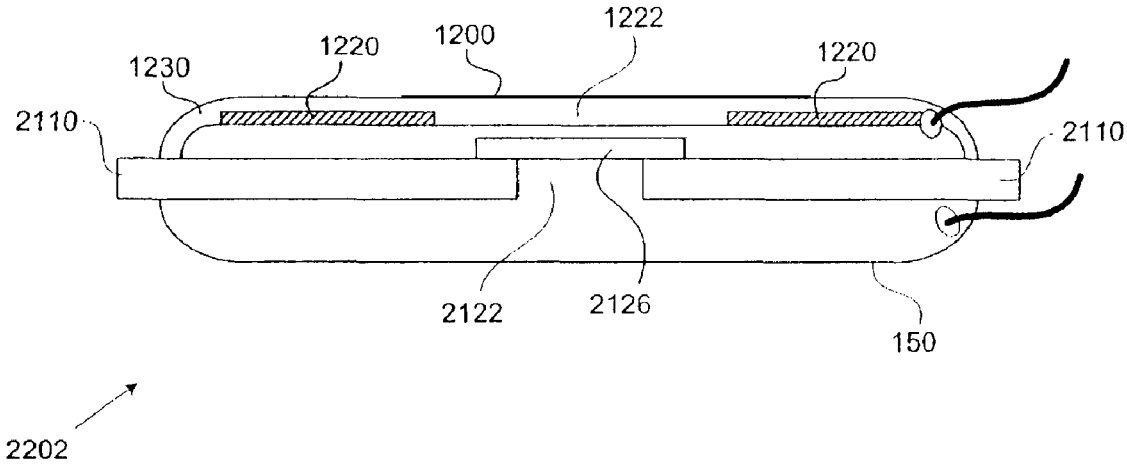
FIG. 22B is a cross sectional view of a voided electrode to release liner to conventional electrode assembly of FIG. 22A.
Figure 22C:
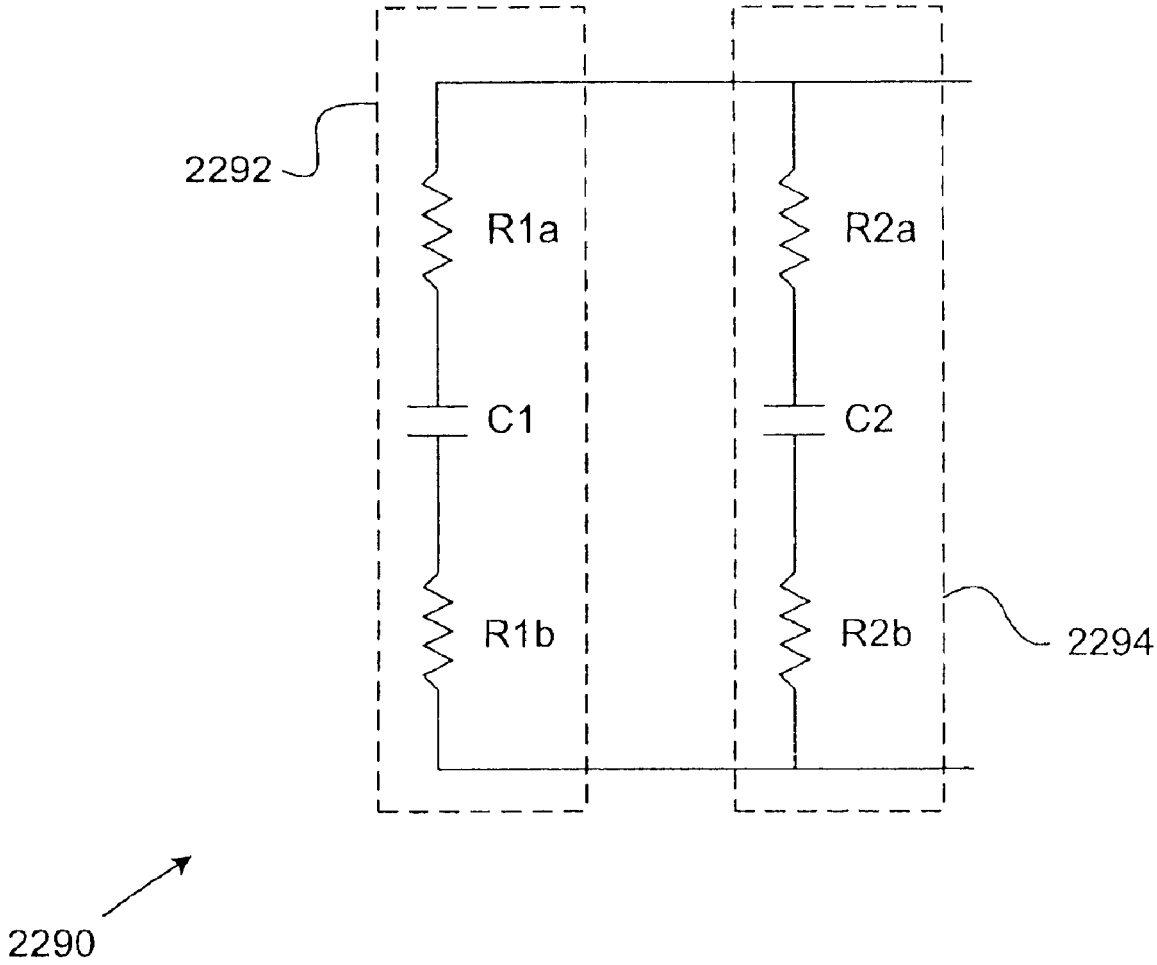
FIG. 22C is an equivalent circuit corresponding to the voided electrode to release liner to conventional electrode assembly of FIG. 22A.

FIG. 22B is a cross sectional view of the voided electrode 2100 to release liner 2100 to conventional electrode 150 assembly 2202, and FIG. 22C is an equivalent circuit 2290 corresponding to or modeling the assembly 2202 of FIG. 22A. In the equivalent circuit 2290, a first circuit branch 2292 may correspond to a displacement current path outside a boundary defined by the release liner's swatch 2126 where it covers, fills, and/or blocks opening 2122, in a manner analogous to that described above. Similarly, a second circuit branch 2294 may correspond to a displacement current path through an area or region in which the swatch 2126 covers, fills, and/or blocks the opening 2122, in a manner analogous to that described above.

The first circuit branch 2292 may include a resistance R1a, a capacitance C1, and a resistance R1b, and may be characterized by an impedance Z1. Resistance R1a may correspond to an effective resistance of the voided electrode's conductive foil areas and hydrogel layers 1220, 1210 exclusive of areas in which the swatch 2126 covers, fills, and/or blocks the opening 2122. Resistance R1b may correspond to an effective resistance of the conventional electrode's conductive foil and hydrogel layers exclusive of areas in which the swatch 2126 covers the opening 2122. Capacitance C1 may correspond to an effective capacitance of the release layer 2110 in areas excluding those in which the swatch 2126 covers the opening 2122, and may be accounted for as a reactance X1. Impedance Z1 may be decomposed or represented as R1a+X1+R1b, in a manner analogous to that described above.

The second circuit branch 2294 may include a resistance R2a, a capacitance C2, and a resistance R2b, and may be characterized by an impedance Z2. Resistance R2a may correspond to an effective resistance of the voided electrode's hydrogel layer 1210 in areas associated with the release liner's swatch 2126 where it covers, fills, and/or blocks the opening 2122 (i.e., an effective resistance of the voided electrode's hydrogel layer 1210 in an area in which the void 1222, the hydrogel layer 1210, the swatch 2126, and the opening 2122 may be coincident). Resistance R2b may correspond to an effective resistance of the conventional electrode's conductive foil and hydrogel layers in areas in which swatch 2126 covers the opening 2122. Capacitance C2 may correspond to an effective capacitance of the swatch 2126 in an area or region in which the swatch 2126 covers, fills, overlaps, and/or blocks the opening 2122, and may be accounted for as a reactance X2. Impedance Z2 may be decomposed or represented as R2a+X2+R2b, in a manner analogous to that described above.

In a manner analogous to that describe above, an effective impedance $Z_{eff}$ may be defined as $((1/Z1)+(1/Z2))^{-1}$. Capacitance C2 may be significantly larger than capacitance C1 (i.e., C2>>C1); hence, reactance X2 is correspondingly much smaller than reactance X1. As a result, the second circuit branch 2294 provides a dominant current path relative to the first circuit branch 2292. Furthermore, reactance X2 may be sufficiently small that it does not overwhelm or dominate the term 1/(R2a+X2+R2b). Neither X1 nor X2 generally experience significant changes over time.

R2a may correspond to a lateral or transverse current path through the voided electrode's hydrogel layer 1210. As a result, R2a may be significantly larger than R2b. Moreover, R2a may exhibit a magnitude that is approximately equal to or in the same range as that of X2. As a result, changes in R2a over time, which may correspond to changes in the condition of the voided electrode's hydrogel layer 1210 over time, may significantly impact the effective impedance of the voided electrode 1200 to release layer 2100 to conventional electrode 150 assembly 2202. Via measuring complex impedance measurement results over time, a medical device may determine an extent to which a voided electrode 1200 and/or a conventional electrode 150 mounted upon the release liner 2100 of FIG. 21A are optimal and/or fit for use. The medical device may provide an indication of electrode condition in manners described in detail below.

Figure 23A:
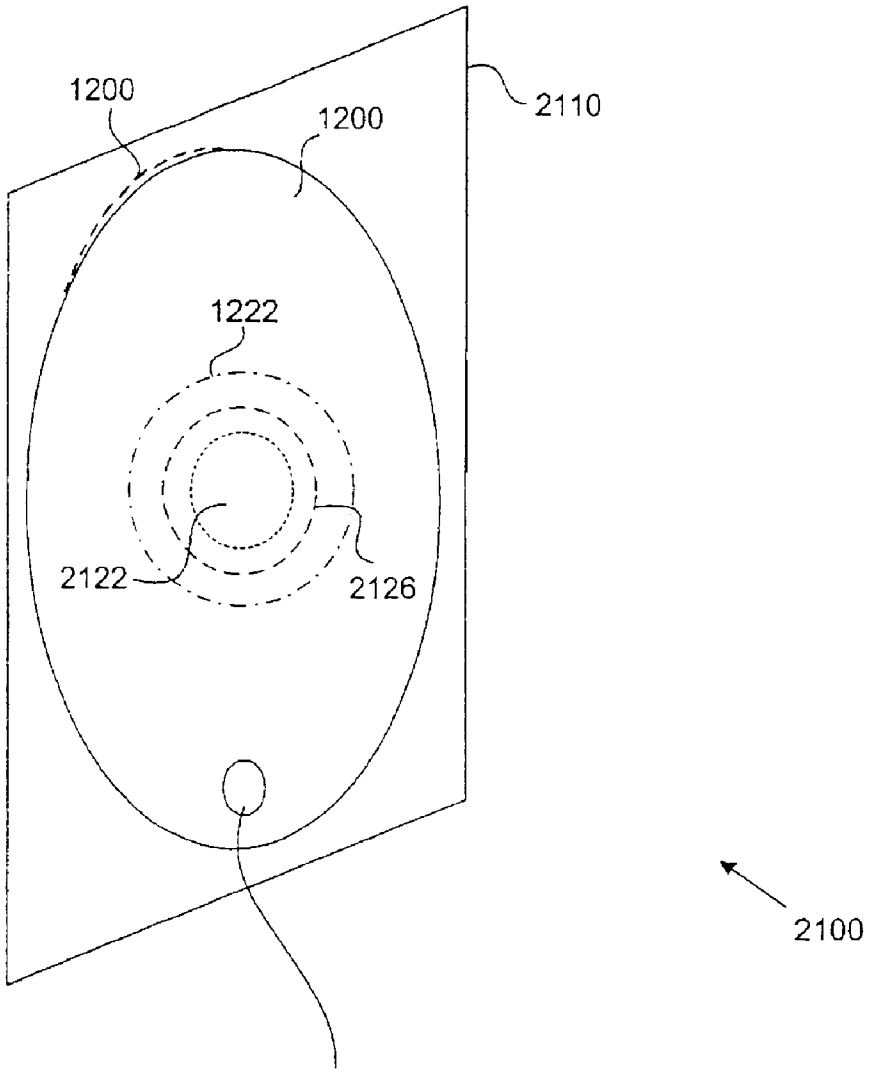
FIG. 23A is a perspective view of electrodes of FIG. 12A mounted upon the release liner of FIG. 21A.

FIG. 23A is a perspective view of a pair of voided electrodes 1200 of FIG. 12A mounted upon the release liner 2100 of FIG. 21A. Relative to FIGS. 12A and 21A, like reference numbers indicate like elements. The voided electrodes 1200 may be mounted upon each side of the release layer 2110, thereby forming a voided electrode 1200 to release liner 2100 to voided electrode 1200 assembly 2302. One voided electrode 1200 may be mounted or positioned such that its void 1222 surrounds or encompasses the release liner's swatch 2126 in an area or region in which the swatch 2126 covers or fills the release layer's opening 2122. Another voided electrode 1200 may be positioned on another side of the release layer 2110, such that its void 1222 surrounds the release layer's opening 2122.

Figure 23B:
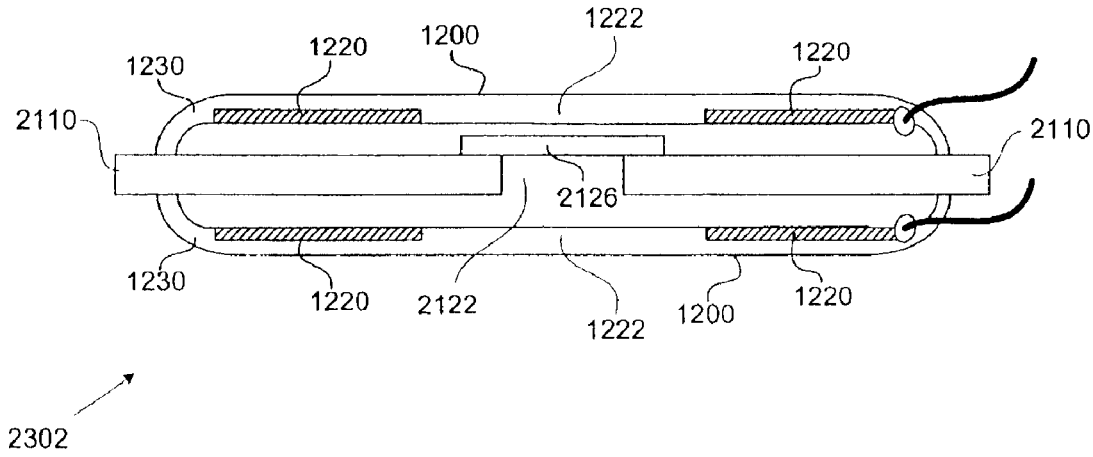
FIG. 23B is a cross sectional view of a voided electrode to release liner to voided electrode assembly of FIG. 23A.
Figure 23C:
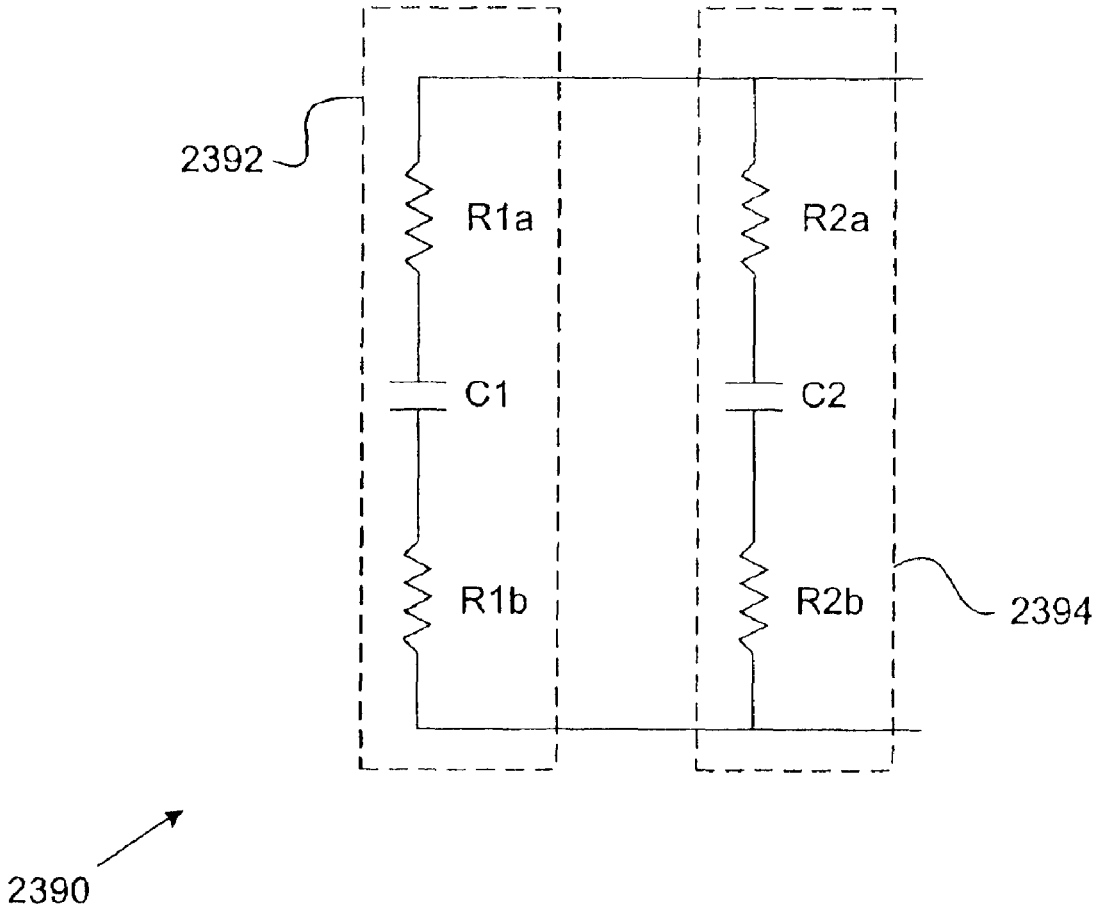
FIG. 23C is an equivalent circuit corresponding to the voided electrode to release liner to voided electrode assembly of FIG. 23A.

FIG. 23B is a cross sectional view of the voided electrode 1200 to release liner 2100 to voided electrode 1200 assembly 2302 of FIG. 23A, and FIG. 23C is an equivalent circuit 2390 corresponding to or modeling the assembly 2302 of FIG. 23A. In the equivalent circuit 2390, a first circuit branch 2392 may correspond to a displacement current path outside a boundary defined by the release liner's swatch 2126 where it covers, fills, and/or blocks opening 2122, in a manner analogous to that described above. Similarly, a second circuit branch 2394 may correspond to a displacement current path through an area or region in which the swatch 2126 covers, fills, and/or blocks the opening 2122, in a manner analogous to that described above.

The first circuit branch 2392 may include a resistance R1a, a capacitance C1, and a resistance R1b, and may be characterized by an impedance Z1. Resistances R1a and R1b may correspond to an effective resistance of a given voided electrode's conductive foil and hydrogel layers 1220, 1210 exclusive of areas in which the swatch 2126 covers, fills, and/or blocks the opening 2122. Capacitance C1 may correspond to an effective capacitance of the release layer 2110 in areas excluding those in which the swatch 2126 covers the opening 2122, and may be accounted for as a reactance X1. Impedance Z1 may be decomposed or represented as R1a+X1+R1b, in a manner analogous to that described above.

The second circuit branch 2394 may include a resistance R2a, a capacitance C2, and a resistance R2b, and may be characterized by an impedance Z2. Resistances R2a and R2b may correspond to an effective resistance of a given voided electrode's hydrogel layer 1210 in areas associated with the release liner's swatch 2126 where it covers, fills, and/or blocks the opening 2122, in a manner analogous to that previously described. Capacitance C2 may correspond to an effective capacitance of the swatch 2126 in an area or region in which it covers, fills, overlaps, and/or blocks the opening 2122, and may be accounted for as a reactance X2. Impedance Z2 may be decomposed or represented as R2a+X2+R2b, in a manner analogous to that described above.

In a manner analogous to that describe above, an effective impedance $Z_{eff}$ may be defined as $((1/Z1)+(1/Z2))^{-1}$, and an effective current $I_{eff}$ may thus vary in accordance with ((1/Z1)+(1/Z2)), or (1/(R1a+X1+R1b)+1/(R2a+X2+R2b)). Capacitance C2 may be significantly larger than capacitance C1, and hence reactance X2 is correspondingly smaller than reactance X1. Additionally, reactance X2 may be sufficiently small that it does not overwhelm or dominate the term 1/(R2a+X2+R2b). Neither X1 nor X2 generally experience significant changes over time.

In the assembly 2302 of FIGS. 23A and 23B, resistances R2a and R2b may correspond to lateral current paths through a hydrogel layer 1210. Moreover, R2a and R2b may each exhibit a magnitude that is approximately equal to or in the same range as that of X2. As a result, changes in R2a and R2b over time, which may correspond to changes in the condition of the voided electrodes' hydrogel layers 1210 over time, may significantly impact the effective impedance of the voided electrode 1200 to release layer 2100 to voided electrode 1200 assembly 2302. Via measuring and/or recording complex impedance over time, a medical or measurement device may determine an extent to which a voided electrode 1200 and/or a conventional electrode 150 mounted upon the release liner 2100 of FIG. 21A are optimal and/or fit for use. The medical device may provide an indication of electrode condition in manners described in detail below.

Figure 24A:
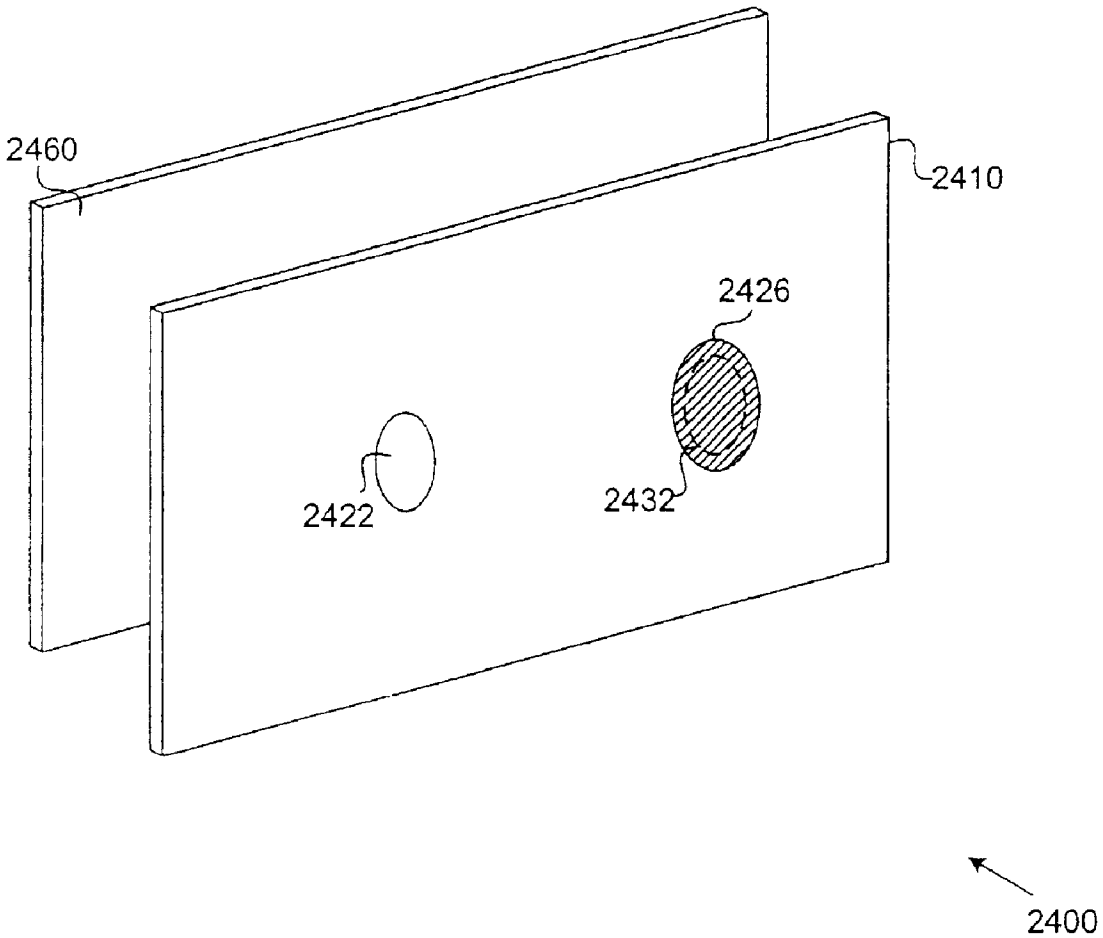
FIG. 24A is a layered plan view of a release liner according to another embodiment of the invention.

FIG. 24A is a layered plan view of a release liner 2400 according to another embodiment of the invention. The release liner 2400 comprises a nonconductive, non-stick release layer 2410 and a conductive backing layer 2460. The release layer 2410 includes a first opening 2422, a second opening 2432, and a nonconductive swatch 2426 that covers, fills, overlaps, and/or blocks one of the openings 2422, 2432. The release layer 2410 and/or the conductive backing layer 2460 may be implemented using materials previously described. The first and second openings 2422, 2432 may be cut, stamped, or punched out of the release layer 2410 in a conventional manner. In an alternate embodiment, one or both of the first and second openings 2422, 2432 may comprise sets of openings. Finally, the swatch 2426 may comprise a thin material characterized by a high or generally high dielectric constant, such as a polymeric and/or ceramic material described above.

The conductive backing layer 2460 may be adhered, laminated, and/or otherwise attached to the release layer 2410, thereby maintaining or holding the backing layer 2460 in a given position. Additionally or alternatively, the conductive backing layer 2460 may be held in position by adhesion between the conductive backing layer 2460 and electrodes' hydrogel layers in regions defined by the release layer's openings 2422, 2432.

Figure 24B:
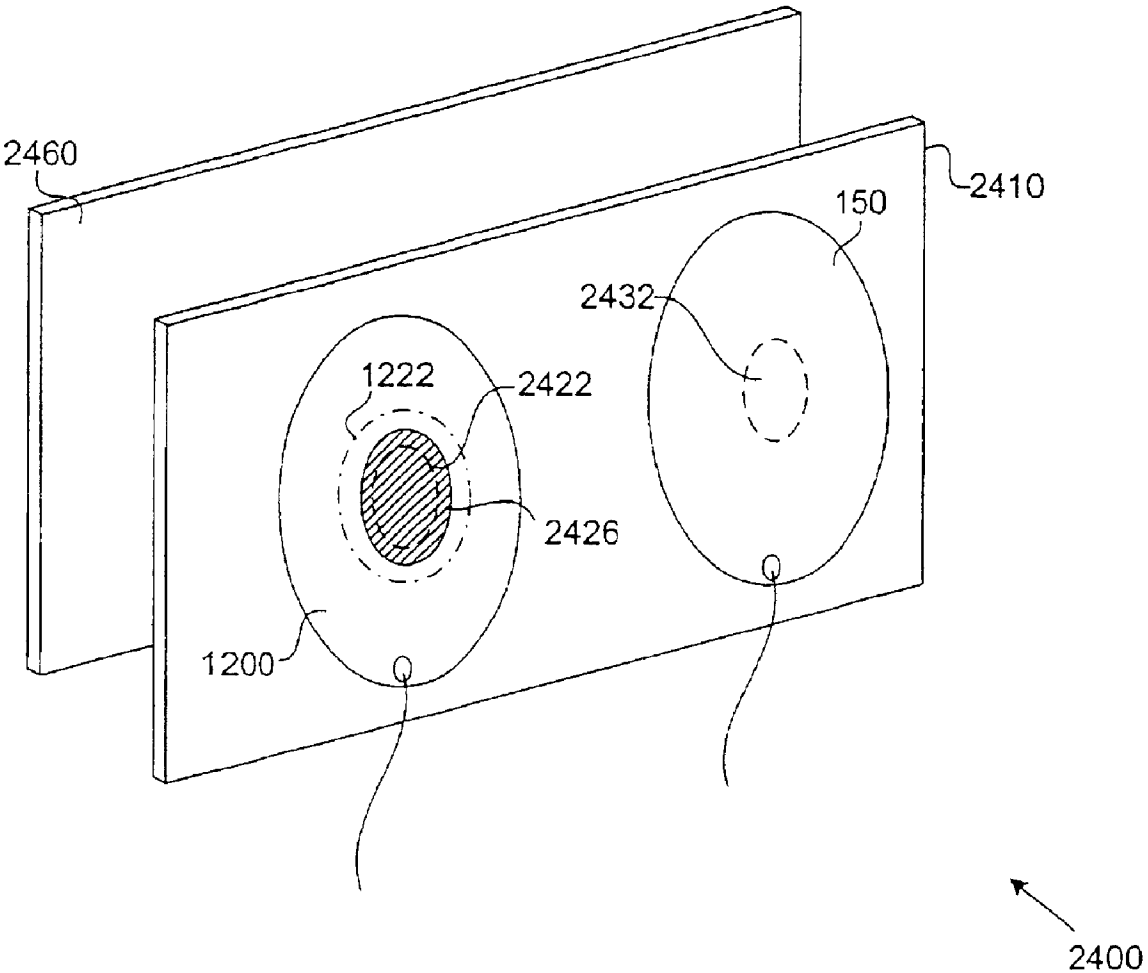
FIG. 24B is a plan view of a conventional electrode and an electrode of FIG. 12A mounted upon the release liner of FIG. 24A.

FIG. 24B is a plan view of a conventional electrode 150 and a voided electrode 1200 of FIG. 12 mounted upon the release liner 2400 of FIG. 24A. Relative to FIGS. 12 and 24A, like reference numbers indicate like elements. The voided electrode 1200 may be mounted upon the release layer 2410 such that its void 1222 surrounds the release layer's first opening 2422, thereby surrounding at least a portion of the swatch 2426. The conventional electrode 150 may be mounted upon the release layer 2410 such that its hydrogel layer covers the second opening 2422.

A medical or measurement device to which the voided and conventional electrodes 1200, 150 are coupled may perform a complex impedance measurement in a manner analogous to that describe above with respect to FIGS. 22A and 22B. Based upon the result of the impedance measurement, the medical or measurement device may provide an indication of electrical path condition and/or electrode condition or fitness for use, in manners described in detail below.

Figure 25A:
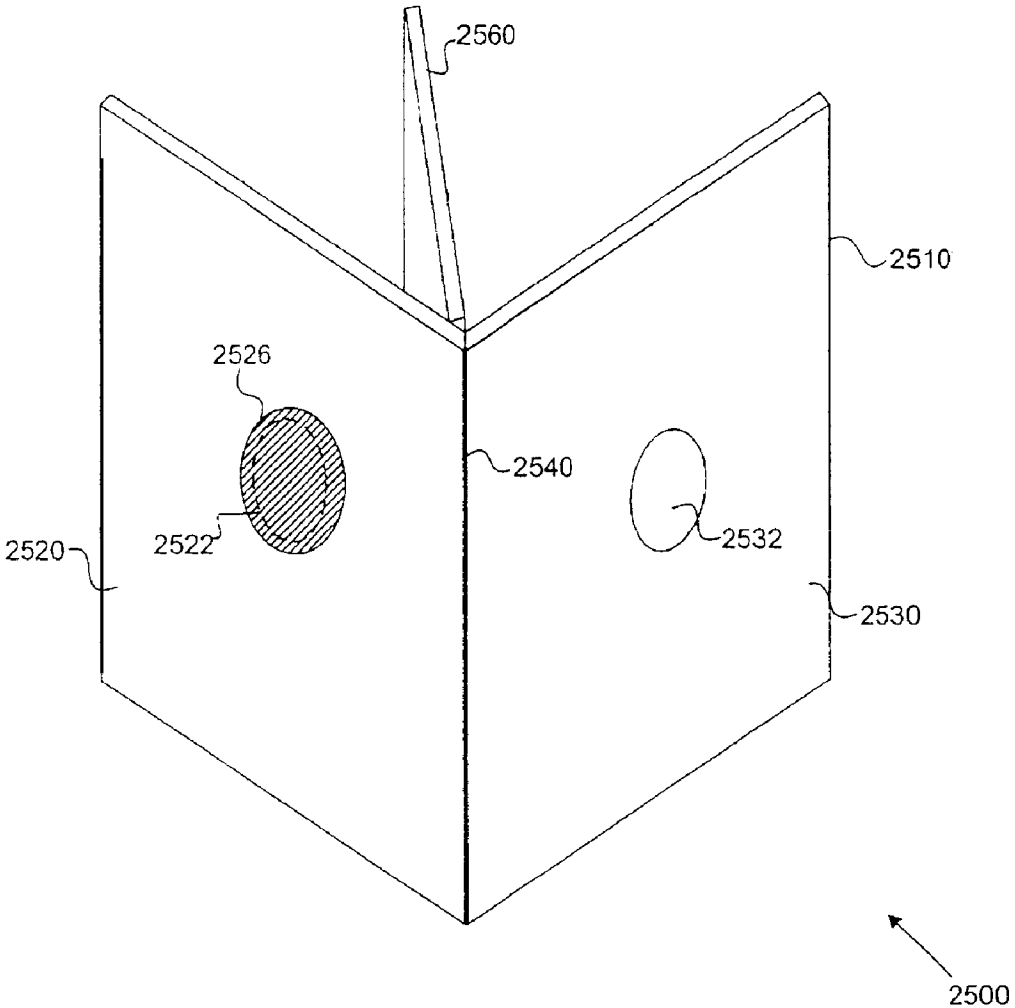
FIG. 25A is a plan view of a release liner according to another embodiment of the invention.

FIG. 25A is a plan view of a release liner 2500 according to another embodiment of the invention. The release liner 2500 comprises a foldable release layer 2510 and a conductive backing layer 2560. The foldable release layer 2510 may comprise a nonconductive, non-stick material such as those previously described. The foldable release layer 2510 includes a first mounting portion 2520 having a first opening 2522; a second mounting portion 2530 having a second opening 2532; a nonconductive swatch 2526 that covers, fills, overlaps, and/or blocks the first openings 2522; and a fold or midline region 2540. The first and second openings 2522, 2532 may be cut, stamped, or punched out of the release layer 2510 in a conventional manner. In an alternate embodiment, one or both of the first and second openings 2522, 2532 may comprise sets of openings. The conductive backing layer 2560 may be implemented using conventional materials in a manner analogous to that described above. Finally, the swatch 2526 may comprise a thin material characterized by a high or generally high dielectric constant, such as a polymeric and/or ceramic material described above.

The foldable release layer 2510 may be folded, bent, or doubled in either direction about its fold or midline region 2540 to surround or encase portions of the conductive backing layer 2560. The backing layer 2560 may be adhered, laminated, and/or otherwise attached to the foldable release layer 2510, thereby maintaining the conductive backing layer 2560 in a given position. Additionally or alternatively, in regions defined by the foldable release layer's openings 2522, 2532, adhesion between the conductive backing layer 2560 and electrodes' hydrogel layers may hold the backing layer 2560 in position.

Figure 25B:
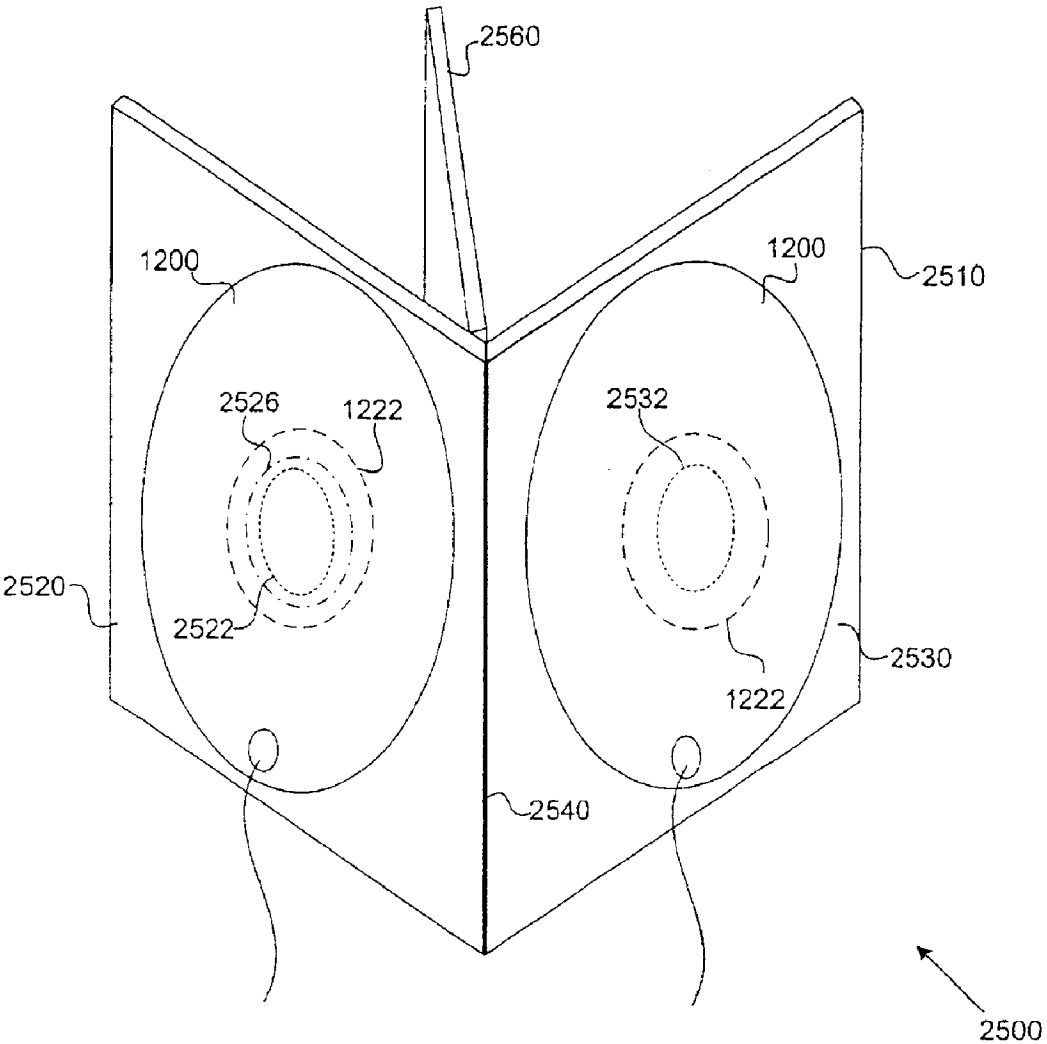
FIG. 25B is a perspective view of electrodes of FIG. 12A mounted upon the release liner of FIG. 25A.

FIG. 25B is a perspective view of a pair of voided electrodes 1200 of FIG. 12A mounted upon the release liner 2500 of FIG. 25A. Relative to FIGS. 12A and 25A, like reference numbers indicate like elements. One voided electrode 1200 may be mounted such that its void 1222 surrounds the first opening 2522 within the first mounting portion 2520, thereby surrounding at least a portion of the swatch 2526. Another voided electrode may be mounted such that its void 1222 surrounds the second opening 2532 within the second mounting portion 2530. Voided electrodes 1200 mounted in the manner shown in FIG. 25B reside upon an identical side of the release layer 2510, while the conductive backing layer 2560 may maintain contact with portions of another side of the release layer 2510.

A medical or measurement device coupled to voided electrodes 1200 mounted as shown in FIG. 25B may perform a complex impedance measurement in a manner analogous to that describe above with respect to FIGS. 23A and 23B. Based upon the result of the impedance measurement, the medical or measurement device may provide an indication of electrical path condition and/or electrode condition or fitness for use, in manners described in detail below.

Figure 26:
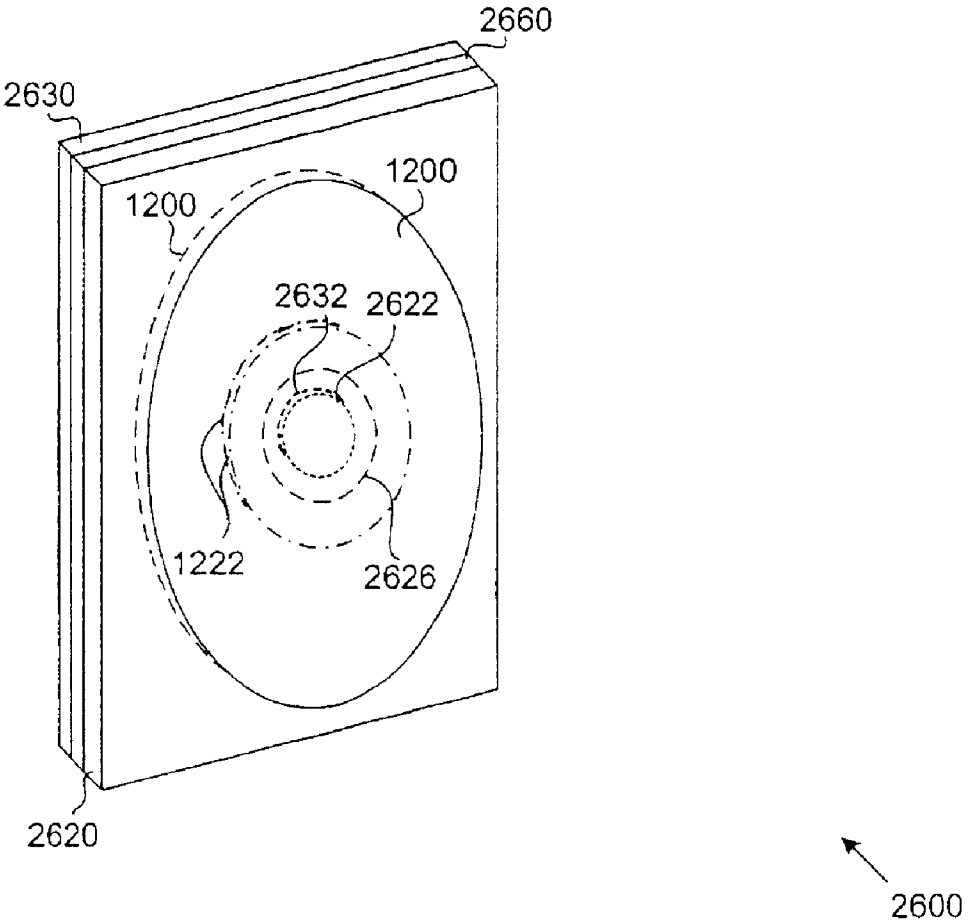
FIG. 26 is a perspective view of a release liner according to another embodiment of the invention, and electrodes of FIG. 12A mounted thereupon.

FIG. 26 is a perspective view of a release liner 2600 according to another embodiment of the invention, and a pair of voided electrodes 1200 of FIG. 12A mounted thereupon.

Relative to FIG. 12A, like reference numbers indicate like elements. In the embodiment shown, the release liner 2600 comprises a first release layer or sheet 2620, a second release layer or sheet 2630, and a conductive layer or medium 2660 disposed or residing therebetween. The first release layer 2610 includes a first opening 2622 and a swatch 2626 that covers, fills, overlaps, and/or blocks the first opening 2622. The second release layer 2630 includes a second opening 2632 therein. The first and second release layers 2620 may comprise nonconductive, non-stick materials such as those previously described, and first and second openings 2622, 2632 may be formed in conventional manners as previously described. The swatch 2626 may comprise a thin material characterized by a high dielectric constant, and may be formed or fabricated using polymeric and/or ceramic materials such as those described above.

The conductive layer 2660 may comprise a sheet or layer of conductive material, such as an Aluminum or Tin foil layer, or a hydrogel layer. The conductive layer 2660 may be adhered, laminated, and/or otherwise attached one or both release layers 2620, 2630. Additionally or alternatively, the conductive layer 2660 may be held in position by hydrogel adhesion in regions in which the first and second release layers' openings 2622, 2632 expose the conductive backing layer 2660 to the electrodes 1200.

One voided electrode 1200 may be mounted or positioned such that its void 1222 surrounds the first release layer's opening 2622, thereby surrounding at least a portion of the swatch 2622. Another voided electrode 1200 may be mounted such that its void 1222 surrounds the second release layer's opening 2632. A medical device coupled to the voided electrodes 1200 mounted as shown in FIG. 26 may perform a complex impedance measurement in a manner analogous to that describe above with respect to FIGS. 23A and 23B. Based upon the result of the impedance measurement, the medical device may provide an indication of electrical path condition and/or electrode condition or fitness for use, in manners described in detail below.

In essentially any of the embodiments shown in FIGS. 21A, 21B, 21C, 22A, 22B, 23A, 23B, 24A, 24B, 25A, 25B, and/or 26, a swatch 2126, 2226, 2326, 2426, 2526, 2626 may be adhered, bonded, laminated, and/or otherwise attached to a release liner 2100, 2400, 2500, 2600. Alternatively, direct attachment of a swatch 2126, 2226, 2326, 2426, 2526, 2626 to a release liner 2100, 2400, 2500, 2600 may be omitted. In such a situation, a swatch 2126, 2226, 2326, 2426, 2526, 2626 may be placed or positioned upon a release liner 2100, 2400, 2500, 2600 prior to placement or positioning of electrodes thereupon; or, a swatch 2126, 2226, 2326, 2426, 2526, 2626 may simply be appropriately positioned upon an electrode's hydrogel layer 1210 prior to placement or positioning of the electrode upon the release liner. Adhesion to an electrode's hydrogel layer 1210 may be sufficient to hold or maintain a swatch 2126, 2226, 2326, 2426, 2526, 2626 in a desired position. Upon removal from the release liner 2100, 2400, 2500, 2600, the performance or behavior of the electrode 150, 1200 may be essentially unaffected provided that the swatch 2126, 2226, 2326, 2426, 2526, 2626 is sufficiently small.

Variations upon the electrode/release liner embodiments above, such as those shown in FIGS. 24B, 25B, and 26, may exist. Such variations may involve other electrode embodiments, additional numbers of electrodes, and/or other release liner embodiments, in a manner consistent with the scope of the invention.

As indicated above, a medical or measurement device coupled to electrodes mounted upon a release liner may test and/or characterize an electrical path associated with the mounted or packaged electrodes in a variety of manners. Furthermore, the medical or measurement device may provide various indications of electrode condition and/or fitness for use, as described in detail hereafter. In the context of the present invention, a medical device may comprise essentially any device capable of exchanging electrical signals and/or electrical energy with a patient's body via a set of electrodes, and may be, for example, an AED. Similarly, a measurement device may comprise essentially any type of device capable of performing electrical measurements upon a set of electrodes mounted upon a release liner in accordance with the present invention.

Figure 27:
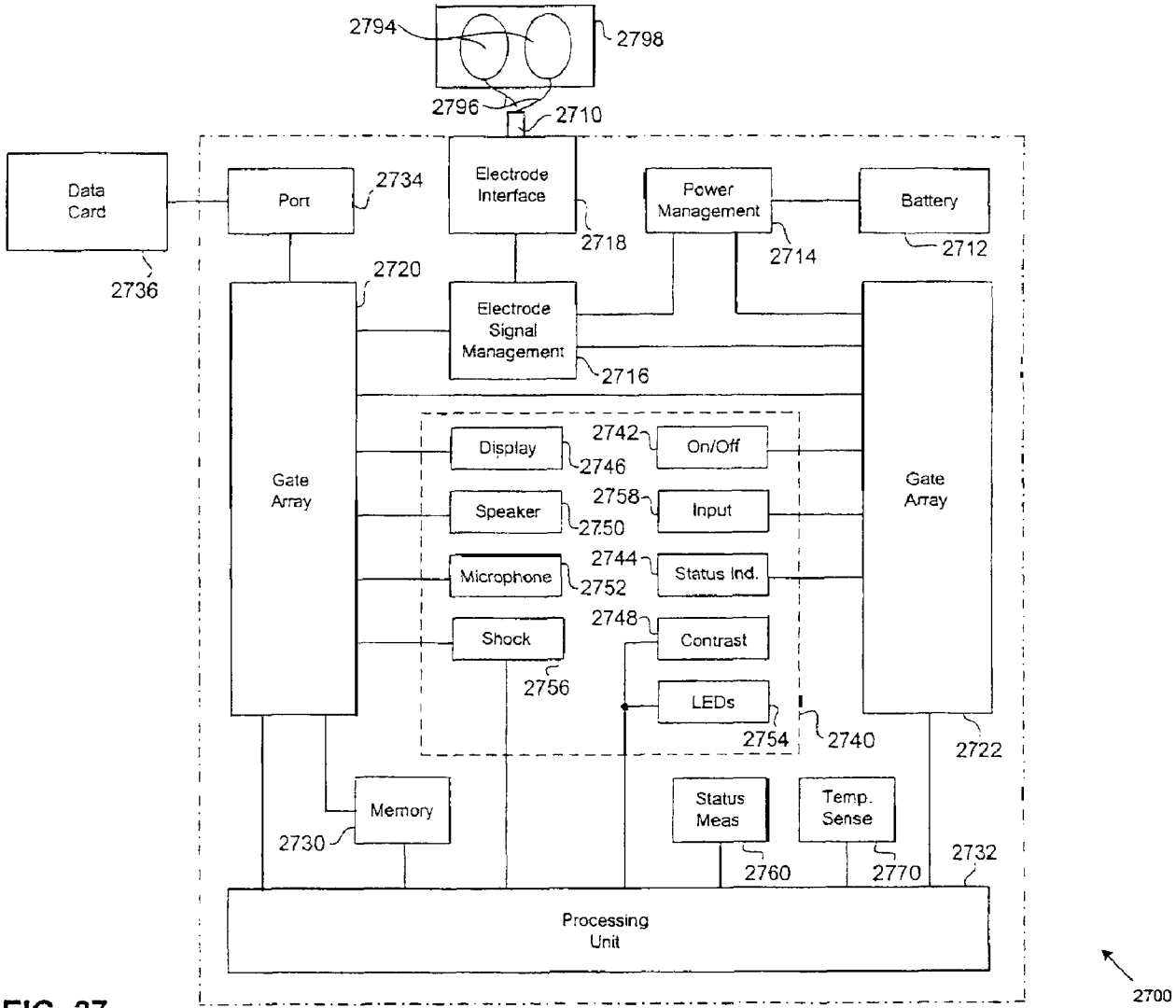
FIG. 27 is a block diagram of an Automated External Defibrillator coupled to a set of electrodes mounted upon a release liner in accordance with the present invention.

FIG. 27 is a block diagram of an AED 2700 coupled to electrodes 2794 mounted upon a release liner 2798 in accordance with an embodiment of the invention. The AED 2700 may comprise a power source or battery 2712; a power management unit 2714; an electrode signal management unit 2716; an electrode interface 2718; a first and a second gate array 2720, 2722; a memory 2730; a processing unit 2732; a communication interface or port 2734 that may be coupled to a data card 2736; an operator interface 2740 that includes a power or on/off switch 2742, a status indicator 2744, a display 2746, a contrast control 2748, a speaker 2750, a microphone 2752, a set of Light Emitting Diodes (LEDs) 2754, a shock button 2756, and an input interface 2758; a status measurement unit 2760; and a temperature sensor 2770.

The electrode interface 2718 may be coupled via a connector 2710 to a plurality of electrodes 2794 mounted upon a release liner 2798. The release liner 2798 may be any type of structure that provides a non-stick surface upon which electrodes may be mounted, and which facilitates electrical characterization of electrical current path condition and/or electrode condition or fitness for use. The release liner 2798 may comprise any type of release liner embodiment described or disclosed herein. The electrodes 2794 may be of any type disclosed herein, and/or another type. Each electrode 2794 may include a corresponding lead wire 2796 that facilitates coupling to the connector 2710. The electrodes 2794 are operable to sense a patient's ECG (not shown) and deliver an electrical waveform, pulse, or shock when mounted upon a patient's body (not shown). The electrode signal management unit 2716 may manage signal and/or energy exchange between the electrodes 2794 and other AED elements via the electrode interface 2718. The electrode signal management unit 2716 may include impedance compensation circuitry, such as that referenced above.

The status measurement unit 2760 may perform and/or direct periodic monitoring of various AED elements, systems, and/or subsystems, either automatically or in response to an AED operator's request. Operator requests may be received via the input interface 2758, which may include one or more buttons and/or a keypad. The status measurement unit 2760 may also direct the status indicator 2744 and/or the display 2746 to generate and/or present information or data to an AED operator corresponding to an operational condition of such AED elements, systems, and/or subsystems.

The status measurement unit 2760 and/or the electrode signal management unit 2716 may include electrical measurement circuitry or elements that facilitate electrical path and/or electrode characterization in accordance with the present invention. The status measurement unit 2760, possibly in conjunction with the memory 2730, the data card 2736, the processing unit 2732, the first gate array 2720, the second gate array 2722, and/or the temperature sensor 2770 may periodically or continually initiate, manage, direct, and/or perform electrical path characterization operations to determine the status and/or operating condition of one or more portions of an electrical path defined by the connector 2710, the lead wires 2796, the electrodes 2794, and the release liner 2798. Based upon one or more temperature measurements received via the temperature sensor 2770, the status measurement unit 2760 may adjust electrical measurement or test parameters to facilitate temperature compensated electrical characterization operations. The temperature sensor 2770 may comprise, for example, a thermocouple. One or more portions of the temperature sensor may be external to the AED 2700.

In one embodiment, one or more formulas or equations and/or data tables derived from and/or based upon empirical impedance versus temperature data may reside within the memory 2730. Via insertion of a current or most-recent temperature measurement and a corresponding current or most-recent impedance measurement into an appropriate equation, the status measurement unit 2760 and/or the processing unit 2732 may determine an actual, corrected, or adjusted impedance value corresponding to mounted electrodes currently under consideration. An equation that provides corrected or adjusted impedance values in accordance with temperature and measured impedance values may be determined, for example, by standard curve-fitting techniques following empirical data acquisition. The status measurement unit 2760 and/or the processing unit 2732 may alternatively or additionally rely upon one or more data tables to look up a corrected or adjusted impedance value corresponding to mounted electrodes currently under consideration. Those skilled in the art will recognize that a data table lookup procedure may return a closest or an interpolated value depending upon implementation details.

The status measurement unit 2760 may also periodically or continually initiate, perform, manage, and/or direct determination or calculation of one or more estimated or expected time intervals during which electrodes 2794 are likely to exhibit a given operating condition. Such determinations or calculations may be performed in conjunction with the memory 2730, the data card 2736, the processing unit 2732 and/or one or both gate arrays 2720, 2722. The memory 2730 and/or the data card 2736 may store program instruction sequences for initiating, performing, and/or directing electrical path characterization operations. Finally, the status measurement unit 2760 may initiate or perform the aforementioned operations automatically or in response to an AED operator's request.

Electrical path characterization operations may include or involve temperature compensated impedance measurements such as those described herein, as well as generation, presentation, and/or provision of one or more indications of electrical path and/or electrode condition. Electrical path characterization operations may involve stored data, such as electrical measurement results obtained or determined at one or more earlier times. Such stored data may be used, for example, to determine a present rate of change in electrode fitness, or an estimate thereof. Stored data may reside within the memory 2730, and/or upon the data card 2736.

Based upon measurement results obtained and/or calculations or determinations made during the electrical path characterization operations, the status measurement unit 2760 may direct the status indicator 2744, the display 2746, the speaker 2750, and/or the LEDs 2754 to generate and/or present status information and/or a set of messages to an AED operator. The status information and/or messages may be in audible, textual, symbolic, and/or graphical formats.

The status information and/or the messages may indicate that the electrical path is in adequate, acceptable, or good condition, or that one or more portions of the electrical path may be damaged or defective. Alternatively or additionally, the status information and/or the message may provide an indication of electrode condition or fitness for use. An AED operator may subsequently take appropriate action if required, such as replacement of packaged electrodes.

In the event that an electrical path characterization operation and/or impedance measurement corresponds to a short or open circuit condition, a connector 2710, a lead wire 2796, an electrode 2794, and/or one or more portions of the release liner 2798 may be damaged and/or defective. In such a case, the status measurement unit 2760 may direct the status indicator 2744, the display 2746, and/or the speaker 2750 to present a corresponding message or indication to an AED operator. Such a message may be, for example, "REPLACE ELECTRODES IMMEDIATELY."

In the event that an electrical path characterization operation and/or impedance measurement results in a measured impedance value exceeding a given value or falling outside a given range, the status measurement unit 2760 may direct the status indicator 2744, the display 2746, and/or the speaker 2750 to generate and/or present a corresponding message, for example, "REPLACE ELECTRODES SOON." The status measurement unit 2760 or other element may additionally or alternatively generate a beep or other sound until electrode replacement has occurred.

The status indicator 2744 may alternatively or additionally incorporate, generate, present and/or maintain one or more graphical or other type of visual metaphors that provide an indication of electrode condition and/or an expected amount of electrode lifetime remaining. Various types of indicators and/or interfaces for indicating electrode condition and/or an expected amount of electrode lifetime remaining are described in detail hereafter.

Figure 28A:
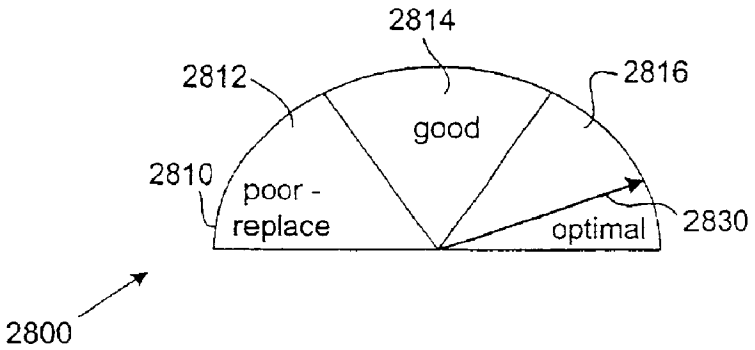
FIG. 28A is an illustration of an electrode condition indicator in accordance with an embodiment of the invention.

FIG. 28A is an illustration of an electrode condition indicator 2800 in accordance with an embodiment of the invention. The electrode condition indicator 2800 may comprise a panel 2810 and an indicating element 2830. The panel 2810 may include a set of quality markings and/or regions 2812, 2814, 2816, where each such region 2812, 2814, 2816 corresponds to an electrode operating condition or operating condition range. For example, the electrode condition indicator 2800 may include a first quality region 2812 corresponding to good or optimal electrode condition; a second quality region 2814 corresponding to acceptable or fair electrode condition; and a third quality region 2816 corresponding to poor or unacceptable electrode condition. Other embodiments may incorporate additional or fewer quality regions. For example, in an alternate embodiment, an electrode condition indicator 2800 may include quality regions corresponding to an excellent quality or condition rating, a good quality or condition rating, an acceptable quality or condition rating, a poor quality or condition rating, and an unusable quality or condition rating. Any given quality region 2812, 2814, 2816 may include one or more color codings; and/or one or more quality regions 2812, 2814, 2816 may include text and/or symbols corresponding to an electrode operating condition.

The indicating element 2830 may comprise an arrow, needle, bar, or other type of element that may be positioned within any given quality region 2812, 2814, 2816. Based upon electrical path characterization and/or impedance measurement results, the status measurement unit 2760 of FIG. 27 may issue signals to the electrode condition indicator 2800 to set or establish a given position for the indicating element 2830 relative to the quality regions 2812, 2814, 2816, The indicating element's relative position may provide a fuel gauge metaphor for electrode condition and/or fitness for use. As electrode condition deteriorates over time, the indicating element 2830 may move into and/or through quality regions that correspond to poorer electrode fitness for use.

The indicating element 2830 may additionally or alternatively comprise or include a device or interface that changes color in response to changes in a surrounding environment, such as variations in relative humidity. The indicating element 2830 may incorporate one or more color references to convey a degree of reliability and/or an estimated usable electrode lifetime.

The electrode condition indicator 2800 may be implemented in a graphical manner upon an electrical interface such as a status indicator 2744 or display 2746 of FIG. 27. Alternatively, the electrode condition indicator 2800 may be implemented as a physical interface that may comprise conventional electrical, mechanical, electromechanical, chemical, and/or electrochemical elements. Such a physical interface may form a portion, subsystem, or element of the status indicator 2744. For example, the panel 2810 may be implemented as a physical element within a corresponding housing (not shown), and the indicating element 2830 may be a piece of plastic and/or metal coupled to a shaft (not shown). The shaft may be coupled to a positioning device or actuator (not shown) that is responsive to signals received from the status measurement unit 2760 of FIG. 27.

Figure 28B:
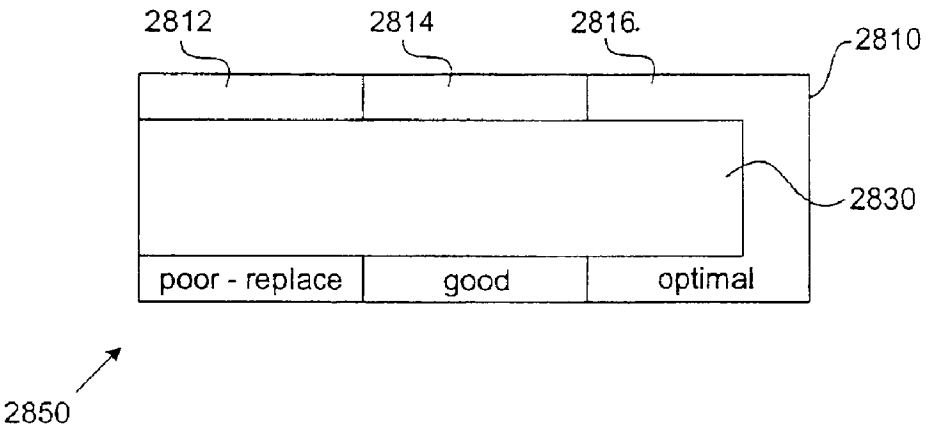
FIG. 28B is an illustration of an electrode condition indicator in accordance with another embodiment of the invention.

FIG. 28B is an illustration of an electrode condition indicator 2850 according to another embodiment of the invention. Relative to FIG. 28A, the electrode condition indicator 2850 of FIG. 28B may comprise corresponding, identical and/or essentially identical types of elements; hence, like reference numbers indicate like or corresponding elements. In the embodiment of FIG. 28B, the indicating element 2830 may comprise a bar that obscures, blocks, or covers one or more quality regions 2812, 2814, 2816 and/or portions thereof, successively exposing or blocking regions 2812, 2814, 2816 corresponding to poorer electrode condition or fitness for use over time in response to signals received via the status measurement unit 2760 of FIG. 27. The indicating element 2830 in such an embodiment may exhibit generally continuous or successive movement through one or more quality regions 2812, 2814, 2816 over time.

Figure 29A:
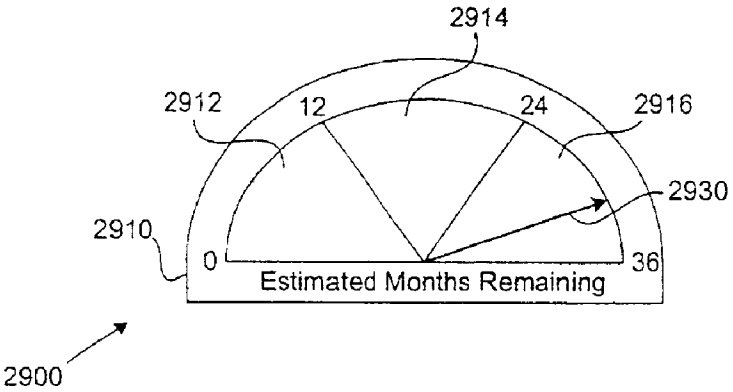
FIG. 29A is an illustration of a remaining time indicator in accordance with an embodiment of the invention.

FIG. 29A is an illustration of a remaining time indicator 2900 in accordance with an embodiment of the invention. The remaining time indicator 2900 may comprise a panel 2910 and an indicating element 2930, in a manner analogous to that described above for the electrode condition indicator 2800 of FIG. 28A. The panel 2910 may include a set of regions and/or markings 2912, 2914, 2916. Such markings may correspond to an estimated amount of time that an electrode may be likely to remain at a given performance or condition level, or an estimated amount of time remaining before electrode replacement is likely to be required.

For example, a first marking 2912 may correspond to a duration of twelve months, while a second and a third marking 2914, 2916 may correspond to a duration of twenty four and thirty six months, respectively. Those skilled in the art will recognize that the first, second, and/or third markings 2912, 2914, 2916 may correspond to time periods other than those recited herein. Each region or marking 2912, 2914, 2916 may include associated text that indicates a time interval and/or a condition to which the region or marking 2912, 2914, 2916 corresponds. Each region or marking may also be color coded, in a manner analogous to that described above with reference to FIG. 28A.

The indicating element 2930 may comprise an arrow, needle, bar, or other type of element that may be positioned upon, within, or between any given region or marking 2912, 2914, 2916. Based upon 1) current and/or most-recent electrical path characterization and/or impedance measurement results; 2) prior electrical path characterization and/or impedance measurement results; and/or 3) empirical data characterizing hydrogel moisture loss, impedance measurement rates of change, and/or other factors that may affect electrode condition over time, the status measurement unit 2760 may issue signals to the remaining time indicator 2900 to set or establish a given position for the indicating element 2930 relative to the regions or markings 2912, 2914, 2916.

The position of the indicating element 2930 relative to the markings 2912, 2914, 2916 may convey, for example, that the electrodes have approximately X months left in an optimal performance zone, or Y months remaining until replacement is recommended or required, where determination of X and/or Y may be based upon a rate of change in current, prior, and/or empirical electrical properties. Electrical path property, characterization, and/or impedance measurement results, as well as the aforementioned empirical properties or data, may be stored within the memory of the AED 2700 of FIG. 27. The memory may include various types of nonvolatile and/or Read Only Memory (ROM) to facilitate efficient storage of such information.

In a manner analogous to that for the electrode condition indicator of FIG. 28A, the position of the indicating element 2930 within the remaining time indicator 2900 relative to the regions or markings 2912, 2914, 2916 may provide a fuel gauge metaphor for an expected remaining electrode lifetime. As electrode condition deteriorates over time, the indicating element 2930 may move through or past regions and/or markings 2912, 2914, 2916 that correspond to shorter or decreased expected electrode lifetime.

The remaining time indicator 2900 may be implemented in a graphical manner upon an electrical interface such as a status indicator 2744 or display 2746 of FIG. 27. Alternatively, the remaining time indicator 2900 may be implemented as a physical interface that may comprise conventional electrical, mechanical, and/or electromechanical elements. Such a physical interface may form a portion, subsystem, or element of the status indicator 2744. For example, the panel 2910 may be implemented as a physical element within a corresponding housing (not shown), and the indicating element 2930 may be a piece of plastic and/or metal coupled to a shaft (not shown). The shaft may be coupled to a positioning device or actuator (not shown) that is responsive to signals received from the status measurement unit 2760 of FIG. 27.

Figure 29B:
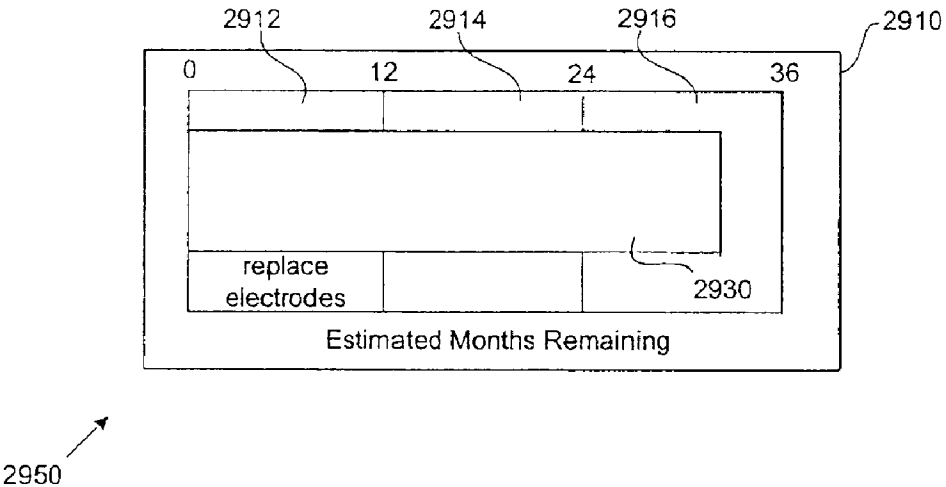
FIG. 29B is an illustration of a remaining time indicator in accordance with another embodiment of the invention.

FIG. 29B is an illustration of a remaining time indicator 2950 in accordance with another embodiment of the invention. Relative to FIG. 29A, the remaining time indicator 2950 of FIG. 29B may comprise corresponding, identical and/or essentially identical types of elements; hence, like reference numbers indicate like elements. In the embodiment of FIG. 29B, the indicating element 2930 may comprise a bar that obscures, blocks, or covers one or more regions or markings 2912, 2914, 2916 and/or portions thereof, successively exposing or blocking such markings 2912, 2914, 2916 to indicate diminishing expected electrode lifetime in response to signals received over time via the status measurement unit 2760 of FIG. 27.

Figure 30:
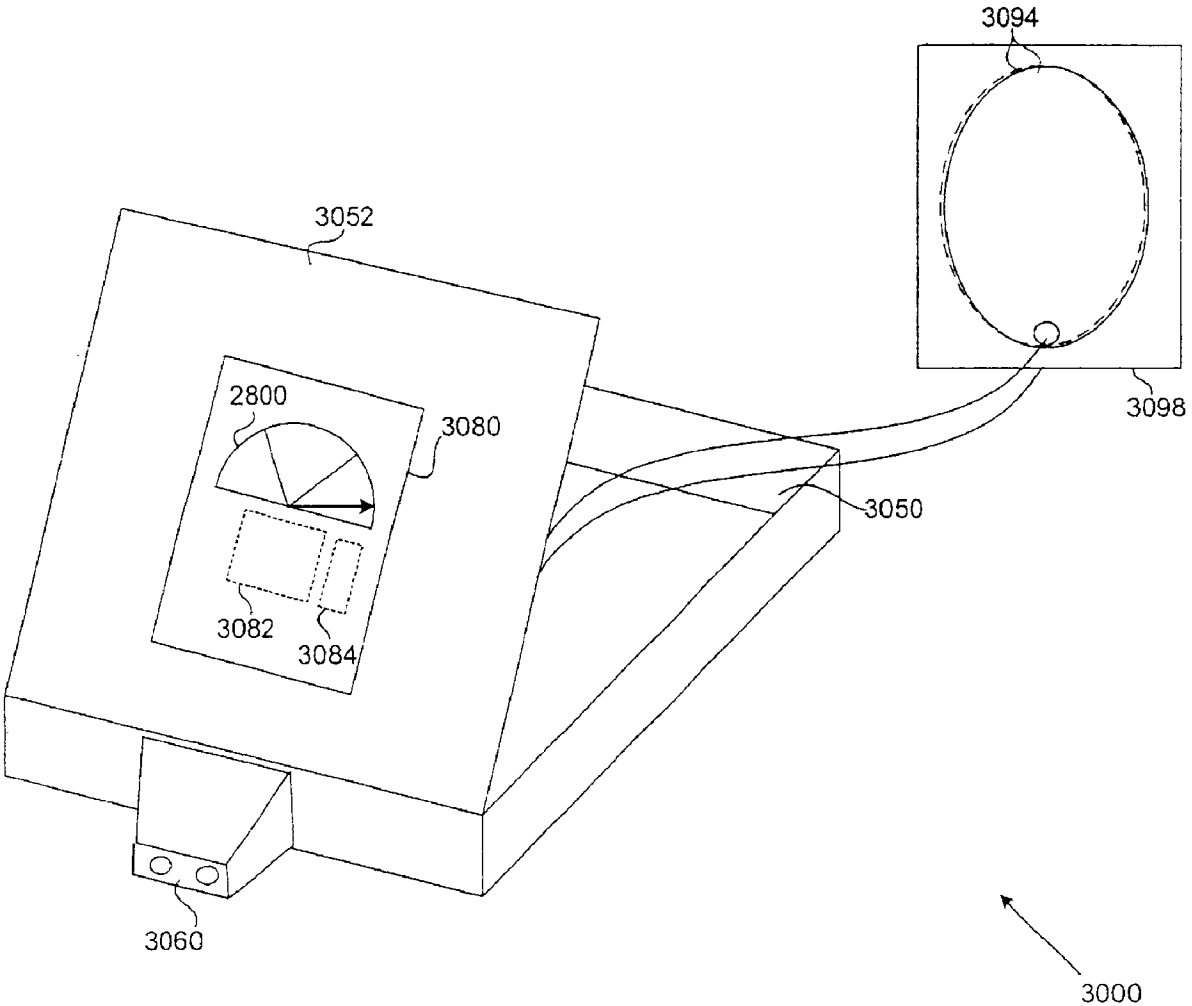
FIG. 30 is a perspective view of a package incorporating an electrode condition and/or remaining time indicator and electrodes mounted upon a release liner.

Any given electrode condition indicator 2800, 2850 and/or remaining time indicator 2900, 2950 may additionally or alternatively be incorporated into a packaged electrode structure. FIG. 30 is a perspective view of a package 3000 in which an indicator 3080 and electrodes 3094 mounted upon a release liner 3098 reside. The electrodes 3094 and/or the release liner 3098 may be of a variety of types, including those described herein. Relative to FIGS. 28A and 29A, like reference indicate like elements.

The package 3000 may comprise a housing 3050 having a removable lid 3052 and an electrical interface 3060, in a manner analogous to that described above in relation to FIG. 4. Electrodes 3094 mounted upon the release liner 3098 may be sealed within the package 3000. The electrical interface 3060 may comprise a connector that facilitates electrical coupling of the electrodes 3094, and possibly the indicator 3080, to a medical device. The indicator 3080 may comprise an electrode condition indicator 2800, 2850 and/or a time remaining indicator 2900, 2950 such as those previously described. The indicator 3080 may reside within or upon the package 3000.

In one embodiment, the indicator 3080 may be coupled to a medical or measurement device, and thus the medical or measurement device may provide electrical power as well as measurement and/or computational capabilities required to indicate electrode fitness for use and/or an estimated duration associated with an electrode condition via the indicator 3080. In an alternate embodiment, the indicator 3080 may comprise an electrode condition and/or time remaining indicator 2800, 2850, 2900, 2950, plus a control circuit 3082 and an independent power source 3084 such as a battery. The control circuit 3082 may include measurement, calculation, and/or processing elements necessary for determining an electrode condition and/or an estimated duration corresponding to electrode condition.

Figure 31:
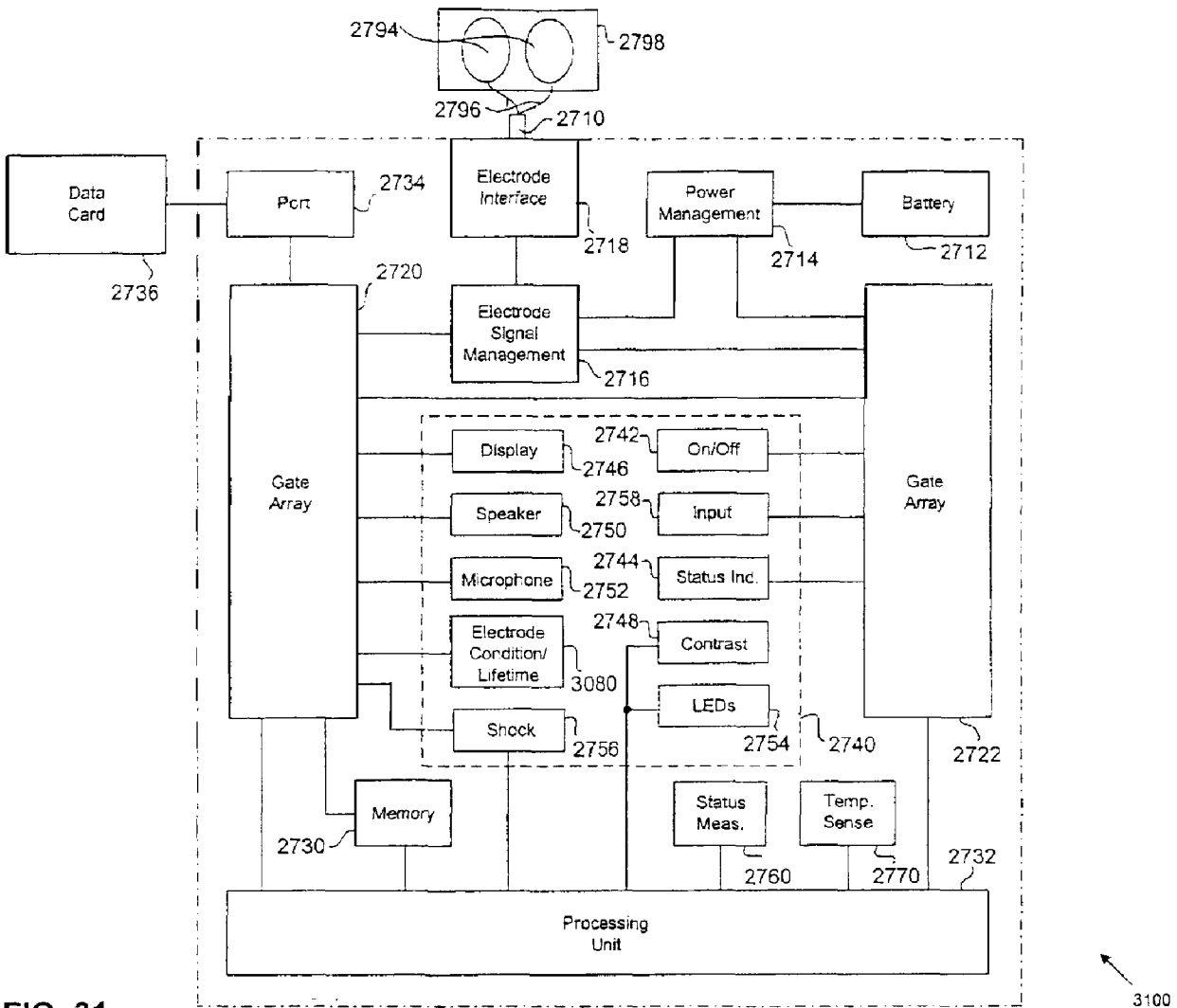
FIG. 31 is a block diagram of an Automated External Defibrillator that includes an electrode condition indicator and/or an estimated remaining electrode lifetime indicator.

A medical or measurement device may itself include an electrode condition and/or a time remaining indicator 3080 therein or thereupon. FIG. 31 is a block diagram of an AED 3100 that includes an indicator 3080. Relative to FIGS. 27 and 30, like reference numbers indicate like elements. The indicator 3080 may comprise an electrode condition and/or a time remaining indicator, which may be identical, essentially identical, and/or analogous to those described above with respect to FIGS, 28A, 28B, 29A, and/or 29B.

What is claimed is:

[1. A release liner comprising:

a release layer, said release layer having an opening therein; and one from the group of a moisture permeable membrane and a moisture absorbent membrane, the membrane covering the opening.]

[2. The release liner of claim 1, wherein the membrane comprises paper.]

[3. The release liner of claim 1, wherein the membrane is maintained in a position via attachment to the release layer.]

4. A release liner comprising:

a first release layer;

one from the group of a moisture permeable membrane and a moisture absorbent membrane; and a second release layer, wherein the first release layer includes an opening therein, and wherein the second release layer includes an opening therein.

5. The release liner of claim 4, wherein the membrane comprises paper.

*6. An electrode system for a medical device employing an electrode to exchange signals with a subject comprising:*

*a conductive adhesive layer; and*

*a conductive layer affixed to the conductive adhesive layer, the conductive layer having a nonconductive region therein,*

*wherein the conductive adhesive layer overlays the nonconductive region,*

*wherein the conductive adhesive layer and the conductive layer comprise a first electrode; and further comprising:*

*a second conductive adhesive layer;*

*a second conductive layer affixed to the second conductive adhesive layer, the second conductive layer having a nonconductive region therein, the second conductive adhesive layer overlaying the nonconductive region of the second conductive layer,*

*wherein the second conductive adhesive layer and the second conductive layer comprise a second electrode; and*

*a release liner, located between the conductive adhesive layers of the first and second electrodes, the release liner having a a first release layer, one from the group of a moisture permeable membrane and a moisture absorbent membrane, and a second release layer, wherein the first release layer includes an opening therein, and wherein the second release layer includes an opening therein,*

*and further wherein the conductive adhesive layers of the first and second electrodes are electrically connected in the vicinity of the nonconductive regions.*

*7. The electrode system of claim 6, wherein the nonconductive regions comprise voids in the conductive layers.*

*8. The electrode system of claim 6, further comprising:*

*a first lead wire electrically coupled to the conductive layer of the first electrode;*

*a second lead wire electrically coupled to the conductive layer of the second electrode; and*

*a measurement circuit, located in the medical device, and electrically coupled to the first and second lead wires, and operable to measure an electrical characteristic of the conductive adhesive layers.*

*9. The electrode system of claim 8, wherein the measurement circuit is operable to measure at least one of a current or impedance of the conductive adhesive layers.*

*10. The electrode system of claim 6, wherein the low impedance region of the release liner is smaller than the nonconductive regions of the conductive layers.*

*11. An electrode system for a medical device employing an electrode to exchange signals with a subject comprising:*

*a conductive adhesive layer having a lateral dimension and a thickness dimension;*

*an electrical conductor electrically coupled to the conductive adhesive layer; and*

*a conductive layer having a lateral dimension and affixed to the conductive adhesive layer with its lateral dimension substantially in parallel with the lateral dimension of the conductive adhesive layer, the conductive layer constraining the passage of current in at least a portion of the shortest current path between the conductive layer and the electrical conductor to be in the lateral dimension of the conductive adhesive layer;*

*wherein the conductive layer and the affixed conductive adhesive layer comprise a first electrode;*

*wherein the electrical conductor comprises a second electrode having a conductive layer and an affixed conductive adhesive layer; and*

*a release liner to which the conductive adhesive layers of the first and second electrodes are attached, the release liner having a first release layer, one from the group of a moisture permeable membrane and a moisture absorbent membrane, and a second release layer, wherein the first release layer includes an opening therein, and wherein the second release layer includes an opening therein to form a low impedance region which electrically couples the conductive adhesive layer of the first electrode to the second electrode.*

*12. The electrode system of claim 11, wherein the conductive layer of the first electrode has a high impedance region therein;*

*wherein the low impedance region of the release liner opposes the high impedance region of the conductive layer across the thickness dimension of the conductive adhesive layer of the first electrode.*

*13. The electrode system of claim 12, wherein the low impedance region of the release liner is smaller than the high impedance region of the conductive layer.*

*14. The electrode system of claim 13, wherein the passage of current is constrained to the lateral dimension of the conductive adhesive layer of the first electrode where the high impedance region of the conductive layer opposes the release liner adjacent to the low impedance region of the release liner.*

*15. An electrode system for a medical device employing an electrode to exchange signals with a subject comprising:*

*a release liner having a first release layer, one from the group of a moisture permeable membrane and a moisture absorbent membrane, and a second release layer, wherein the first release layer includes an opening therein, and wherein the second release layer includes an opening therein to form a low impedance region;*

*a first electrode having a conductive adhesive layer overlaying a surface of a conductive layer, the conductive adhesive layer having a thickness dimension which is orthogonal to the surface of the conductive layer and a lateral dimension, the conductive adhesive layer transporting current between the conductive layer and the low impedance region of the release liner in the lateral dimension of the conductive adhesive layer during a test mode.*

*16. An electrode system for a medical device employing an electrode to exchange signals with a subject comprising:*

*a release liner having a first release layer, one from the group of a moisture permeable membrane and a moisture absorbent membrane, and a second release layer, wherein the first release layer includes an opening therein, and wherein the second release layer includes an opening;*

*a first electrode attached to the first release layer of the release liner and having a conductive adhesive layer overlaying a conductive layer;*

*a second electrode attached to the second release layer of the release liner and having a conductive adhesive layer overlaying a conductive layer, the conductive adhesive layer of the second electrode being electrically coupled to the conductive adhesive layer of the first electrode,*

*wherein the conductive adhesive layer of the first electrode is in contact with the conductive adhesive layer of the second electrode through a low impedance region of the release liner,*

*wherein the impedance between the conductive layers of the electrodes is outside the expected impedance range of the subject.*

*17. The electrode system of claim 16, wherein the thickness of the conductive adhesive layer of the first electrode exhibits a first impedance;*

*wherein the thickness of the conductive adhesive layer of the second electrode exhibits a second impedance; and*

*wherein the impedance between the conductive layers of the electrodes is greater than the sum of the first and second impedances.*

*18. The electrode system of claim 17, wherein the impedance between the conductive layers of the electrodes includes a current path through a conductive adhesive layer which is orthogonal to the thickness dimension of the conductive adhesive layer.*

* * * * *